US009333193B2

(12) United States Patent
Hoffman et al.

(10) Patent No.: US 9,333,193 B2
(45) Date of Patent: May 10, 2016

(54) COMPOSITIONS AND METHODS FOR TREATING TUBERCULOSIS

(75) Inventors: Paul S. Hoffman, Charlottesville, VA (US); Timothy L. MacDonald, Charlottesville, VA (US); Eric R. Houpt, Keswick, VA (US); Thomas E. Ballard, Jr., Middletown, CT (US)

(73) Assignee: UNIVERSITY OF VIRGINIA PATENT FOUNDATION, Charlottesville, VA (US)

( * ) Notice: Subject to any disclaimer, the term of this patent is extended or adjusted under 35 U.S.C. 154(b) by 158 days.

(21) Appl. No.: 13/885,414

(22) PCT Filed: Sep. 20, 2011

(86) PCT No.: PCT/US2011/052308
§ 371 (c)(1),
(2), (4) Date: Aug. 14, 2013

(87) PCT Pub. No.: WO2012/040170
PCT Pub. Date: Mar. 29, 2012

(65) Prior Publication Data
US 2013/0317070 A1    Nov. 28, 2013

Related U.S. Application Data

(60) Provisional application No. 61/384,369, filed on Sep. 20, 2010.

(51) Int. Cl.
A61K 31/381 (2006.01)
A61P 31/04 (2006.01)
A61P 31/06 (2006.01)
A61K 31/426 (2006.01)
A61K 31/427 (2006.01)

(52) U.S. Cl.
CPC ............ *A61K 31/381* (2013.01); *A61K 31/426* (2013.01); *A61K 31/427* (2013.01)

(58) Field of Classification Search
CPC ................................................... A61K 31/381
USPC ................. 514/444, 447, 448; 549/59, 68, 69
See application file for complete search history.

(56) References Cited

U.S. PATENT DOCUMENTS 2,735,798 A    2/1956    Kupferberg et al.
5,071,865 A    12/1991    Beck et al.
(Continued)

FOREIGN PATENT DOCUMENTS

EP    0566138 A1    10/1993
FR    1306603        9/1962
(Continued)

OTHER PUBLICATIONS

Ancizu et al. Molecules 2009, 14, 2256-2272.*
Bellenghi et al. Gazzetta Chimica Italiana 1952, 82, 773-807, Abstract.*
Definition of prevent, Princeton University "About WordNet." WordNet. Princeton University. 2010. <http://wordnet.princeton.edu>, accessed on Sep. 18, 2012.*
Wagner et al. Infection 2003, 31 (5), 257-270.*
(Continued)

*Primary Examiner* — Sreeni Padmanabhan
*Assistant Examiner* — Irina Neagu
(74) *Attorney, Agent, or Firm* — Rodney L. Sparks

(57) ABSTRACT

The invention provides for the use of antimicrobial chemical entities based on a nitrothiazolide backbone that exhibit anti-mycobacteria activity, including the *mycobacterium* causing tuberculosis. Multiple compounds were synthesized and screened for anti-tuberculosis activity. Disclosed herein are a series of compounds with anti-tuberculosis activity, including six leads that completely inhibited bacterial growth at 5 micrograms per ml or less. Three of these compounds were tested to determine MIC and these ranged between 1 and 4 micrograms per ml against both drug susceptible *Mycobacterium tuberculosis* strains and strains that are multi-drug resistant (MDR) including XDR strains. The compounds developed are derived from parent compound nitazoxanide, which had no inhibitory activity in the stringent testing format used herein. The derivatives were synthesized using a di-nitro-thiophene or 4-Chloro-5-Nitro-thiazole scaffold and R groups connected via a peptide bond (NHCO) to cyclic compounds such as benzene, thiophene or furans. Many of these compounds have broad spectrum activity against Gram positive bacteria including *Staphylococcus aureus* (MRSA) and *Staphylococcus epidermidis*. Several of these lead compounds were not toxic for mice at 200 mg/Kg doses administered over a period of three days.

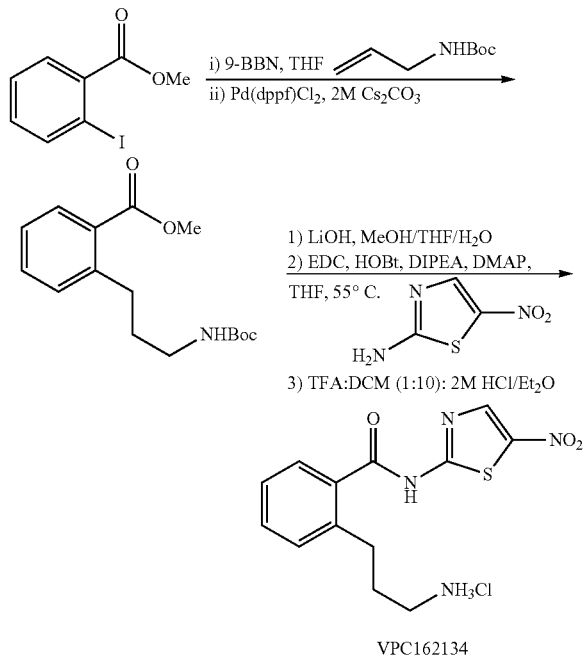

VPC162134

18 Claims, 15 Drawing Sheets

(56) References Cited

U.S. PATENT DOCUMENTS

| | | | |
|---|---|---|---|
| 5,578,621 | A | 11/1996 | Rossignol |
| 5,965,590 | A | 10/1999 | Rossignol |
| 2005/0113420 | A1 | 5/2005 | Nan et al. |
| 2009/0036467 | A1 | 2/2009 | Rossignol et al. |
| 2012/0010187 | A1 | 1/2012 | Hoffman et al. |
| 2015/0018330 | A1* | 1/2015 | Hoffman et al. ........... 514/210.2 |

FOREIGN PATENT DOCUMENTS

| | | |
|---|---|---|
| FR | 79201 | 11/1962 |
| GB | 723948 | 2/1955 |
| JP | 3918145 B | 8/1964 |
| WO | WO0026202 A1 | 5/2000 |
| WO | WO03089419 A1 | 10/2003 |
| WO | WO2004031179 A1 | 4/2004 |
| WO | WO2004056177 A2 | 7/2004 |
| WO | WO2007081974 A2 | 7/2007 |
| WO | WO2007125109 | 11/2007 |

OTHER PUBLICATIONS

Luo, Qun-Li, et al., "Inhibitors of type I MetAps containing pyridine-2-carboxylic acid thiazole-2-ylamide. Part I: SAR studies on the determination of the key scaffold", Bioorganic & Medicinal Chemistry Letters, 2005, vol. 15, pp. 635-638.

Hedal, Christopher J., et al., "Discovery and SAR of 2-aminothiazone inhibitors of cyclin-dependent kinase 5/p25 as a potential treatment for Alzheimer's disease", Bioorganic & Medicinal Chemistry Letters, 2004, vol. 14, pp. 552-1-5525.

McVay, Catherine S., et al., "In Vitro and In Vivo Activities of Nitazoxanide against Clostridium difficile", Antimicrob. Agents Chemother., vol. 44, No. 9, 2000, pp. 2254-2258, XP55032067.

Sokolova, T.N., et al., "Synthesis and Antimicrobial Activity of Derivatives", Pharmaceutical Chemistry, vol. 27, No. 3, 1993, pp. 209-211, XP002679654.

Werbel, L.M., "Derivatives of 2-Amino-5-nitrothiazole as Potential Schistosomicides", Journal of Medicinal Chemistry, vol. 14, No. 1, 1971, pp. 10-16, XP002679655.

Bushby, S.R.M., "The Antitrichomal Activity of Amido-Nitrothiazols", J. Pharmacol., vol. 7, 1955, pp. 112-114, XP009161073.

Hoffman, Paul S., et al., "Antiparasitic Drug Nitazoxanide Inhibits the Pyruvate Oxidoreductases of Helicobacter pylori, Selected Anaerobic Bacteria and Parasites, and Campylobacter jejuni", Antimicrobial Agents and Chemo., Mar. 2007, vol. 51, No. 3., p. 868-876.

de Carvalho, Luiz Pedro S., et al., "Nitazoxanide Kills Replicating and Nonreplicating Mycobacterium tuberculosis and Evades Resistance", J. Med. Chem., 2009, 52, p. 5789-5792.

Dubreuil, L., et al., "In vitro evaluation of activities of nitazoxanide and tizoxanide against anaerobes and aerobic organisms", Antimicrob. Agents Chemother., 40:2266-2270, 1996.

Hemphill, A. et al., "Nitazoxanide, a broad-spectrum thiazolide anti-effective agent for the treatment of gastrointestinal infections", Expert Opin. Pharmacother. 7:953-964, 2006.

Pankuch, G. A., et al., "Activities of Tizoxanide and Nitazoxanide Compared to Those of Five Other Thiazolides and Three Other Agents against Anaerobic Species", Antimicrob. Agents Chemother. 50: 1112-1117, 2006.

Sisson, G., et al., "Enzymes Associated with Reductive Activation and Action of Nitazoxanide, Nitrofurans, and Metronidazole in Helicobacter pylori", Antimicrob. Agents Chemother. 46:2116-23, 2002.

Zulu, I., et al., "Nitazoxanide for persistent diarrhoea in Zambian acquired immune deficiency syndrome patients: a randomized-controlled trial", Aliment Pharmacol. Ther., 21:757-763, 2005.

Ballard, T. Eric, et al., Synthesis and Antimicrobial Evaluation of Nitazoxanide-Based Analogues: Identification of Selective and Broad Spectrum Activity, epub Dec. 29, 2010, ChemMedChem, Feb. 7, 2011, 6 (2): 362-377.

Warren, C., et al., "Amixicile, a Novel Inhibitor of Pyruvate:Ferredoxin Oxidoreductase, Shows Efficacy against Clostridium difficile in a Mouse Infection Model", Antimicrobial Agents & Chemotherapy, Aug. 2012, V 56, No. 8, p. 4103-4111.

Jameson-Lee, M., et al., "DsbA2 (27 kDa Com1-like protein) of Legionella pneumophila catalyses extracytoplasmic disulphide-bond formation in proteins including the Dot/Icm type IV secretion system", Molecular Microbiolog, doi: 10.1111/j.1365-2958.2011.07615.

Madulo-Leblond, et al., "Studies on the nitro derivatives of biological interest. XXIII. New data concerning molluscicidal properties of 2-benzamido-5-nitrothiazole halogenated derivates", CA 95:92272, 1961, pp. 1-12.

Cavier, et al., "Research on nitro derivatives of biological interest. XVI. Protozoacidal, anthelmintic and molluscicidal structure activity relationships in the 2-benzamido-5-nitrothiazole series (1)", EU Jrnl of Med. Chem. 1978, 13(6), pp. 539-543, English Translation.

Cavier, R., et al., EU Jrnl of Med. Chem. 1978, 13(6), pp. 439-543.

Ganapathi, et al., "Chemistry of the thiazoles. I. Synthesis of 5-amino-thiazole derivatives", CA 40:20760, 1946, pp. 1-4.

Priestly, et al., "Replacement of halogen by the nitro group in halogenated 2-acetamidothiophenes", CA 41: 22387, 1947, p. 1.

Madulo-Leblond, et al., "Research on Nitrate Derivatives of Biological Interest XXIII. New Data Relative to the Molluscicide Properties of Halogen Derivatives of 2-Genzamido-5-Nitro Thiazoles", EU Jrnl of Med. Chem. 1981, 16(3), pp. 267-270, English Translation.

Madulo-Leblond, et al., EU Jrnl of Med. Chem. 1981, 16(3), pp. 267-270.

Sugihara, et al., "Nitrothiazole derivatives having nitrofuryl groups", CA 62: 19716, 1965, p. 1.

Husain, et al., "Search for Potent Anthelmintics—Part XIII 2-(3,5-Substituted Salicylamido/Cinnamido)-4,5-Substituted Thiazoles", Jrnl of IN Chemical Society, 1979, 56(9), pp. 917-918.

Chemical Abstracts Registry No. 710310-01-04, Jul. 15, 2004, p. 1.

Xuong, et al., "Thiazole derivatives and process for their preparation", FR 1306603, 1962, pp. 1-8, English Translation.

Xuong, et al., FR 79201, 1962, pp. 1-2, English Translation.

* cited by examiner

Aliphatic Derivatives of 2-amino-5-nitrothiazole

Aliphatic Amine Analogues of 2-amino-5-nitrothiazole

Amino Acid Analogues of 2-amino-5-nitrothiazole

Anthranilic Analogues of 2-amino-5-nitrothiazole

Pyridine Analogues of 2-amino-5-nitrothiazole

Indole Analogues of 2-amino-5-nitrothiazole

Carboxylic Acid Analogues of 2-amino-5-nitrothiazole

Dimer-like Analogues of 2-amino-5-nitrothiazole

Halide Analogues of 2-amino-5-nitrothiazole

Monosubstituted Analogues of 2-amino-5-nitrothiazole

Disubstituted Analogues of 2-amino-5-nitrothiazole

Furan Analogues of 2-amino-5-nitrothiazole

Thiophene Analogues of 2-amino-5-nitrothiazole

Amide Isosteres of 2-amino-5-nitrothiazole

Analogues of 2-amino-4-chloro-5-nitrothiazole

Analogues of 2-amino-3,5-dinitrothiophene

COMPOSITIONS AND METHODS FOR TREATING TUBERCULOSIS

CROSS REFERENCE TO RELATED APPLICATIONS

The present application is a national stage filing of International Application No. PCT/US2011/052308, filed Sep. 20, 2011, which is entitled to priority pursuant to 35 U.S.C. §119(e) to U.S. provisional patent application No. 61/384,369, filed on Sep. 20, 2010, the disclosures of which are hereby incorporated by reference herein in their entirety.

STATEMENT REGARDING FEDERALLY SPONSORED RESEARCH OR DEVELOPMENT

This invention was made in part with United States Government support under Grant No. U01 AI075520 awarded by the National Institutes of Health. The United States Government has certain rights in the invention.

FIELD OF THE INVENTION

The present invention relates to compositions and methods for treating and preventing tuberculosis and other mycobacterial infections.

BACKGROUND

Mycobacterial infections can cause different diseases such as tuberculosis. Additionally, mycobacterial diseases can cause overwhelming, disseminated disease in immunocompromised patients. In spite of the efforts of numerous health organizations worldwide, the eradication of mycobacterial diseases has never been achieved, nor is eradication imminent.

Nearly one third of the world's population is infected with *Mycobacterium tuberculosis* complex, commonly referred to as tuberculosis, with approximately 8 million new cases, and two to three million deaths attributable to tuberculosis yearly. Tuberculosis is the cause of the largest number of human deaths attributable to a single etiologic agent. After decades of decline, tuberculosis is now on the rise. In the United States, up to 10 million individuals are believed to be infected. Almost 28,000 new cases were reported in 1990, constituting a 9.4 percent increase over 1989. A sixteen percent increase in tuberculosis cases was observed from 1985 to 1990. Overcrowded living conditions and shared air spaces are especially conducive to the spread of tuberculosis, contributing to the increase in instances that have been observed among prison inmates, and among the homeless in larger U.S. cities.

Approximately half of all patients with "Acquired Immune Deficiency Syndrome" (AIDS) will acquire a mycobacterial infection, with tuberculosis being an especially devastating complication. AIDS patients are at higher risks of developing clinical tuberculosis, and anti-tuberculosis treatment seems to be less effective than in non-AIDS patients. Consequently, the infection often progresses to a fatal disseminated disease. Mycobacteria other than *M. tuberculosis* are increasingly found in opportunistic infections that plague the AIDS patient. Organisms from the *M. avium*-intraceliulare complex (MAC), especially serotypes four and eight, account for 68% of the mycobacterial isolates from AIDS patients. Enormous numbers of MAC are found in the patients, thus, the prognosis for the infected AIDS patient is poor.

Although over 37 species of *Mycobacterium* have been identified, more than 95% of all human infections are caused by six species of mycobacteria: *M. tuberculosis, M. avium intracellulare, M. kansasii, M. fortuitum, M. chelonae*, and *M. leprae*. Cases of human tuberculosis are predominantly caused by mycobacterial species comprising *M. tuberculosis, M. bovis*, or *M. africanum*. Infection is typically initiated by the inhalation of infectious particles, which are able to reach the terminal pathways in the lungs. Following engulfment by alveolar macrophages, the bacilli are able to replicate freely, with eventual destruction of the phagocytic cells. A cascade effect ensues wherein destruction of the phagocytic cells causes additional macrophages and lymphocytes to migrate to the site of infection, where they too are ultimately eliminated.

The emergence of drug-resistant *M. tuberculosis* is an extremely disturbing phenomenon. The rate of new tuberculosis cases proven resistant to at least one standard drug has increased. Compliance with therapeutic regimens, therefore, is also a crucial component in efforts to eliminate tuberculosis and prevent the emergence of drug resistant strains. Equally important in the development of new therapeutic agents that are effective as vaccines, and as treatments, for disease caused by drug resistant strains of mycobacteria. Mycobacteria can be classified into several major groups for purpose of diagnosis and treatment: *M. tuberculosis* complex (MTBC), which can cause tuberculosis (*M. tuberculosis, M. bovis, M. africanum*, and *M. microti*); *M. leprae*, which causes Hansen's disease or leprosy; and Nontuberculous mycobacteria (NTM) are all the other mycobacteria, which can cause pulmonary disease resembling tuberculosis, lymphadenitis, skin disease, or disseminated disease. MTBC members are causative agents of human and animal tuberculosis. Species in this complex include: *M. tuberculosis*, the major cause of human tuberculosis *M. bovis, M. bovis* BCG, *M. africanum, M. canetti, M. caprae, M. microti*, and *M. pinnipedii*.

Multidrug-resistant tuberculosis (MDR-TB) is a form of tuberculosis that is resistant to two or more of the primary drugs used for the treatment of tuberculosis. Resistance to one of several forms of treatment occurs when bacteria develop the ability to withstand antibiotic attack and relay that ability to their progeny. Because an entire strain of bacteria inherit this capacity to resist the effects of various treatments, resistance can spread from one person to another.

Clearly, the possibility of drug resistant strains of tuberculosis that develop during or before treatment are a major concern to health organizations and health care practitioners. Drugs used in the treatment of tuberculosis include, but are not limited to, ethambutol (EMB), pyrazinamide (PZA), streptomycin (STR), isoniazid (INH), moxifloxacin (MOX), and rifampicin (RIF). The exact course and duration of treatment can be tailored to a specific individual, however several strategies are well known to those skilled in the art.

In 2003, the CDC reported that 7.7 percent of tuberculosis cases in the U.S. were resistant to INH, a first line drug used to treat tuberculosis. The CDC also reported that 1.3 percent of tuberculosis cases in the U.S. were resistant to both INH and RIF. RIF is the drug most commonly used with INH.

The standard treatment for tuberculosis caused by drug-sensitive organisms is a six-month regimen consisting of four drugs given for two months, followed by two drugs given for four months. The two most important drugs, given throughout the six-month course of therapy, are INH and RIF. Although the regimen is relatively simple, its administration is quite complicated. Daily ingestion of eight or nine pills is often required during the first phase of therapy; a daunting and confusing prospect. Even severely ill patients are often symptom free within a few weeks, and nearly all appear to be cured within a few months. If the treatment is not continued to completion, however, the patient may experience a relapse, and the relapse rate for patients who do not continue treatment to completion is high.

There is a long felt need in the art for new and improved antimicrobial agents. The present invention satisfies these needs.

SUMMARY OF THE INVENTION

The present invention is based on the disclosure provided herein that derivatives and analogs of nitazoxanide (NTZ) are effective against mycobacteria and therefore useful in treating tuberculosis. The present application discloses at the genus level and at the compound level chemicals which are useful in the practice of the invention.

Nitrothiazolides, represented by the FDA approved drug Nitazoxanide (Alinia), are used to treat infections caused by intestinal parasites *Giardia intestinalis* and *Cryptosporidium parvum*. The 5-nitrothiazolides also display broad and non-specific biological activity and have been reported to be inhibitory to many viruses (Hepatitis C and Influenza) and to possess anti-cancer properties. The only known target for this drug however is pyruvate ferredoxin oxidoreductase (PFOR). In vitro MIC testing of NTZ against a wide variety of anaerobic bacteria revealed excellent potency, but the pharmaco-chemical properties of the drug adversely affect its bioavailability and effectiveness for systemic use. Mechanistic studies revealed that the anionic form of the drug is biologically active and a proton abstraction mechanism has been proposed. Such a generic mechanism might account for the wide range of biological targets reported for this drug.

Mechanistic studies have shown that NTZ is a potent inhibitor of PFOR by interfering with the function of the thiamine pyrophosphate cofactor. The anion form of the drug abstracts a proton from the activated TPP complex and thereby blocks catalysis of pyruvate to acetyl CoA and $CO_2$. The protonated form of NTZ is biologically inactive. Staphylococcal species utilize pyruvate dehydrogenase and not PFOR to catalyze the oxidative decarboxylation of pyruvate. However, the chemical reactivity of NTZ might not be limited to the PFOR target as the drug has been shown to inhibit nitroreductases, protein disulfide bond isomerases and other targets.

The present invention encompasses treating mycobacterial infections, including those caused by mycobacteria such as *M. tuberculosis, M. bovis, M. bovis* BCG, *M. africanum, M. canetti, M. caprae, M. microti, M. pinnipedii, M. avium, M. avium paratuberculosis, M. avium silvaticum, M. avium "homninissuis", M. colombiense, M. asiaticum, M. gordonae, M. gastri, M. kansasii, M. hiberniae, M. nonchromogenicum, M. terrae, M. triviale, M. ulcerans, M. pseudoshottsii, M. shottsii, M. triplex, M. genavense, M. florentinum, M. lentiflavum, M. palustre, M. kubicae, M. parascrofulaceum, M. heidelbergense, M. interjectum, M. simiae, M. branderi, M. cookii, M. celatum, M. bohemicum, M. haemophilum, M. malmoense, M. szulgai, M. leprae, M. lepraemurium, M. lepromatosis, M. botniense, M. chimaera, M. conspicuum, M. doricum, M. farcinogenes, M. heckeshornense, M. intracellulare, M. lacus, M. marinum, M. monacense, M. montefiorense, M. murale, M. nebraskense, M. saskatchewanense, M. scrofulaceum, M. shimoidei, M. tusciae, M. xenopi, M. intermedium, M. abscessus, M. chelonae, M. bolletii, M. fortuitum, M. fortuitum* subsp. *acetamidolyticum, M. boenickei, M. peregrinum, M. porcinum, M. senegalense, M. septicum, M. neworleansense, M. houstonense, M. mucogenicum, M. mageritense, M. brisbanense, M. cosmeticum, M. parafortuitum, M. austroafricanum, M. diernhoferi, M. hodleri, M. neoaurum, M. frederiksbergense, M. aurum, M. vaccae, M. chitae, M. fallax, M. confluentis, M. flavescens, M. madagascariense, M. phlei, M. smnegmatis, M. goodii, M. wolinskyi, M. thermoresistibile, M. gadium, M. komossense, M. obuense, M. sphagni, M. agri, M. aichiense, M. alvei, M. arupense, M. brumae, M. canariasense, M. chubuense, M. conceptionense, M. duvalii, M. elephantis, M. gilvum, M. hassiacum, M. holsaticum, M. immunogenum, M. massiliense, M. moriokaense, M. psychrotolerans, M. pyrenivorans, M. vanbaalenii, M. pulveris, M. arosiense, M. aubagnense, M. caprae, M. chlorophenolicum, M. fluoroanthenivorans, M. kumamotonense, M. novocastrense, M. parmense, M. phocaicum, M. poriferae, M. rhodesiae, M. seoulense*, and *M. tokaiense*.

In one aspect, the *mycobacterium* is *M. tuberculosis*.

In one aspect, the *mycobacterium* is XDR or MDR.

The anion form of NTZ is the biologically active form and most of the drug is inactive below pH 6. Experiments were performed, to explore the possibility that modifications to NTZ might make it useful against bacteria, including mycobacteria. The present invention provides unexpected uses of NTZ related compounds. Various aspects and embodiments of the invention are described in further detail below.

The molecular formula of NTZ is $C_{12}H_9N_3O_5S$ and the molecular weight is 307.3. NTZ has the following structure:

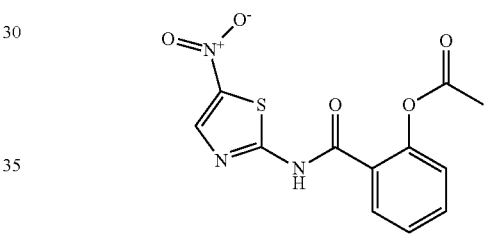

2-(acetyloxy)-N-(5-nitro-2-thiazolyl)benzamide.

Useful compounds for treating TB and other bacterial infections are provided herein.

In one embodiment, the present invention provides for treating TB and other bacterial infections with a compound of Formula (I):

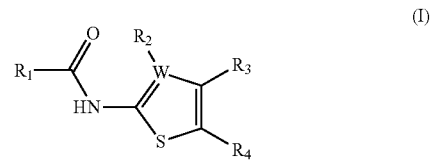

wherein:

$R_1$ and $R_3$ are each independently optional or are each independently selected from the group consisting of: H, halogen, hydroxy, acyl, alkyl, alkenyl, alkynyl, cycloalkyl, heterocyclo, aryl, heteroaryl, alkoxy, amino, amide, thiol, sulfone, sulfoxide, oxo, oxy, nitro, carbonyl, carboxy, amino acid sidechain, and amino acid (each group can be optionally substituted);

$R_2$ and $R_4$ are each independently optional or are each independently selected from the group consisting of: H, acyl, alkyl, alkenyl, alkynyl, aryl, heteroaryl, nitro, amino acid sidechain, amino acid, carbonyl, carboxy (each group can be optionally substituted); and W is selected from C, CH₂, N;

or a pharmaceutically acceptable salt or prodrug thereof.

In one aspect, optional substitution of groups includes the groups as listed for the R groups of that formula. In another aspect, the optional substitution can include optional substitution with 1, 2, 3, or 4 groups where the substituent groups are independently H, halogen, hydroxy, acyl, alkyl, alkenyl, alkynyl, cycloalkyl, heterocyclo, aryl, heteroaryl, alkoxy, amino, amide, thiol, sulfone, sulfoxide, oxo, oxy, nitro, carbonyl, carboxy, amino acid sidechain and amino acid.

In one aspect, the compound of Formula I has the structure of a compound of Formula (I) (a):

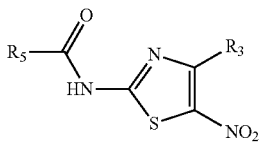

(I)(a)

wherein:

R₃ and R₅ are each independently selected from the group consisting of: H, halogen, hydroxy, acyl, alkyl, alkenyl, alkynyl, cycloalkyl, heterocyclo, aryl, heteroaryl, alkoxy, amino, amide, thiol, sulfone, sulfoxide, oxo, oxy, nitro, carbonyl, carboxy, amino acid sidechain, and amino acid (each group can be optionally substituted);

or a pharmaceutically acceptable salt or prodrug thereof.

In one aspect, the compound of Formula I has the structure of a compound of Formula (I) (b):

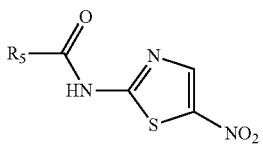

(I)(b)

wherein:

R₅ is selected from the group consisting of: H, hydroxy, acyl, alkyl, alkenyl, alkynyl, cycloalkyl, heterocyclo, aryl, heteroaryl, alkoxy, amino, amide, thiol, sulfone, sulfoxide, oxo, oxy, nitro, carbonyl, carboxy, amino acid sidechain, and amino acid;

or a pharmaceutically acceptable salt or prodrug thereof.

In one aspect, a compound of the invention has Formula (I) (c):

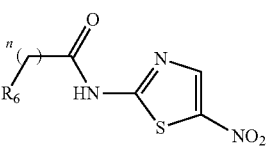

(I)(c)

wherein:

R₆ is selected from the group consisting of: H, halogen, hydroxy, acyl, alkyl, alkenyl, alkynyl, cycloalkyl, heterocyclo, aryl, heteroaryl, alkoxy, amino, amide, thiol, sulfone, sulfoxide, oxo, oxy, nitro, carbonyl, carboxy, amino acid sidechain, and amino acid (each group can be optionally substituted); and n is selected from 0 to 8;

or a pharmaceutically acceptable salt or prodrug thereof.

In another aspect, a compound of the invention has Formula (I) (d):

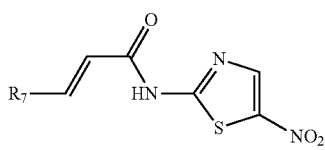

(I)(d)

wherein:

R₇ is selected from the group consisting of: H, halogen, hydroxy, acyl, alkyl, alkenyl, alkynyl, cycloalkyl, heterocyclo, aryl, heteroaryl, alkoxy, amino, amide, thiol, sulfone, sulfoxide, oxo, oxy, nitro, carbonyl, carboxy, amino acid sidechain, and amino acid (each group can be optionally substituted); and or a pharmaceutically acceptable salt or prodrug thereof.

In yet another aspect, a compound of the invention has Formula (I) (e):

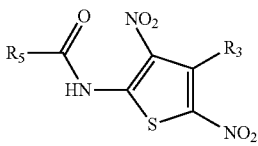

(I)(e)

wherein:

R₃ and R₅ are each independently selected from the group consisting of: H, halogen, hydroxy, acyl, alkyl, alkenyl, alkynyl, cycloalkyl, heterocyclo, aryl, heteroaryl, alkoxy, amino, amide, thiol, sulfone, sulfoxide, oxo, oxy, nitro, carbonyl, carboxy, amino acid sidechain, and amino acid (each group can be optionally substituted);

or a pharmaceutically acceptable salt or prodrug thereof.

In a further aspect, a compound of the invention has Formula (I) (f):

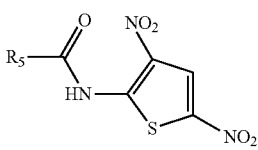

(I)(f)

wherein:

R₅ is selected from the group consisting of: H, hydroxy, acyl, alkyl, alkenyl, alkynyl, cycloalkyl, heterocyclo, aryl, heteroaryl, alkoxy, amino, amide, thiol, sulfone, sulfoxide, oxo, oxy, nitro, carbonyl, carboxy, amino acid sidechain, and amino acid;

or a pharmaceutically acceptable salt or prodrug thereof.

In another aspect, a compound of the invention has Formula (I) (g):

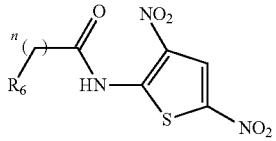

wherein:

$R_6$ is selected from the group consisting of: H, halogen, hydroxy, acyl, alkyl, alkenyl, alkynyl, cycloalkyl, heterocyclo, aryl, heteroaryl, alkoxy, amino, amide, thiol, sulfone, sulfoxide, oxo, oxy, nitro, carbonyl, carboxy, amino acid sidechain, and amino acid (each group can be optionally substituted); and n is selected from 0 to 8;

or a pharmaceutically acceptable salt or prodrug thereof.

In yet another aspect, a compound of the invention has Formula (I) (h):

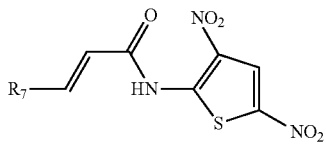

wherein:

$R_7$ is selected from the group consisting of: H, halogen, hydroxy, acyl, alkyl, alkenyl, alkynyl, cycloalkyl, heterocyclo, aryl, heteroaryl, alkoxy, amino, amide, thiol, sulfone, sulfoxide, oxo, oxy, nitro, carbonyl, carboxy, amino acid sidechain, and amino acid (each group can be optionally substituted);

or a pharmaceutically acceptable salt or prodrug thereof.

In one embodiment, the present invention provides a compound of Formula (II):

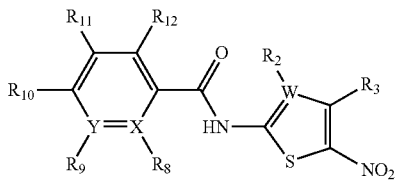

wherein:

$R_3$ and $R_8$-$R_{12}$ are each independently selected from the group consisting of: H, halogen, hydroxy, acyl, alkyl, alkenyl, alkynyl, cycloalkyl, heterocyclo, aryl, heteroaryl, alkoxy, amino, amide, thiol, sulfone, sulfoxide, oxo, oxy, nitro, carbonyl, carboxy, amino acid sidechain, amino acid and "—Z(CH$_2$)$_n$NR$_{13}$R$_{14}$" (each group can be optionally substituted) and $R_2$ is selected from the group consisting of: H, acyl, alkyl, alkenyl, alkynyl, aryl, heteroaryl, nitro, amino acid sidechain, amino acid, carbonyl, carboxy (each group can be optionally substituted); and W is selected from CH$_2$, N; and X and Y are each selected from CH and N; and Z is selected from CH$_2$, O, S, N; and n is selected from 1 to 6; and $R_{13}$ and $R_{14}$ are each independently selected from the group consisting of H, hydroxy, acyl, alkyl, alkenyl, alkynyl, cycloalkyl, heterocyclo, aryl, heteroaryl, alkoxy, amino, amide, sulfone, sulfoxide, oxo, oxy, carbonyl, carboxy, amino acid sidechain, and amino acid, and each group can be optionally substituted;

or a pharmaceutically acceptable salt or prodrug thereof.

In one aspect, a compound of Formula II has a structure of a compound of Formula (II) (a):

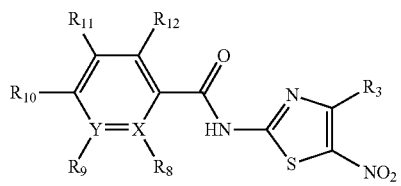

wherein:

$R_3$ and $R_8$-$R_{12}$ are each independently selected from the group consisting of: H, halogen, hydroxy, acyl, alkyl, alkenyl, alkynyl, cycloalkyl, heterocyclo, aryl, heteroaryl, alkoxy, amino, amide, thiol, sulfone, sulfoxide, oxo, oxy, nitro, carbonyl, carboxy, amino acid sidechain, amino acid and "—Z(CH$_2$)$_n$NR$_{13}$R$_{14}$" (each group can be optionally substituted);

X and Y are each selected from CH and N;

Z is selected from CH$_2$, O, S, N;

n is selected from 1 to 6; and $R_{13}$ and $R_{14}$ are each independently selected from the group consisting of H, hydroxy, acyl, alkyl, alkenyl, alkynyl, cycloalkyl, heterocyclo, aryl, heteroaryl, alkoxy, amino, amide, sulfone, sulfoxide, oxo, oxy, carbonyl, carboxy, amino acid sidechain, and amino acid, and each group can be optionally substituted;

or a pharmaceutically acceptable salt or prodrug thereof.

In one aspect, a compound of the invention comprises a structure of Formula (II) (b):

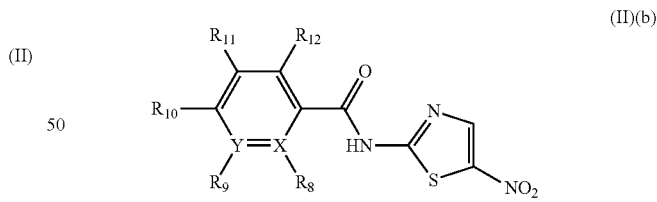

wherein:

$R_8$-$R_{12}$ are each independently selected from the group consisting of: H, halogen, hydroxy, acyl, alkyl, alkenyl, alkynyl, cycloalkyl, heterocyclo, aryl, heteroaryl, alkoxy, amino, amide, thiol, sulfone, sulfoxide, oxo, oxy, nitro, carbonyl, carboxy, amino acid sidechain, amino acid and "—Z(CH$_2$)$_n$NR$_{13}$R$_{14}$" (each group can be optionally substituted);

X and Y are each selected from CH and N;

Z is selected from CH$_2$, O, S, N;

n is selected from 1 to 6; and $R_{13}$ and $R_{14}$ are each independently selected from the group consisting of H, hydroxy, acyl, alkyl, alkenyl, alkynyl, cycloalkyl, heterocyclo, aryl, heteroaryl, alkoxy, amino, amide, sulfone, sulfoxide, oxo, oxy, carbonyl, carboxy, amino acid sidechain, and amino acid, and each group can be optionally substituted;

or a pharmaceutically acceptable salt or prodrug thereof.

In another aspect, the invention provides a compound of Formula (II) (c):

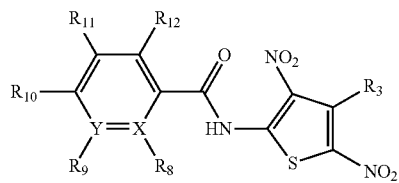

(II)(c)

wherein:

$R_3$ and $R_8$-$R_{12}$ are each independently selected from the group consisting of: H, halogen, hydroxy, acyl, alkyl, alkenyl, alkynyl, cycloalkyl, heterocyclo, aryl, heteroaryl, alkoxy, amino, amide, thiol, sulfone, sulfoxide, oxo, oxy, nitro, carbonyl, carboxy, amino acid sidechain, amino acid and "—Z(CH$_2$)$_n$NR$_{13}$R$_{14}$" (each group can be optionally substituted);

X and Y are each selected from CH and N;

Z is selected from CH$_2$, O, S, N;

n is selected from 1 to 6; and $R_{13}$ and $R_{14}$ are each independently selected from the group consisting of H, hydroxy, acyl, alkyl, alkenyl, alkynyl, cycloalkyl, heterocyclo, aryl, heteroaryl, alkoxy, amino, amide, sulfone, sulfoxide, oxo, oxy, carbonyl, carboxy, amino acid sidechain, and amino acid, and each group can be optionally substituted;

or a pharmaceutically acceptable salt or prodrug thereof.

In yet another aspect, the invention provides a compound of Formula (II) (d):

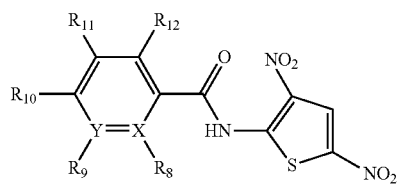

(II)(d)

wherein:

$R_8$-$R_{12}$ are each independently selected from the group consisting of: H, halogen, hydroxy, acyl, alkyl, alkenyl, alkynyl, cycloalkyl, heterocyclo, aryl, heteroaryl, alkoxy, amino, amide, thiol, sulfone, sulfoxide, oxo, oxy, nitro, carbonyl, carboxy, amino acid sidechain, amino acid and "—Z(CH$_2$)$_n$NR$_{13}$R$_{14}$" (each group can be optionally substituted);

X and Y are each selected from CH and N;

Z is selected from CH$_2$, O, S, N;

n is selected from 1 to 6; and $R_{13}$ and $R_{14}$ are each independently selected from the group consisting of H, hydroxy, acyl, alkyl, alkenyl, alkynyl, cycloalkyl, heterocyclo, aryl, heteroaryl, alkoxy, amino, amide, sulfone, sulfoxide, oxo, oxy, carbonyl, carboxy, amino acid sidechain, and amino acid, and wherein each group can be optionally substituted;

or a pharmaceutically acceptable salt or prodrug thereof.

In one embodiment, the invention provides a compound of Formula (III):

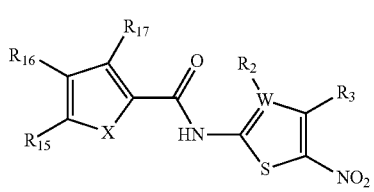

(III)

wherein:

$R_3$ and $R_{15}$-$R_{17}$ are each independently selected from the group consisting of: H, halogen, hydroxy, acyl, alkyl, alkenyl, alkynyl, cycloalkyl, heterocyclo, aryl, heteroaryl, alkoxy, amino, amide, thiol, sulfone, sulfoxide, oxo, oxy, nitro, carbonyl, carboxy, amino acid sidechain, amino acid "—Z (CH$_2$)$_n$ NR$_{13}$R$_{14}$" (each group can be optionally substituted);

$R_2$ is selected from the group consisting of: H, acyl, alkyl, alkenyl, alkynyl, aryl, heteroaryl, nitro, amino acid sidechain, amino acid, carbonyl, and carboxy, wherein each group can be optionally substituted;

W is selected from CH$_2$, N;

X is selected from O, S, NH and NCH$_3$;

Z is selected from CH$_2$, O, S, N;

n is selected from 1 to 6; and $R_{13}$ and $R_{14}$ are each independently selected from the group consisting of H, hydroxy, acyl, alkyl, alkenyl, alkynyl, cycloalkyl, heterocyclo, aryl, heteroaryl, alkoxy, amino, amide, sulfone, sulfoxide, oxo, oxy, carbonyl, carboxy, amino acid sidechain, and amino acid, wherein each group can be optionally substituted;

or a pharmaceutically acceptable salt or prodrug thereof.

In one aspect, a compound of Formula (III) has a structure of a compound of Formula (III) (a):

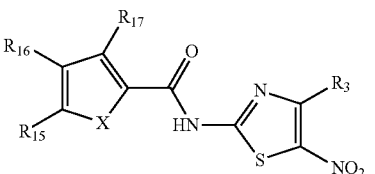

(III)(a)

wherein:

$R_3$ and $R_{15}$-$R_{17}$ are each independently selected from the group consisting of: H, halogen, hydroxy, acyl, alkyl, alkenyl, alkynyl, cycloalkyl, heterocyclo, aryl, heteroaryl, alkoxy, amino, amide, thiol, sulfone, sulfoxide, oxo, oxy, nitro, carbonyl, carboxy, amino acid sidechain, amino acid "—Z (CH$_2$)$_n$ NR$_{13}$R$_{14}$", wherein each group can be optionally substituted;

X is selected from O, S, NH and NCH$_3$;

Z is selected from CH$_2$, O, S, N;

n is selected from 1 to 6; and $R_{13}$ and $R_{14}$ are each independently selected from the group consisting of H, hydroxy, acyl, alkyl, alkenyl, alkynyl, cycloalkyl, heterocyclo, aryl, heteroaryl, alkoxy, amino, amide, sulfone, sulfoxide, oxo, oxy, carbonyl, carboxy, amino acid sidechain, and amino acid, wherein each group can be optionally substituted;

or a pharmaceutically acceptable salt or prodrug thereof.

In another aspect, the invention provides a compound of Formula (III) (b):

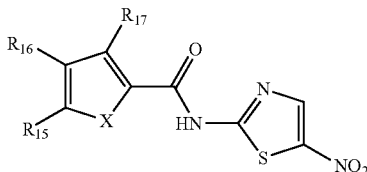

(III)(b)

wherein:

$R_{15}$-$R_{17}$ are each independently selected from the group consisting of: H, halogen, hydroxy, acyl, alkyl, alkenyl, alkynyl, cycloalkyl, heterocyclo, aryl, heteroaryl, alkoxy, amino, amide, thiol, sulfone, sulfoxide, oxo, oxy, nitro, carbonyl, carboxy, amino acid sidechain, amino acid "—Z(CH$_2$)$_n$NR$_{13}$R$_{14}$", wherein each group can be optionally substituted;

X is selected from O, S, NH and NCH$_3$;

Z is selected from CH$_2$, O, S, N;

n is selected from 1 to 6; and $R_{13}$ and $R_{14}$ are each independently selected from the group consisting of H, hydroxy, acyl, alkyl, alkenyl, alkynyl, cycloalkyl, heterocyclo, aryl, heteroaryl, alkoxy, amino, amide, sulfone, sulfoxide, oxo, oxy, carbonyl, carboxy, amino acid sidechain, and amino acid, wherein each group can be optionally substituted;

or a pharmaceutically acceptable salt or prodrug thereof.

In yet another aspect, the invention provides a compound of Formula (III) (c):

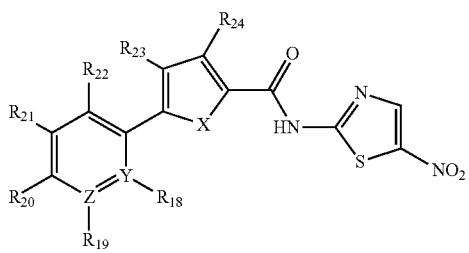

(III)(c)

wherein:

$R_{18}$-$R_{24}$ are each independently selected from the group consisting of: H, halogen, hydroxy, acyl, alkyl, alkenyl, alkynyl, cycloalkyl, heterocyclo, aryl, heteroaryl, alkoxy, amino, amide, thiol, sulfone, sulfoxide, oxo, oxy, nitro, carbonyl, carboxy, amino acid sidechain, and amino acid, wherein each group can be optionally substituted;

X is selected from O, S, NH and NCH$_3$; and

Y and Z are each independently selected from CH and N;

or a pharmaceutically acceptable salt or prodrug thereof.

In yet another aspect, the invention provides a compound of Formula (III) (d):

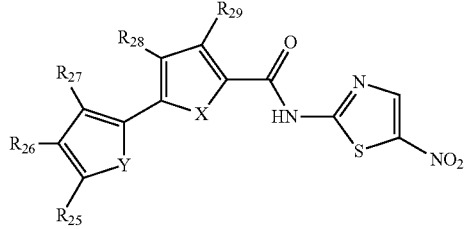

(III)(d)

wherein:

$R_{25}$-$R_{29}$ are each independently selected from the group consisting of: H, halogen, hydroxy, acyl, alkyl, alkenyl, alkynyl, cycloalkyl, heterocyclo, aryl, heteroaryl, alkoxy, amino, amide, thiol, sulfone, sulfoxide, oxo, oxy, nitro, carbonyl, carboxy, amino acid sidechain, and amino acid, wherein each group can be optionally substituted; and X and Y are each independently selected from O, S, NH and NCH$_3$;

or a pharmaceutically acceptable salt or prodrug thereof.

In a further aspect, the invention provides a compound of Formula (III) (e):

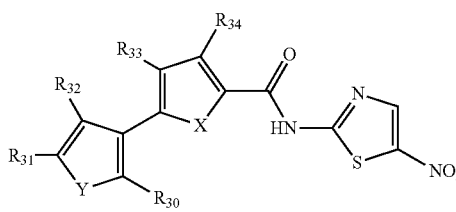

(III)(e)

wherein:

$R_{30}$-$R_{34}$ are each independently selected from the group consisting of: H, halogen, hydroxy, acyl, alkyl, alkenyl, alkynyl, cycloalkyl, heterocyclo, aryl, heteroaryl, alkoxy, amino, amide, thiol, sulfone, sulfoxide, oxo, oxy, nitro, carbonyl, carboxy, amino acid sidechain, and amino acid, wherein each group can be optionally substituted; and X and Y are each independently selected from O, S, NH and NCH$_3$;

or a pharmaceutically acceptable salt or prodrug thereof.

In yet another aspect, the invention provides a compound of Formula (III) (f):

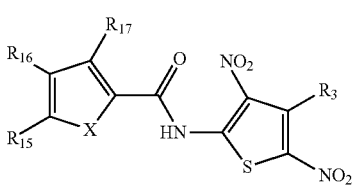

(III)(f)

wherein:

$R_3$ and $R_{15}$-$R_{17}$ are each independently selected from the group consisting of: H, halogen, hydroxy, acyl, alkyl, alkenyl, alkynyl, cycloalkyl, heterocyclo, aryl, heteroaryl, alkoxy, amino, amide, thiol, sulfone, sulfoxide, oxo, oxy, nitro, carbonyl, carboxy, amino acid sidechain, and amino acid "—Z(CH$_2$)$_n$NR$_{13}$R$_{14}$", wherein each group can be optionally substituted;

X is selected from O, S, NH and NCH$_3$;

Z is selected from CH$_2$, O, S, N;

n is selected from 1 to 6; and $R_{13}$ and $R_{14}$ are each independently selected from the group consisting of H, hydroxy, acyl, alkyl, alkenyl, alkynyl, cycloalkyl, heterocyclo, aryl, heteroaryl, alkoxy, amino, amide, sulfone, sulfoxide, oxo, oxy, carbonyl, carboxy, amino acid sidechain, and amino acid, wherein each group can be optionally substituted;

or a pharmaceutically acceptable salt or prodrug thereof.

In another aspect, the invention provides a compound of Formula (III) (g):

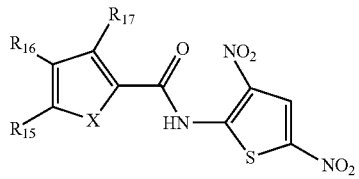

(III)(g)

wherein:

R$_{15}$-R$_{17}$ are each independently selected from the group consisting of: H, halogen, hydroxy, acyl, alkyl, alkenyl, alkynyl, cycloalkyl, heterocyclo, aryl, heteroaryl, alkoxy, amino, amide, thiol, sulfone, sulfoxide, oxo, oxy, nitro, carbonyl, carboxy, amino acid sidechain, and amino acid "—Z(CH$_2$)$_n$NR$_{13}$R$_{14}$", wherein each group can be optionally substituted;

X is selected from O, S, NH and NCH$_3$;

Z is selected from CH$_2$, O, S, N;

n is selected from 1 to 6; and

R$_{13}$ and R$_{14}$ are each independently selected from the group consisting of H, hydroxy, acyl, alkyl, alkenyl, alkynyl, cycloalkyl, heterocyclo, aryl, heteroaryl, alkoxy, amino, amide, sulfone, sulfoxide, oxo, oxy, carbonyl, carboxy, amino acid sidechain, and amino acid, wherein each group can be optionally substituted;

or a pharmaceutically acceptable salt or prodrug thereof.

In another aspect, the invention provides a compound of Formula (III) (h):

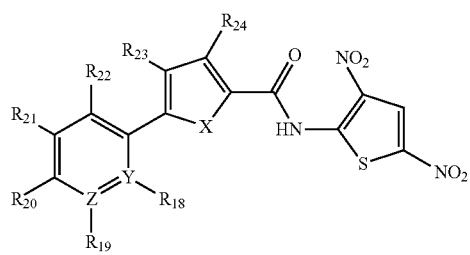

(III)(h)

wherein:

R$_{18}$-R$_{24}$ are each independently selected from the group consisting of: H, halogen, hydroxy, acyl, alkyl, alkenyl, alkynyl, cycloalkyl, heterocyclo, aryl, heteroaryl, alkoxy, amino, amide, thiol, sulfone, sulfoxide, oxo, oxy, nitro, carbonyl, carboxy, amino acid sidechain, and amino acid, wherein each group can be optionally substituted;

X is selected from O, S, NH and NCH$_3$; and

Y and Z are each selected from CH and N;

or a pharmaceutically acceptable salt or prodrug thereof.

In yet another aspect, the invention provides a compound of Formula (III) (i):

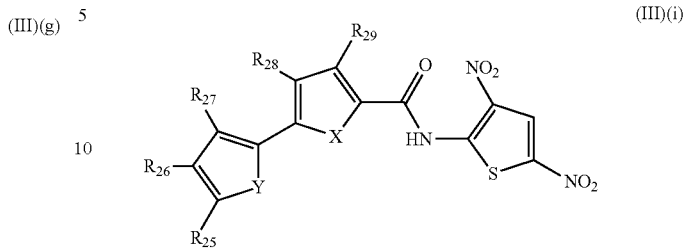

(III)(i)

wherein:

R$_{25}$-R$_{29}$ are each independently selected from the group consisting of: H, halogen, hydroxy, acyl, alkyl, alkenyl, alkynyl, cycloalkyl, heterocyclo, aryl, heteroaryl, alkoxy, amino, amide, thiol, sulfone, sulfoxide, oxo, oxy, nitro, carbonyl, carboxy, amino acid sidechain, and amino acid, wherein each group can be optionally substituted; and X and Y are each independently selected from O, S, NH and NCH$_3$;

or a pharmaceutically acceptable salt or prodrug thereof.

In a further aspect, the invention provides a compound of Formula (III) (j):

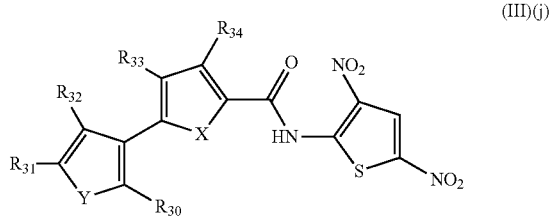

(III)(j)

wherein:

R$_{30}$-R$_{34}$ are each independently selected from the group consisting of: H, halogen, hydroxy, acyl, alkyl, alkenyl, alkynyl, cycloalkyl, heterocyclo, aryl, heteroaryl, alkoxy, amino, amide, thiol, sulfone, sulfoxide, oxo, oxy, nitro, carbonyl, carboxy, amino acid sidechain, and amino acid, wherein each group can be optionally substituted; and X and Y are each independently selected from O, S, NH and NCH$_3$;

or a pharmaceutically acceptable salt or prodrug thereof.

In one embodiment, the invention provides a compound of Formula (IV):

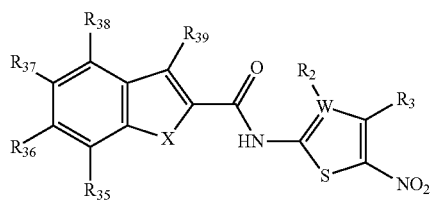

(IV)

wherein:

R$_3$ and R$_{35}$-R$_{39}$ are each independently selected from the group consisting of: H, halogen, hydroxy, acyl, alkyl, alkenyl, alkynyl, cycloalkyl, heterocyclo, aryl, heteroaryl, alkoxy, amino, amide, thiol, sulfone, sulfoxide, oxo, oxy, nitro, carbonyl, carboxy, amino acid sidechain, and amino acid, wherein each group can be optionally substituted, and $R_2$ is selected from the group consisting of: H, acyl, alkyl, alkenyl, alkynyl, aryl, heteroaryl, nitro, amino acid sidechain, amino acid, carbonyl, and carboxy, wherein each group can be optionally substituted;

W is selected from $CH_2$, and N; and

X is selected from O, S, NH and $NCH_3$;

or a pharmaceutically acceptable salt or prodrug thereof.

In one aspect, a compound of Formula IV comprises a compound of Formula (IV) (a):

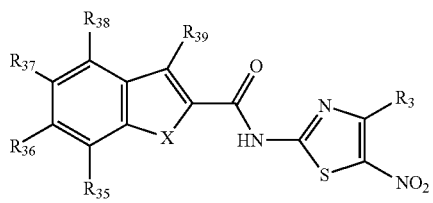

(IV)(a)

wherein:

$R_3$ and $R_{35}$-$R_{39}$ are each independently selected from the group consisting of: H, halogen, hydroxy, acyl, alkyl, alkenyl, alkynyl, cycloalkyl, heterocyclo, aryl, heteroaryl, alkoxy, amino, amide, thiol, sulfone, sulfoxide, oxo, oxy, nitro, carbonyl, carboxy, amino acid sidechain, and amino acid, wherein each group can be optionally substituted; and X is selected from O, S, NH and $NCH_3$.

or a pharmaceutically acceptable salt or prodrug thereof.

In another aspect, the invention provides a compound of Formula (IV) (b):

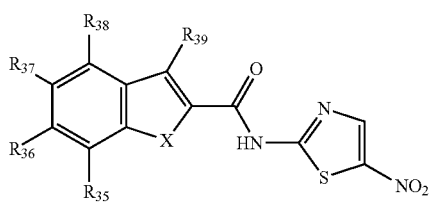

(IV)(b)

wherein:

$R_{35}$-$R_{39}$ are each independently selected from the group consisting of: H, halogen, hydroxy, acyl, alkyl, alkenyl, alkynyl, cycloalkyl, heterocyclo, aryl, heteroaryl, alkoxy, amino, amide, thiol, sulfone, sulfoxide, oxo, oxy, nitro, carbonyl, carboxy, amino acid sidechain, and amino acid, wherein each group can be optionally substituted; and X is selected from O, S, NH and $NCH_3$;

or a pharmaceutically acceptable salt or prodrug thereof.

In a further aspect, the invention provides a compound of Formula (IV) (c):

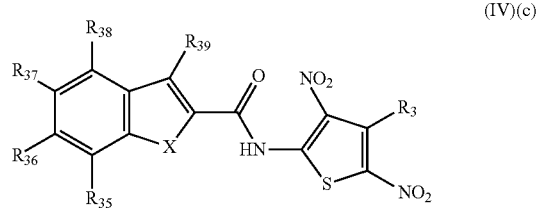

(IV)(c)

wherein:

$R_3$ and $R_{35}$-$R_{39}$ are each independently selected from the group consisting of: H, halogen, hydroxy, acyl, alkyl, alkenyl, alkynyl, cycloalkyl, heterocyclo, aryl, heteroaryl, alkoxy, amino, amide, thiol, sulfone, sulfoxide, oxo, oxy, nitro, carbonyl, carboxy, amino acid sidechain, and amino acid, wherein each group can be optionally substituted; and X is selected from O, S, NH and $NCH_3$;

or a pharmaceutically acceptable salt or prodrug thereof.

In yet a further aspect, the invention provides a compound of Formula (IV) (d):

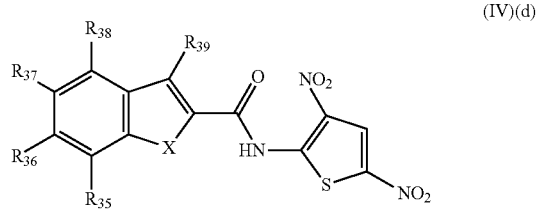

(IV)(d)

wherein:

$R_{35}$-$R_{39}$ are each independently selected from the group consisting of: H, halogen, hydroxy, acyl, alkyl, alkenyl, alkynyl, cycloalkyl, heterocyclo, aryl, heteroaryl, alkoxy, amino, amide, thiol, sulfone, sulfoxide, oxo, oxy, nitro, carbonyl, carboxy, amino acid sidechain, and amino acid, wherein each group can be optionally substituted; and X is selected from O, S, NH and $NCH_3$;

or a pharmaceutically acceptable salt or prodrug thereof.

In one embodiment, the present invention provides a compound of Formula (V):

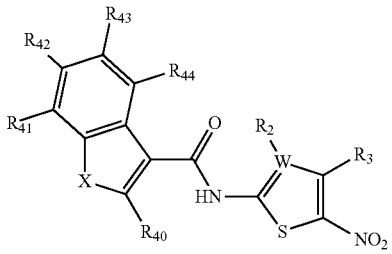

(V)

wherein:

$R_3$ and $R_{40}$-$R_{44}$ are each independently selected from the group consisting of: H, halogen, hydroxy, acyl, alkyl, alkenyl, alkynyl, cycloalkyl, heterocyclo, aryl, heteroaryl, alkoxy, amino, amide, thiol, sulfone, sulfoxide, oxo, oxy, nitro, carbonyl, carboxy, amino acid sidechain, and amino acid, wherein each group can be optionally substituted, and $R_2$ is selected from the group consisting of: H, acyl, alkyl, alkenyl, alkynyl, aryl, heteroaryl, nitro, amino acid sidechain, amino acid, carbonyl, and carboxy, wherein each group can be optionally substituted;

W is selected from CH$_2$, and N; and

X is selected from O, S, NH and NCH$_3$;

or a pharmaceutically acceptable salt or prodrug thereof.

In one aspect, a compound of Formula V comprises a compound of Formula (V) (a):

(V)(a)

wherein:

R$_3$ and R$_{40}$-R$_{44}$ are each independently selected from the group consisting of: H, halogen, hydroxy, acyl, alkyl, alkenyl, alkynyl, cycloalkyl, heterocyclo, aryl, heteroaryl, alkoxy, amino, amide, thiol, sulfone, sulfoxide, oxo, oxy, nitro, carbonyl, carboxy, amino acid sidechain, and amino acid, wherein each group can be optionally substituted; and X is selected from O, S, NH and NCH$_3$;

or a pharmaceutically acceptable salt or prodrug thereof.

In a further aspect, the invention provides a compound of Formula (V) (b):

(V)(b)

wherein:

R$_{40}$-R$_{44}$ are each independently selected from the group consisting of: H, halogen, hydroxy, acyl, alkyl, alkenyl, alkynyl, cycloalkyl, heterocyclo, aryl, heteroaryl, alkoxy, amino, amide, thiol, sulfone, sulfoxide, oxo, oxy, nitro, carbonyl, carboxy, amino acid sidechain, and amino acid, wherein each group can be optionally substituted; and X is selected from O, S, NH and NCH$_3$;

or a pharmaceutically acceptable salt or prodrug thereof.

In a further aspect, the invention provides a compound of Formula (V) (c):

(V)(c)

wherein:

R$_3$ and R$_{40}$-R$_{44}$ are each independently selected from the group consisting of: H, halogen, hydroxy, acyl, alkyl, alkenyl, alkynyl, cycloalkyl, heterocyclo, aryl, heteroaryl, alkoxy, amino, amide, thiol, sulfone, sulfoxide, oxo, oxy, nitro, carbonyl, carboxy, amino acid sidechain, and amino acid, wherein each group can be optionally substituted; and X is selected from O, S, NH and NCH$_3$;

or a pharmaceutically acceptable salt or prodrug thereof.

In another aspect, the invention provides a compound of Formula (V) (d):

(V)(d)

wherein:

R$_{40}$-R$_{44}$ are each independently selected from the group consisting of: H, halogen, hydroxy, acyl, alkyl, alkenyl, alkynyl, cycloalkyl, heterocyclo, aryl, heteroaryl, alkoxy, amino, amide, thiol, sulfone, sulfoxide, oxo, oxy, nitro, carbonyl, carboxy, amino acid sidechain, and amino acid, wherein each group can be optionally substituted; and X is selected from O, S, NH and NCH$_3$;

or a pharmaceutically acceptable salt or prodrug thereof.

In one embodiment, the invention provides a compound of Formula (VI):

(VI)

wherein:

R$_3$ and R$_{45}$-R$_{47}$ are each independently selected from the group consisting of: H, halogen, hydroxy, acyl, alkyl, alkenyl, alkynyl, cycloalkyl, heterocyclo, aryl, heteroaryl, alkoxy, amino, amide, thiol, sulfone, sulfoxide, oxo, oxy, nitro, carbonyl, carboxy, amino acid sidechain, and amino acid (each group can be optionally substituted) and R$_2$ is selected from the group consisting of: H, acyl, alkyl, alkenyl, alkynyl, aryl, heteroaryl, nitro, amino acid sidechain, amino acid, carbonyl, and carboxy, wherein each group can be optionally substituted;

W is selected from CH$_2$, and N;

n is selected from 0 to 2;

or a pharmaceutically acceptable salt or prodrug thereof.

In one aspect, a compound of Formula VI comprise a compound of Formula (VI) (a):

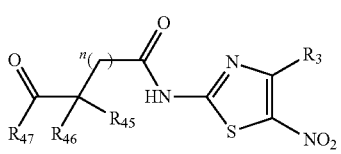

wherein:

$R_3$ and $R_{45}$-$R_{47}$ are each independently selected from the group consisting of: H, halogen, hydroxy, acyl, alkyl, alkenyl, alkynyl, cycloalkyl, heterocyclo, aryl, heteroaryl, alkoxy, amino, amide, thiol, sulfone, sulfoxide, oxo, oxy, nitro, carbonyl, carboxy, amino acid sidechain, and amino acid, wherein each group can be optionally substituted; and n is selected from 0 to 2;

or a pharmaceutically acceptable salt or prodrug thereof.

In yet another aspect, the invention provides a compound of Formula (VI) (b):

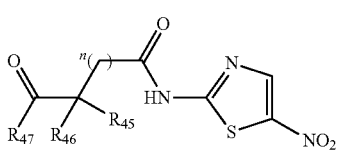

wherein:

$R_{45}$-$R_{47}$ are each independently selected from the group consisting of: H, halogen, hydroxy, acyl, alkyl, alkenyl, alkynyl, cycloalkyl, heterocyclo, aryl, heteroaryl, alkoxy, amino, amide, thiol, sulfone, sulfoxide, oxo, oxy, nitro, carbonyl, carboxy, amino acid sidechain, and amino acid, wherein each group can be optionally substituted; and n is selected from 0 to 2;

or a pharmaceutically acceptable salt or prodrug thereof.

In a further aspect, the invention provides a compound of Formula (VI) (c):

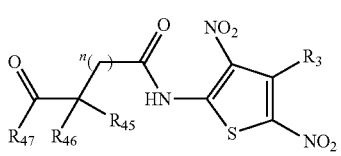

wherein:

$R_3$ and $R_{45}$-$R_{47}$ are each independently selected from the group consisting of: H, halogen, hydroxy, acyl, alkyl, alkenyl, alkynyl, cycloalkyl, heterocyclo, aryl, heteroaryl, alkoxy, amino, amide, thiol, sulfone, sulfoxide, oxo, oxy, nitro, carbonyl, carboxy, amino acid sidechain, and amino acid, wherein each group can be optionally substituted; and n is selected from 0 to 2;

or a pharmaceutically acceptable salt or prodrug thereof.

In yet another aspect, the invention provides a compound of Formula (VI) (d):

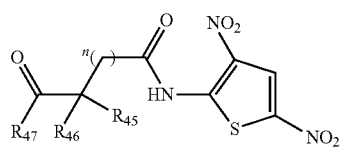

wherein:

$R_{45}$-$R_{47}$ are each independently selected from the group consisting of: H, halogen, hydroxy, acyl, alkyl, alkenyl, alkynyl, cycloalkyl, heterocyclo, aryl, heteroaryl, alkoxy, amino, amide, thiol, sulfone, sulfoxide, oxo, oxy, nitro, carbonyl, carboxy, amino acid sidechain, and amino acid (each group can be optionally substituted); and n is selected from 0 to 2;

or a pharmaceutically acceptable salt or prodrug thereof.

For all compounds of the invention, in one aspect, optional substitution of groups includes the groups as listed for the R groups of that formula. In another aspect, the optional substitution can include optional substitution with 1, 2, 3, or 4 groups where the substituent groups are independently H, halogen, hydroxy, acyl, alkyl, alkenyl, alkynyl, cycloalkyl, heterocyclo, aryl, heteroaryl, alkoxy, amino, amide, thiol, sulfone, sulfoxide, oxo, oxy, nitro, carbonyl, carboxy, amino acid sidechain and amino acid.

In one aspect, the present invention provides compositions which include, but are not limited to, aliphatic derivatives of 2-amino-5-nitrothiazole, aliphatic amine analogues of 2-amino-5-nitrothiazole, amino acid analogues of 2-amino-5-nitrothiazole, anthranilic analogues of 2-amino-5-nitrothiazole, pyridine analogues of 2-amino-5-nitrothiazole, indole analogues of 2-amino-5-nitrothiazole, carboxylic acid analogues of 2-amino-5-nitrothiazole, dimer-like analogues of 2-amino-5-nitrothiazole, halide analogues of 2-amino-5-nitrothiazole, monosubstituted analogues of 2-amino-5-nitrothiazole, disubstituted analogues of 2-amino-5-nitrothiazole, furan analogues of 2-amino-5-nitrothiazole, thiophene analogues of 2-amino-5-nitrothiazole, amide isosteres of 2-amino-5-nitrothiazole, analogues of 2-amino-4-chloro-5-nitrothiazole, and analogues of 2-amino-3,5-dinitrothiophene, and derivatives and analogues thereof.

In one aspect, useful anti-tuberculosis compounds of the invention include, but are not limited to, the following compounds: VPC161180, VPC161183, VPC162047, VPC162080, VPC162087, VPC162088, VPC16a1011, VPC16a1060, VPC16b1089, VPC16b1090, VPC16b1092, VPC16b1093, VPC161181, and VPC16b1094. The compounds have the structures:

VPC161180

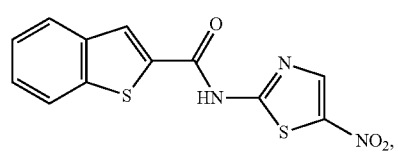

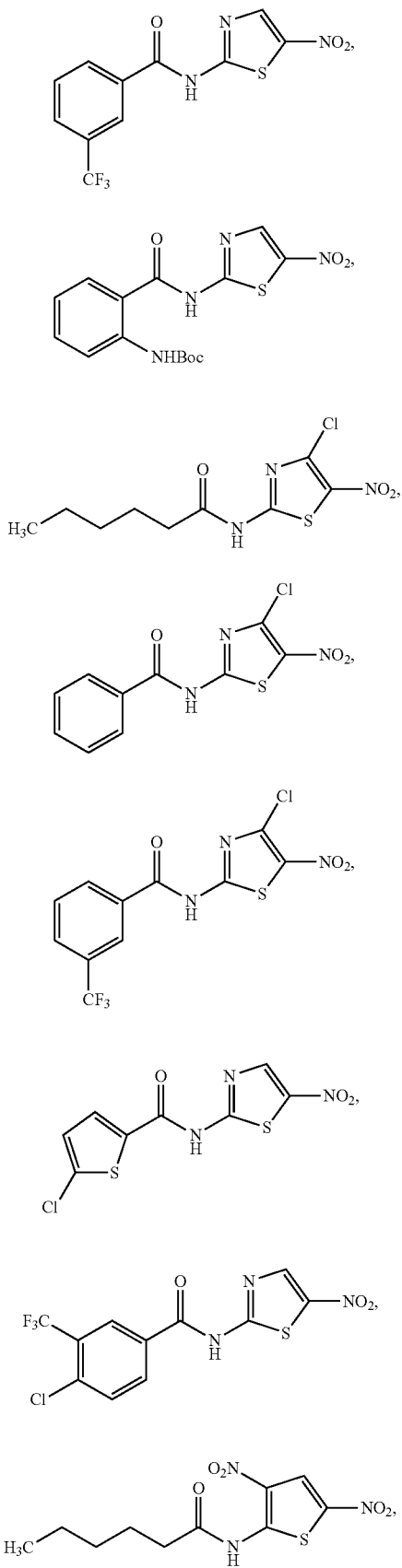
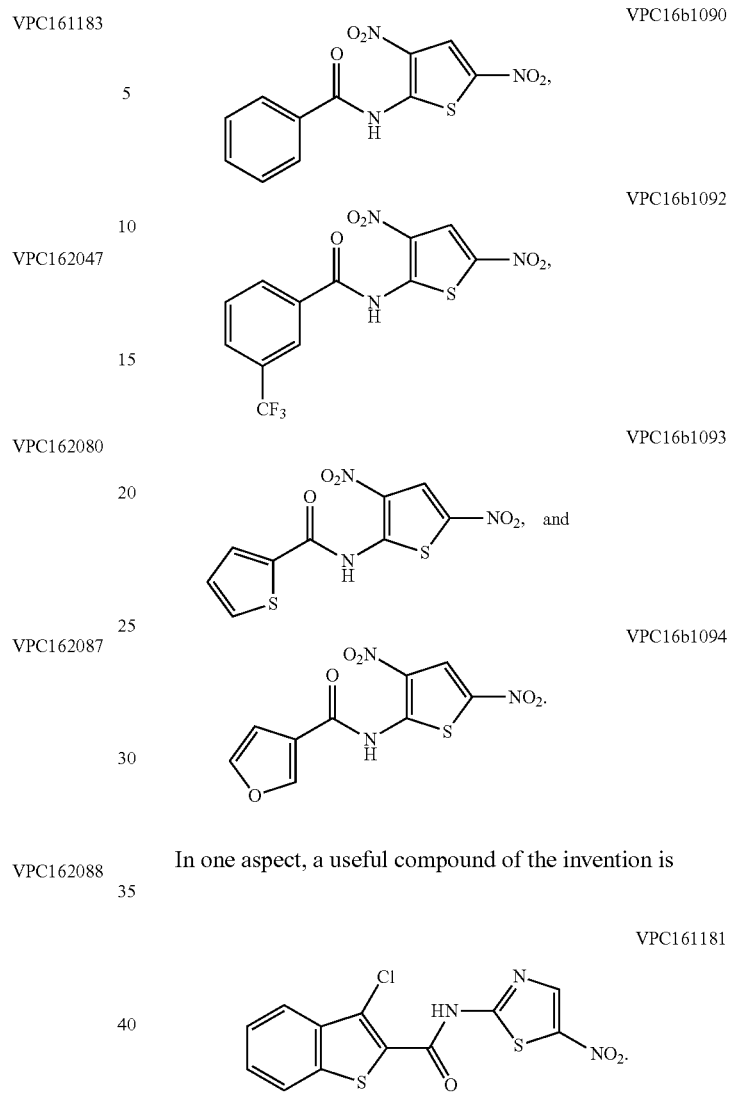

In one aspect, a useful compound of the invention is

The present invention further provides pharmaceutical compositions comprising at least one compound of the invention. The pharmaceutical compositions are useful, for example, for preventing or treating infections as described herein by administering a pharmaceutical composition comprising an effective amount of at least one compound of the invention. Additional therapeutic agents can be added to the pharmaceutical compositions or used in conjunction with the treatments using the compounds of the invention. Additional therapeutic agents include, for example, NTZ, TIZ, and AMIX. Other known drugs can also be used in combination therapy with the compounds of the invention. Drugs used in the treatment of tuberculosis include, but are not limited to, ethambutol (EMB), pyrazinamide (PZA), streptomycin (STR), isoniazid (INH), moxifloxacin (MOX), and rifampicin (RIF) and one or more of these drugs can be used in combination with at least one compound of the invention to treat a mycobacterial infection.

Compounds useful for treating TB and other infections as disclosed herein include compounds described herein and in International Patent Publication Number WO 2010/107736 (Hoffman et al.) published Sep. 23, 2010 (Int. App. No. PCT/US2010027397), incorporated by reference in its entirety herein. In one embodiment, compounds useful for treating or preventing mycobacterial infections include those encompassed by formulas I, Ia, Ib, Ic, Id, Ie, If, Ig, Ih, II, IIa, IIb, IIc, IId, III, IIIa, IIIb, IIIc, IIId, IIIe, IIIf, IIIg, IIIh, IIIi, IIIj, IV, IVa, IVb, IVc, IVd, V, Va, Vb, Vc, Vd, VI, VIa, VIb, VIc, and VId. In one aspect, useful compounds include, for example, compounds VPC161180, VPC161183, VPC162047, VPC162080, VPC162087, VPC162088, VPC16a1011, VPC16a1060, VPC16b1089, VPC16b1090, VPC16b1092, VPC16b1093, and VPCb1094.

In one aspect, useful compounds of the invention disclosed herein are di-nitro-thiophene or 4-chloro-5-nitro-thiazole derivatives of nitazoxanide.

For example, support for the use and synthesis of VPC161180, also referred to as 161180, can be also found in International Patent Publication Number WO 2010/107736 (Hoffman et al.) published Sep. 23, 2010 (Int. App. No. PCT/US2010027397), for example, at the table at page 140 for Thiophene Analogues of 2-amino-5-nitrothiazole; for VPC161183 at page 102, and FIG. 24; for VPC162047 at page 97, the table at page 121 on Anthranilic Analogues of 2-amino-5-nitrothiazole, and FIG. 18; for VPC162080 the table at page 146 for Analogues of 2-amino-4-chloro-5-nitrothiazole; for VPC162087 the table at page 146 for Analogues of 2-amino-4-chloro-5-nitrothiazole; for VPC162088 the table at page 146 for Analogues of 2-amino-4-chloro-5-nitrothiazole; for VPC16a1011 at page 30, page 106, the table at page 140 for Thiophene Analogues of 2-amino-5-nitrothiazole, and FIG. 27B; for VPC16a1060 at page 29, page 103, the table at page 135 on Disubstituted Analogues of 2-amino-5-nitrothiazole, and FIG. 25; for VPC16b1089 the table at page 148 on Analogues of 2-amino-3,5-dinitrothiophene; for VPC16b1090 the table at page 148 on Analogues of 2-amino-3,5-dinitrothiophene; VPC16b1092 the table at page 149 on Analogues of 2-amino-3,5-dinitrothiophene; for VPC16b1093 at page 30, page 108, the table at page 149 on Analogues of 2-amino-3,5-dinitrothiophene and FIG. 30A; and for VPC16b1094 the table at page 149 on Analogues of 2-amino-3,5-dinitrothiophene. Therefore, the useful derivatives and analogues of nitazoxanide of the invention include, but are not limited to, Anthranilic Analogues of 2-amino-5-nitrothiazole, Disubstituted Analogues of 2-amino-5-nitrothiazole, Thiophene Analogues of 2-amino-5-nitrothiazole, Analogues of 2-amino-4-chloro-5-nitrothiazole, and Analogues of 2-amino-3,5-dinitrothiophene.

In one embodiment, compounds of the invention are useful for killing the microorganisms described herein. In one aspect, the compounds of the invention kill mycobacteria.

The compounds of the present invention are useful for targeting microorganisms other than just the ones described in the Examples.

In a further aspect, compounds of the invention are bactericidal against Gram positive bacteria and Mycobacteria, including *M. tuberculosis*.

In one aspect, antimicrobial agents of the invention that inhibit assembly or function of fimbrial filaments are useful for preventing and treating infection.

In one aspect, other compounds or therapeutics such as NTZ, TIZ, AMIX, EMB, PZA, STR, INH, MOX, and RIF can be used in conjunction with the compounds of the invention.

In one aspect, bacteria susceptible to compounds of the invention include, but are not limited to, *Mycobacterium* species.

The present invention is also useful for preventing and treating infections comprising administering a pharmaceutical composition comprising an effective amount of at least one useful compound of the invention, optionally an additional therapeutic agent, and a pharmaceutically-acceptable carrier.

The compounds of the invention can be administered or used with other drugs and antimicrobial agents and additional therapeutic agents.

The present invention further provides kits. Kits of the invention comprise at least one compound of the invention and an instructional material for the use thereof, and optionally an applicator.

BRIEF DESCRIPTION OF THE DRAWINGS

FIG. 3, comprising

FIG. 5, comprising

DETAILED DESCRIPTION

Abbreviations and Acronyms

Figure 1:
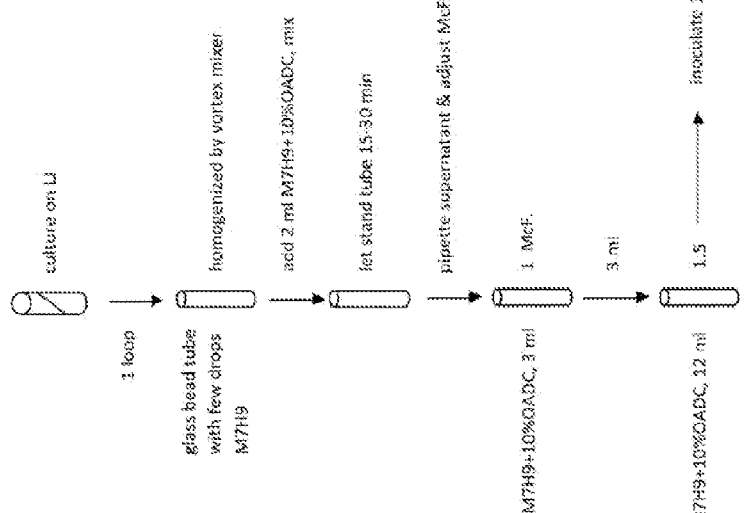
FIG. 1 schematically represents the methods for inoculum preparation and the use of alamar blue.
Figure 2:
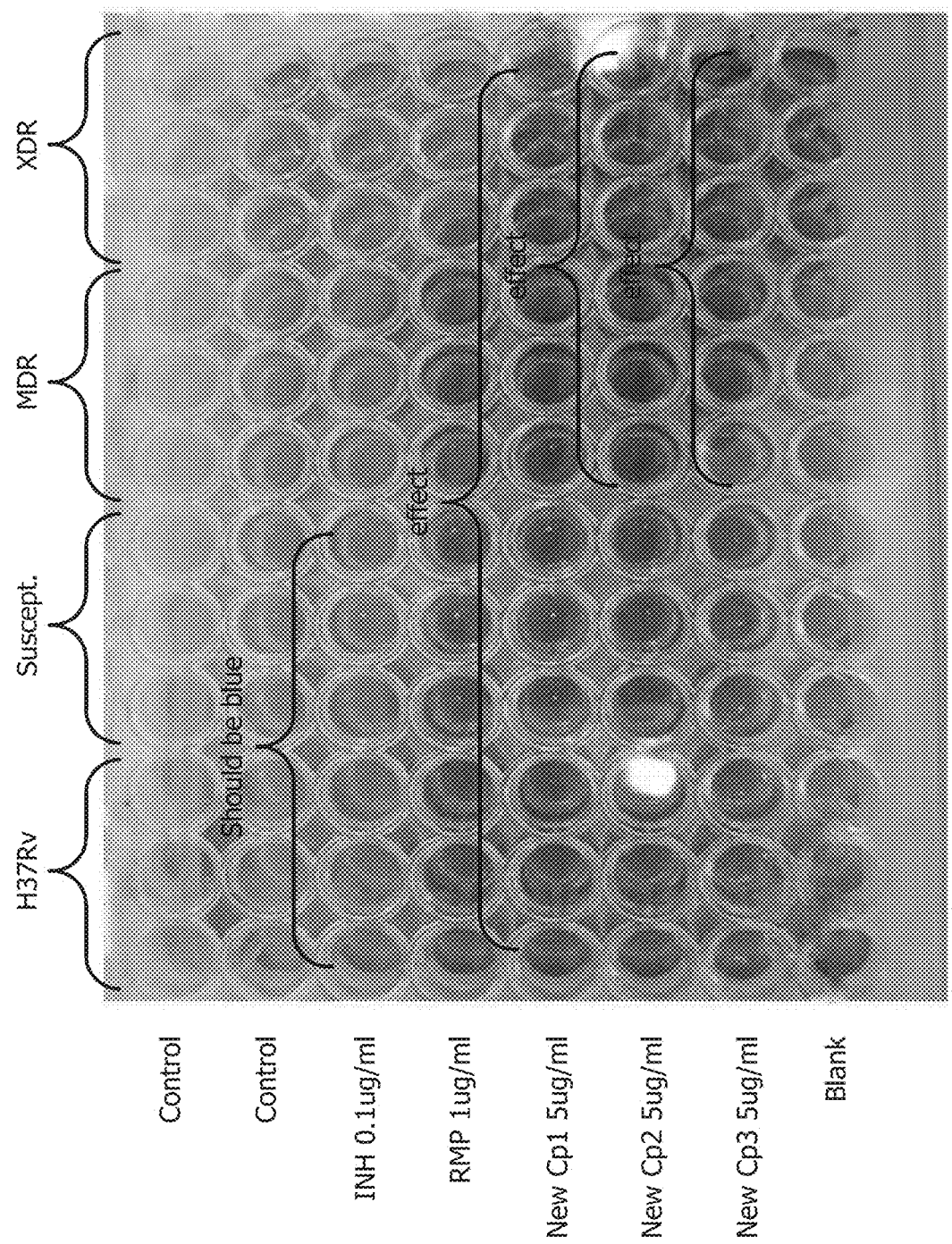
FIG. 2 represents an image illustrating the results of reactions in a 96 well plate testing fours strains, INH, RMP, and three compounds. Alamar blue/rezaxurin: redox indicator: live cells oxidized from blue>red.
Figure 3A:
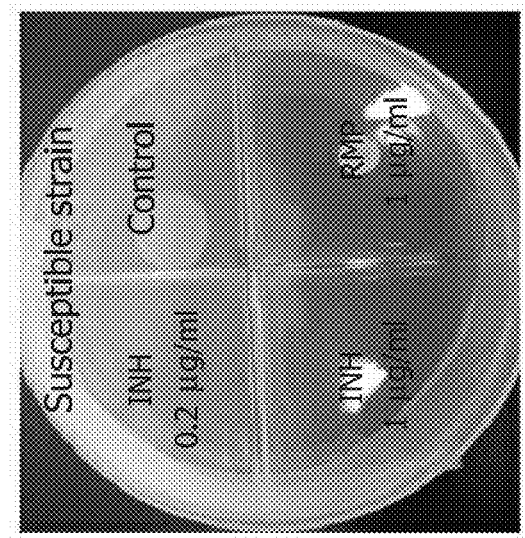
FIGS. 3A-3D, represent images of the results of an agar proportion method experiment testing various mycobacteria strains. Critical concentration; R=>1% of colonies vs control FIG. 4, comprising
Figure 3B:
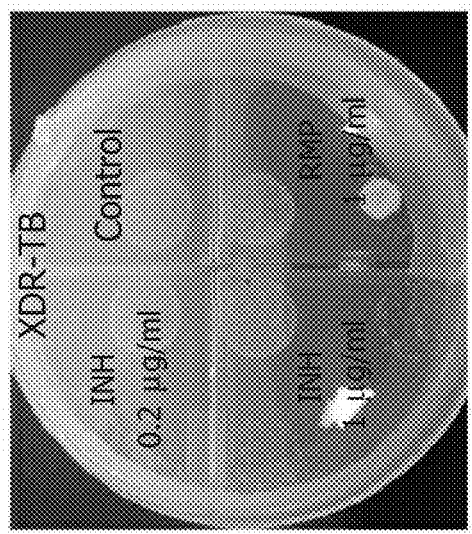
Figure 3C:
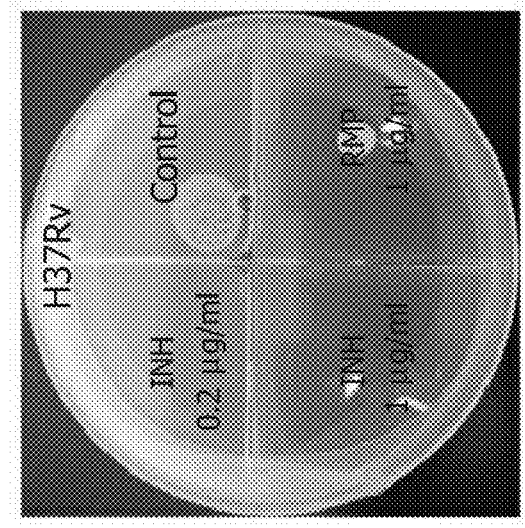
Figure 3D:
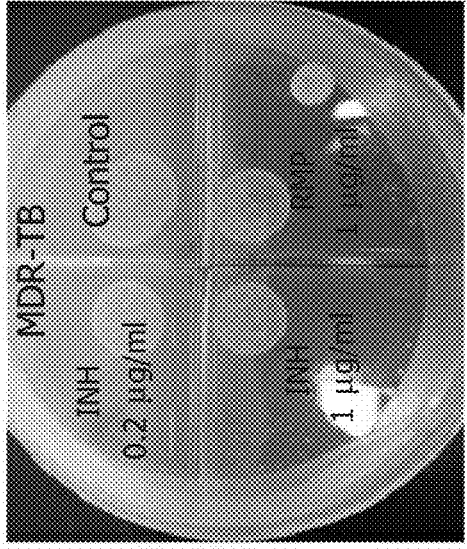
Figure 4A:
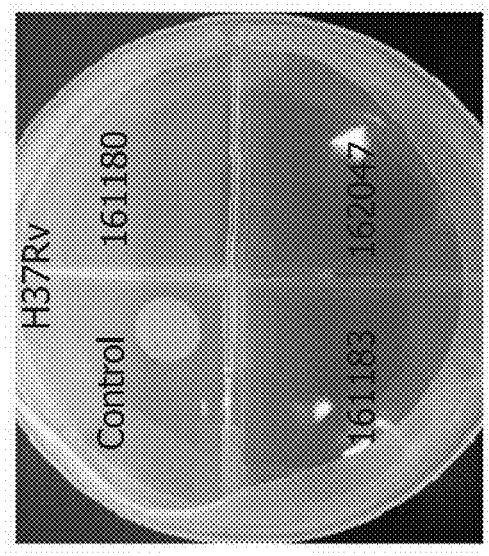
FIGS. 4A-4D, represent images of the results of an agar proportion method experiment testing various mycobacteria strains and compounds of the invention. Agar proportion method Critical concentration 5 µg/ml; R=>1% of colonies vs control.
Figure 4B:
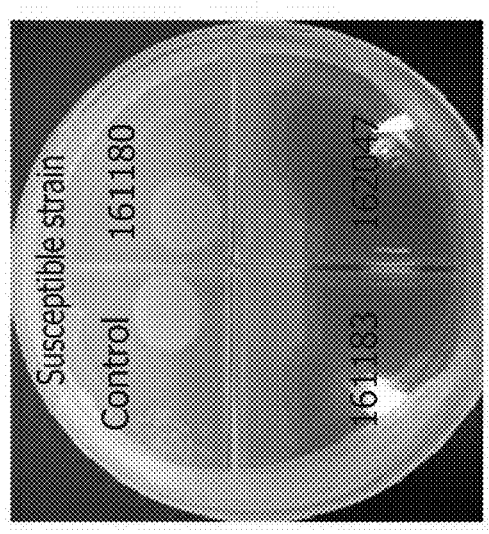
Figure 4C:
Figure 4D:
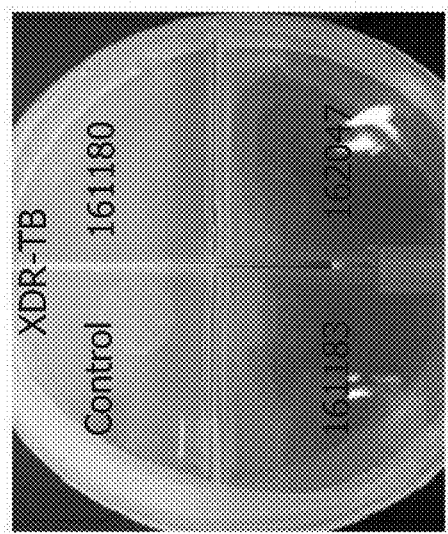
Figure 5A:
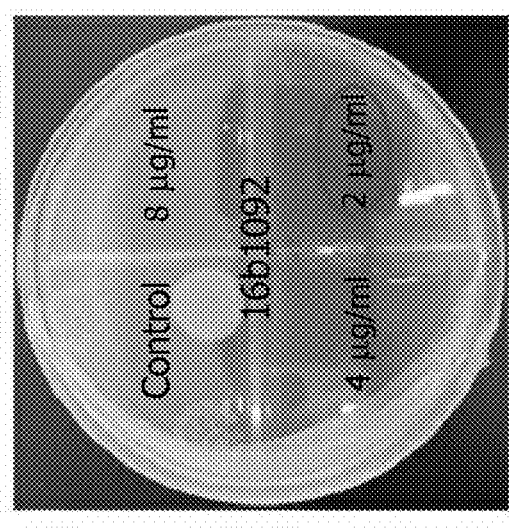
FIGS. 5A-5D, represent images of the results of an agar proportion method experiment for MIC testing various compounds of the invention. MIC Testing (8-0.125 mg/ml) Agar proportion; MIC=lowest concentration with <1% growth FIG. 6. Scheme for Aliphatic Derivatives of 2-amino-5-nitrothiazole.
Figure 5B:
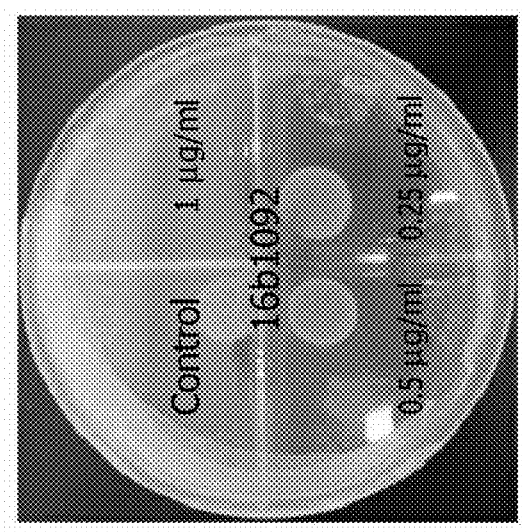
Figure 5C:
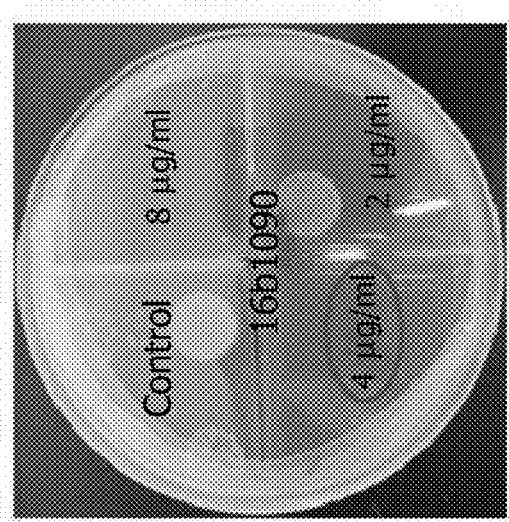
Figure 5D:
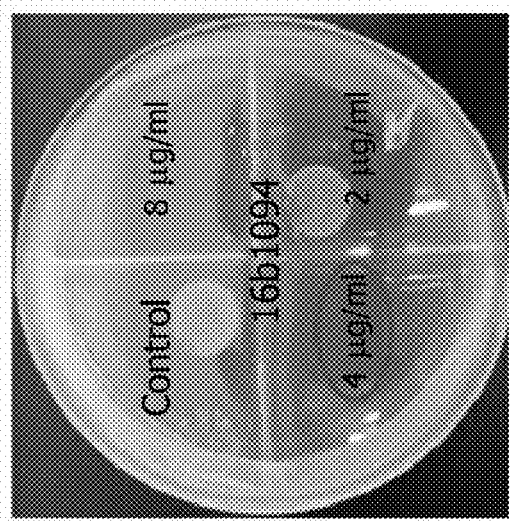

AAF—aggregative adherence fimbriae
Aap—accumulation associated protein
AMIX—amixin (TIZ-ethylamine; compound VPC161219)
CRBSI—catheter-related bloodstream infections
CONS—Coagulase-negative staphylococci
EAEC—Enteroaggregative *Escherichia coli*
EMB—ethambutol
HA—Hemagglutination
ICS—Infection-causing strains
INH—isoniazid
KFOR—2 ketoglutarate oxidoreductase
MDR—multidrug resistant
MIC—minimal inhibiting concentration
MOX—moxifloxacin
MRSA—Methicillin-resistant *Staphylococcus aureus*
MTBC—*M. tuberculosis* complex
NTM—nontuberculosis mycobacteria
NTZ—nitazoxanide
PFOR—pyruvate ferredoxin oxidoreductase
PZA—pyrazinamide
RFLP—restriction fragment length polymorphism
RIF—rifampicin
STR—streptomycin
TB—tuberculosis
TIZ—tizoxanide
TSB or TSA—Trypticase soy broth or agar
XDR—extended drug resistant

Definitions

In describing and claiming the invention, the following terminology will be used in accordance with the definitions set forth below. Unless defined otherwise, all technical and scientific terms used herein have the commonly understood by one of ordinary skill in the art to which the invention pertains. Although any methods and materials similar or equivalent to those described herein may be useful in the practice or testing of the present invention, preferred methods and materials are described below. Specific terminology of particular importance to the description of the present invention is defined below.

The articles "a" and "an" are used herein to refer to one or to more than one (i.e., to at least one) of the grammatical object of the article. By way of example, "an element" means one element or more than one element.

The term "about," as used herein, means approximately, in the region of, roughly, or around. When the term "about" is used in conjunction with a numerical range, it modifies that range by extending the boundaries above and below the numerical values set forth. For example, in one aspect, the term "about" is used herein to modify a numerical value above and below the stated value by a variance of 20%.

The terms "additional therapeutically active compound" or "additional therapeutic agent", as used in the context of the present invention, refers to the use or administration of a compound for an additional therapeutic use for a particular injury, disease, or disorder being treated. Such a compound, for example, could include one being used to treat an unrelated disease or disorder, or a disease or disorder which may not be responsive to the primary treatment for the injury, disease or disorder being treated.

As use herein, the terms "administration of" and or "administering" a compound should be understood to mean providing a compound of the invention or a prodrug of a compound of the invention to a subject in need of treatment.

As used herein, an "agonist" is a composition of matter which, when administered to a mammal such as a human, enhances or extends a biological activity attributable to the level or presence of a target compound or molecule of interest in the subject.

As used herein, "alleviating a disease or disorder symptom," means reducing the severity of the symptom or the frequency with which such a symptom is experienced by a subject, or both.

As used herein, an "analog", or "analogue" of a chemical compound is a compound that, by way of example, resembles another in structure but is not necessarily an isomer (e.g., 5-fluorouracil is an analog of thymine).

An "antagonist" is a composition of matter which when administered to a mammal such as a human, inhibits a biological activity attributable to the level or presence of a compound or molecule of interest in the subject.

The term "antimicrobial agents" as used herein refers to any naturally-occurring, synthetic, or semi-synthetic compound or composition or mixture thereof, which is safe for human or animal use as practiced in the methods of this invention, and is effective in killing or substantially inhibiting the growth of microbes. "Antimicrobial" as used herein, includes antibacterial, antifungal, and antiviral agents.

A "compound," as used herein, refers to any type of substance or agent that is commonly considered a drug, or a candidate for use as a drug, as well as combinations and mixtures of the above. When referring to a compound of the invention, and unless otherwise specified, the term "compound" is intended to encompass not only the specified molecular entity but also its pharmaceutically acceptable, pharmacologically active analogs, including, but not limited to, salts, polymorphs, esters, amides, prodrugs, adducts, conjugates, active metabolites, and the like, where such modifications to the molecular entity are appropriate.

The term "delivery vehicle" refers to any kind of device or material which can be used to deliver compounds in vivo or can be added to a composition comprising compounds administered to a plant or animal. This includes, but is not limited to, implantable devices, aggregates of cells, matrix materials, gels, etc.

As used herein, a "derivative" of a compound refers to a chemical compound that may be produced from another compound of similar structure in one or more steps, as in replacement of H by an alkyl, acyl, or amino group.

As used herein, an "effective amount" or "therapeutically effective amount" means an amount sufficient to produce a selected effect, such as alleviating symptoms of a disease or disorder. In the context of administering compounds in the form of a combination, such as multiple compounds, the amount of each compound, when administered in combination with another compound(s), may be different from when that compound is administered alone. Thus, an effective amount of a combination of compounds refers collectively to the combination as a whole, although the actual amounts of each compound may vary. The term "more effective" means that the selected effect is alleviated to a greater extent by one treatment relative to the second treatment to which it is being compared.

As used in the specification and the appended claims, the terms "for example," "for instance," "such as," "including" and the like are meant to introduce examples that further clarify more general subject matter. Unless otherwise specified, these examples are provided only as an aid for understanding the invention, and are not meant to be limiting in any fashion.

The terms "formula" and "structure" are used interchangeably herein.

As used herein, a "functional" molecule is a molecule in a form in which it exhibits a property or activity by which it is characterized. A functional enzyme, for example, is one that exhibits the characteristic catalytic activity by which the enzyme is characterized.

As used herein, "homology" is used synonymously with "identity."

The term "inhibit," as used herein, refers to the ability of a compound of the invention to reduce or impede a described function, such as, for example, having activity against cell proliferation or activity against an enzyme. Preferably, inhibition is by at least 10%, more preferably by at least 25%, even more preferably by at least 50%, and most preferably, the function is inhibited by at least 75%. The terms "inhibit", "reduce", and "block" are used interchangeably herein.

As used herein "injecting or applying" includes administration of a compound of the invention by any number of routes and means including, but not limited to, topical, oral, buccal, intravenous, intramuscular, intra arterial, intramedullary, intrathecal, intraventricular, transdermal, subcutaneous, intraperitoneal, intranasal, enteral, topical, sublingual, vaginal, ophthalmic, pulmonary, or rectal means.

As used herein, an "instructional material" includes a publication, a recording, a diagram, or any other medium of expression which can be used to communicate the usefulness of the peptide of the invention in the kit for effecting alleviation of the various diseases or disorders recited herein. Optionally, or alternately, the instructional material may describe one or more methods of alleviating the diseases or disorders in a cell or a tissue of a mammal. The instructional material of the kit of the invention may, for example, be affixed to a container which contains the identified compound invention or be shipped together with a container which contains the identified compound. Alternatively, the instructional material may be shipped separately from the container with the intention that the instructional material and the compound be used cooperatively by the recipient.

The term "modulate", as used herein, refers to changing the level of an activity, function, or process. The term "modulate" encompasses both inhibiting and stimulating an activity, function, or process.

As used herein, the term "pharmaceutically acceptable carrier" includes any of the standard pharmaceutical carriers, such as a phosphate buffered saline solution, water, emulsions such as an oil/water or water/oil emulsion, and various types of wetting agents. The term also encompasses any of the agents approved by a regulatory agency of the US Federal government or listed in the US Pharmacopeia for use in animals, including humans.

The term "pilicide", as used herein, refers to small molecule inhibitors of filament biogenesis.

The term "prevent," as used herein, means to stop something from happening, or taking advance measures against something possible or probable from happening. In the context of medicine, "prevention" generally refers to action taken to decrease the chance of getting a disease or condition.

A "preventive" or "prophylactic" treatment is a treatment administered to a subject who does not exhibit signs, or exhibits only early signs, of a disease or disorder. A prophylactic or preventative treatment is administered for the purpose of decreasing the risk of developing pathology associated with developing the disease or disorder.

"Primer" refers to a polynucleotide that is capable of specifically hybridizing to a designated polynucleotide template and providing a point of initiation for synthesis of a complementary polynucleotide. Such synthesis occurs when the polynucleotide primer is placed under conditions in which synthesis is induced, i.e., in the presence of nucleotides, a complementary polynucleotide template, and an agent for polymerization such as DNA polymerase. A primer is typically single-stranded, but may be double-stranded. Primers are typically deoxyribonucleic acids, but a wide variety of synthetic and naturally occurring primers are useful for many applications. A primer is complementary to the template to which it is designed to hybridize to serve as a site for the initiation of synthesis, but need not reflect the exact sequence of the template. In such a case, specific hybridization of the primer to the template depends on the stringency of the hybridization conditions. Primers can be labeled with, e.g., chromogenic, radioactive, or fluorescent moieties and used as detectable moieties.

The term "prevent," as used herein, means to stop something from happening, or taking advance measures against something possible or probable from happening. In the context of medicine, "prevention" generally refers to action taken to decrease the chance of getting a disease or condition.

A "preventive" or "prophylactic" treatment is a treatment administered to a subject who does not exhibit signs, or exhibits only early signs, of a disease or disorder. A prophylactic or preventative treatment is administered for the purpose of decreasing the risk of developing pathology associated with developing the disease or disorder.

A "prodrug" refers to an agent that is converted into the parent drug in vivo. Prodrugs are often useful because, in some situations, they may be easier to administer than the parent drug. They may, for instance, be bioavailable by oral administration whereas the parent is not. The prodrug may also have improved solubility in pharmaceutical compositions over the parent drug, or may demonstrate increased palatability or be easier to formulate.

As used herein, the term "purified" and like terms relate to an enrichment of a molecule or compound relative to other components normally associated with the molecule or compound in a native environment. The term "purified" does not necessarily indicate that complete purity of the particular molecule has been achieved during the process. A "highly purified" compound as used herein refers to a compound that is greater than 90% pure.

The term "regulate" refers to either stimulating or inhibiting a function or activity of interest.

A "subject" of diagnosis or treatment is a mammal, including a human, as well as other organisms of interest.

The term "symptom," as used herein, refers to any morbid phenomenon or departure from the normal in structure, function, or sensation, experienced by the patient and indicative of disease. In contrast, a "sign" is objective evidence of disease. For example, a bloody nose is a sign. It is evident to the patient, doctor, nurse and other observers.

As used herein, the term "treating" includes prophylaxis of the specific disorder or condition, or alleviation of the symptoms associated with a specific disorder or condition and/or preventing or eliminating said symptoms. A "prophylactic" treatment is a treatment administered to a subject who does not exhibit signs of a disease or exhibits only early signs of the disease for the purpose of decreasing the risk of developing pathology associated with the disease.

A "therapeutic" treatment is a treatment administered to a subject who exhibits signs of pathology for the purpose of diminishing or eliminating those signs.

A "therapeutically effective amount" of a compound is that amount of compound which is sufficient to provide a beneficial effect to the subject to which the compound is administered.

As used herein, the term "treating" includes prophylaxis of the specific disease, disorder, or condition, or alleviation of the symptoms associated with a specific disease, disorder, or condition and/or preventing or eliminating said symptoms.

As used herein, the term "wound" relates to a physical tear, break, or rupture to a tissue or cell layer. A wound may occur by any physical insult, including a surgical procedure or as a result of a disease, disorder condition.

Chemical Definitions

As used herein, the term "halogen" or "halo" includes bromo, chloro, fluoro, and iodo.

The term "haloalkyl" as used herein refers to an alkyl radical bearing at least one halogen substituent, for example, chloromethyl, fluoroethyl or trifluoromethyl and the like.

The term "$C_1$-$C_n$ alkyl" wherein n is an integer, as used herein, represents a branched or linear alkyl group having from one to the specified number of carbon atoms. Typically, $C_1$-$C_6$ alkyl groups include, but are not limited to, methyl, ethyl, n-propyl, iso-propyl, butyl, iso-butyl, sec-butyl, tert-butyl, pentyl, hexyl, and the like.

The term "$C_2$-$C_n$ alkenyl" wherein n is an integer, as used herein, represents an olefinically unsaturated branched or linear group having from 2 to the specified number of carbon atoms and at least one double bond. Examples of such groups include, but are not limited to, 1-propenyl, 2-propenyl, 1,3-butadienyl, 1-butenyl, hexenyl, pentenyl, and the like.

The term "$C_2$-$C_n$ alkynyl" wherein n is an integer refers to an unsaturated branched or linear group having from 2 to the specified number of carbon atoms and at least one triple bond. Examples of such groups include, but are not limited to, 1-propynyl, 2-propynyl, 1-butynyl, 2-butynyl, 1-pentynyl, and the like.

The term "$C_3$-$C_n$ cycloalkyl" wherein n=8, represents cyclopropyl, cyclobutyl, cyclopentyl, cyclohexyl, cycloheptyl, and cyclooctyl.

As used herein, the term "optionally substituted" typically refers to from zero to four substituents, wherein the substituents are each independently selected. Each of the independently selected substituents may be the same or different than other substituents. For example, the substituents of an R group of a formula may be optionally substituted (e.g., from 1 to 4 times) with independently selected H, halogen, hydroxy, acyl, alkyl, alkenyl, alkynyl, cycloalkyl, heterocyclo, aryl, heteroaryl, alkoxy, amino, amide, thiol, sulfone, sulfoxide, oxo, oxy, nitro, carbonyl, carboxy, amino acid sidechain and amino acid.

As used herein the term "aryl" refers to an optionally substituted mono- or bicyclic carbocyclic ring system having one or two aromatic rings including, but not limited to, phenyl, benzyl, naphthyl, tetrahydronaphthyl, indanyl, indenyl, and the like. "Optionally substituted aryl" includes aryl compounds having from zero to four substituents, and "substituted aryl" includes aryl compounds having one or more substituents. The term ($C_5$-$C_8$ alkyl)aryl refers to any aryl group which is attached to the parent moiety via the alkyl group.

"Heterocycle" refers to any stable 4, 5, 6, 7, 8, 9, 10, 11, or 12 membered, (unless the number of members is otherwise recited), monocyclic, bicyclic, or tricyclic heterocyclic ring that is saturated or partially unsaturated, and which consists of carbon atoms and 1, 2, 3, or 4 heteroatoms independently selected from the group consisting of N, O, and S. If the heterocycle is defined by the number of carbons atoms, then from 1, 2, 3, or 4 of the listed carbon atoms are replaced by a heteroatom. If the heterocycle is bicyclic or tricyclic, then at least one of the two or three rings must contain a heteroatom, though both or all three may each contain one or more heteroatoms. The N group may be N, NH, or N-substituent, depending on the chosen ring and if substituents are recited. The nitrogen and sulfur heteroatoms optionally may be oxidized (e.g., S, S(O), S(O)$_2$, and N—O). The heterocycle may be attached to its pendant group at any heteroatom or carbon atom that results in a stable structure. The heterocycles described herein may be substituted on carbon or on a nitrogen atom if the resulting compound is stable.

"Heteroaryl" refers to any stable 5, 6, 7, 8, 9, 10, 11, or 12 membered, (unless the number of members is otherwise recited), monocyclic, bicyclic, or tricyclic heterocyclic ring that is aromatic, and which consists of carbon atoms and 1, 2, 3, or 4 heteroatoms independently selected from the group consisting of N, O, and S. If the heteroaryl is defined by the number of carbons atoms, then 1, 2, 3, or 4 of the listed carbon atoms are replaced by a heteroatom. If the heteroaryl group is bicyclic or tricyclic, then at least one of the two or three rings must contain a heteroatom, though both or all three may each contain one or more heteroatoms. If the heteroaryl group is bicyclic or tricyclic, then only one of the rings must be aromatic. The N group may be N, NH, or N-substituent, depending on the chosen ring and if substituents are recited. The nitrogen and sulfur heteroatoms may optionally be oxidized (e.g., S, S(O), S(O)$_2$, and N—O). The heteroaryl ring may be attached to its pendant group at any heteroatom or carbon atom that results in a stable structure. The heteroaryl rings described herein may be substituted on carbon or on a nitrogen atom if the resulting compound is stable."

The term "heteroatom" means for example oxygen, sulfur, nitrogen, phosphorus, or silicon (including, any oxidized form of nitrogen, sulfur, phosphorus, or silicon; the quaternized form of any basic nitrogen or; a substitutable nitrogen of a heterocyclic ring.

The term "bicyclic" represents either an unsaturated or saturated stable 7- to 12-membered bridged or fused bicyclic carbon ring. The bicyclic ring may be attached at any carbon atom which affords a stable structure. The term includes, but is not limited to, naphthyl, dicyclohexyl, dicyclohexenyl, and the like.

The compounds of the present invention contain one or more asymmetric centers in the molecule. In accordance with the present invention a structure that does not designate the stereochemistry is to be understood as embracing all the various optical isomers, as well as racemic mixtures thereof.

The compounds of the present invention may exist in tautomeric forms and the invention includes both mixtures and separate individual tautomers. For example the following structure:

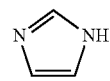

is understood to represent a mixture of the structures:

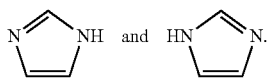

The term "pharmaceutically-acceptable salt" refers to salts which retain the biological effectiveness and properties of the compounds of the present invention and which are not biologically or otherwise undesirable. In many cases, the compounds of the present invention are capable of forming acid and/or base salts by virtue of the presence of amino and/or carboxyl groups or groups similar thereto. Compounds of the present invention that have one or more asymmetric carbon atoms may exist as the optically pure enantiomers, or optically pure diastereomers, as well as mixtures of enantiomers, mixtures of diastereomers, and racemic mixtures of such stereoisomers. The present invention includes within its scope all such isomers and mixtures thereof.

Embodiments

As described herein, the compositions of the present invention comprise, as an active agent, compounds having the structure of any of the formulas disclosed herein in a pharmaceutically acceptable form. If desired, the compositions may further comprise one or more additional active agents. Where it is appropriate, any of the active agents may be administered in the form of the compound per se, and/or in the form of a salt, polymorph, ester, amide, prodrug, derivative, or the like, provided the salt, polymorph, ester, amide, prodrug or derivative is suitable pharmacologically. Where it is appropriate, salts, esters, amides, prodrugs and other derivatives of the active agents may be prepared using standard procedures known to those skilled in the art of synthetic organic chemistry and described, for example, by J. March, Advanced Organic Chemistry: Reactions, Mechanisms and Structure, 4th Ed. (New York: Wiley-Interscience, 1992). For any active agents that may exist in enantiomeric forms, the active agent may be incorporated into the present compositions either as the racemate or in enantiomerically enriched form.

In addition to the specific compounds claimed herein, other useful compounds encompassed by the generic formulas provided herein include, but are not limited to:

VPC16a1007

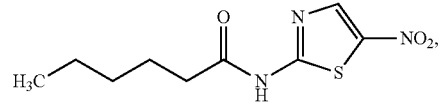

VPC161219

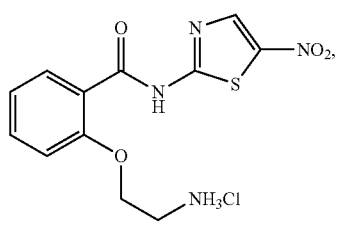

VPC162134

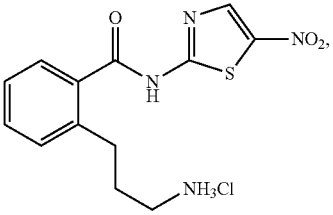

VPC162125

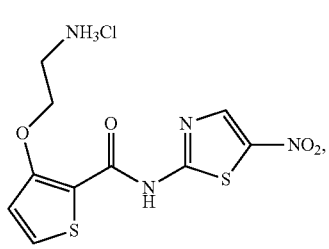

VPC16a1028

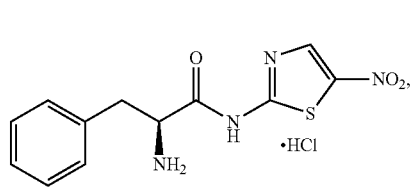

VPC162047

VPC16a1052

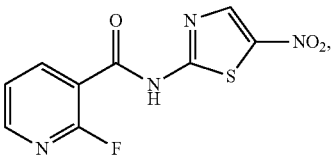

VPC16b1031

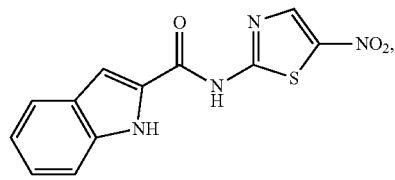

VPC162082

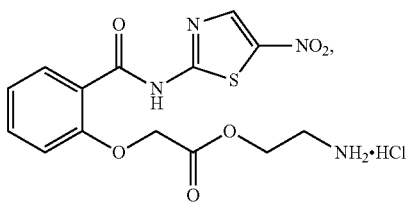

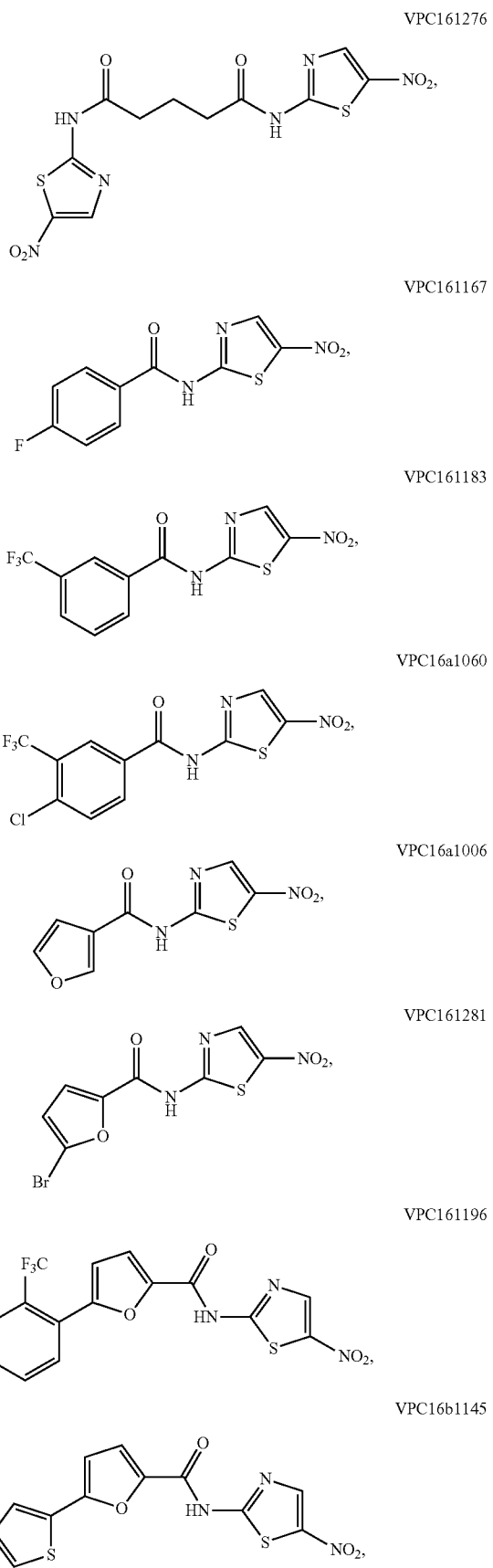
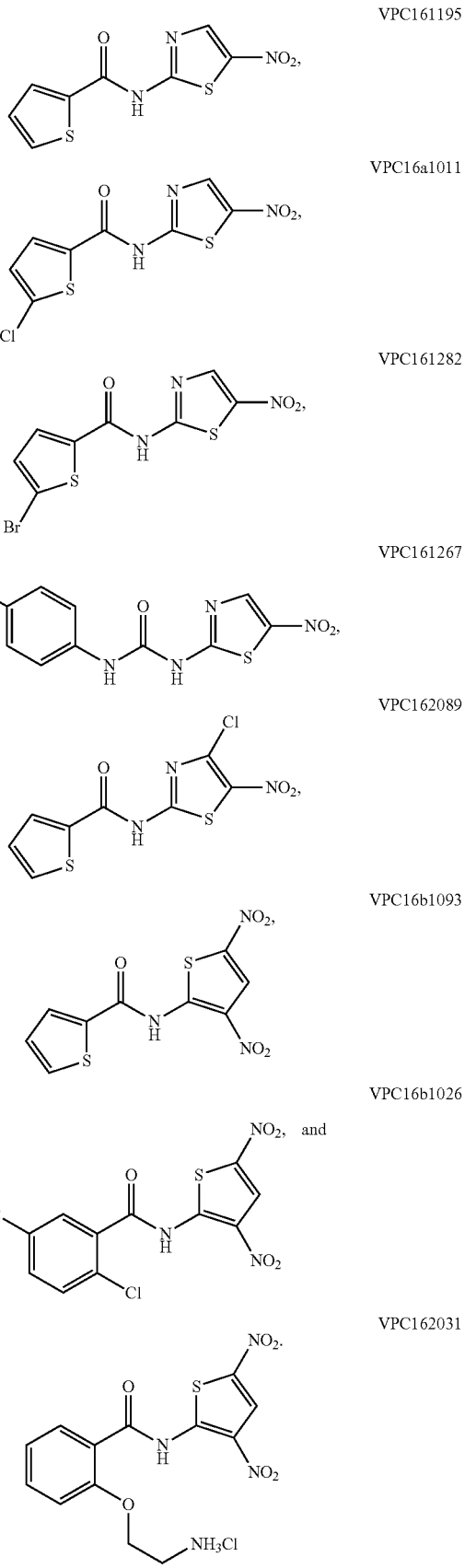

The values provided herein for radicals, substituents, and ranges, are for illustration only; they do not exclude other defined values or other values within defined ranges for the radicals and substituents. The disclosed compounds include compounds of the specific Formulas recited herein having any combination of the exemplary values, preferred values, and more preferred values described herein.

Processes for preparing compounds of any of the formulas of the invention or for preparing intermediates useful for preparing compounds of any of the formulas of the invention are provided as further embodiments of the invention. Intermediates useful for preparing compounds of formula I are also provided as further embodiments of the invention.

In cases where compounds are sufficiently basic or acidic to form acid or base salts, use of the compounds as salts may be appropriate. Examples of acceptable salts are organic acid addition salts formed with acids which form a physiological acceptable anion, for example, tosylate, methanesulfonate, acetate, citrate, malonate, tartarate, succinate, benzoate, ascorbate, α-ketoglutarate, and α-glycerophosphate. Suitable inorganic salts may also be formed, including hydrochloride, sulfate, nitrate, bicarbonate, and carbonate salts.

Acceptable salts may be obtained using standard procedures well known in the art, for example by reacting a sufficiently basic compound such as an amine with a suitable acid affording a physiologically acceptable anion. Alkali metal (for example, sodium, potassium or lithium) or alkaline earth metal (for example calcium) salts of carboxylic acids can also be made.

Processes for preparing compounds of any of the formulas of the invention are provided as further embodiments of the invention and are illustrated by the following procedures in which the meanings of the generic radicals are as given above unless otherwise qualified.

In cases where compounds are sufficiently basic or acidic to form stable nontoxic acid or base salts, administration of the compounds as salts may be appropriate. Examples of pharmaceutically acceptable salts are organic acid addition salts formed with acids which form a physiological acceptable anion, for example, tosylate, methanesulfonate, acetate, citrate, malonate, tartarate, succinate, benzoate, ascorbate, -ketoglutarate, and -glycerophosphate. Suitable inorganic salts may also be formed, including hydrochloride, sulfate, nitrate, bicarbonate, and carbonate salts.

Pharmaceutically acceptable salts may be obtained using standard procedures well known in the art, for example by reacting a sufficiently basic compound such as an amine with a suitable acid affording a physiologically acceptable anion. Alkali metal (for example, sodium, potassium or lithium) or alkaline earth metal (for example calcium) salts of carboxylic acids can also be made.

The compounds of any of the formulas of the invention can be formulated as pharmaceutical compositions and administered to a mammalian host, such as a human patient in a variety of forms adapted to the chosen route of administration, i.e., orally or parenterally, by intravenous, intramuscular, topical or subcutaneous routes.

It will be appreciated that compounds of the invention can be administered using various kinds of delivery systems and media. Furthermore, compounds of the invention can be administered in combination with other therapeutic agents and compounds and can be used with other kinds of treatments.

Thus, the present compounds may be systemically administered, e.g., orally, in combination with a pharmaceutically acceptable vehicle such as an inert diluent or an assimilable edible carrier. They may be enclosed in hard or soft shell gelatin capsules, may be compressed into tablets, or may be incorporated directly with the food of the patient's diet. For oral therapeutic administration, the active compound may be combined with one or more excipients and used in the form of ingestible tablets, buccal tablets, troches, capsules, elixirs, suspensions, syrups, wafers, and the like. Such compositions and preparations should contain at least 0.1% of active compound. The percentage of the compositions and preparations may, of course, be varied and may conveniently be between about 2 to about 60% of the weight of a given unit dosage form. The amount of active compound in such therapeutically useful compositions is such that an effective dosage level will be obtained.

The tablets, troches, pills, capsules, and the like may also contain the following: binders such as gum tragacanth, acacia, corn starch or gelatin; excipients such as dicalcium phosphate; a disintegrating agent such as corn starch, potato starch, alginic acid and the like; a lubricant such as magnesium stearate; and a sweetening agent such as sucrose, fructose, lactose or aspartame or a flavoring agent such as peppermint, oil of wintergreen, or cherry flavoring may be added. When the unit dosage form is a capsule, it may contain, in addition to materials of the above type, a liquid carrier, such as a vegetable oil or a polyethylene glycol. Various other materials may be present as coatings or to otherwise modify the physical form of the solid unit dosage form. For instance, tablets, pills, or capsules may be coated with gelatin, wax, shellac or sugar and the like. A syrup or elixir may contain the active compound, sucrose or fructose as a sweetening agent, methyl and propylparabens as preservatives, a dye and flavoring such as cherry or orange flavor. Of course, any material used in preparing any unit dosage form should be pharmaceutically acceptable and substantially non-toxic in the amounts employed. In addition, the active compound may be incorporated into sustained-release preparations and devices.

The active compound may also be administered intravenously or intraperitoneally by infusion or injection. Solutions of the active compound or its salts can be prepared in water, optionally mixed with a nontoxic surfactant. Dispersions can also be prepared in glycerol, liquid polyethylene glycols, triacetin, and mixtures thereof and in oils. Under ordinary conditions of storage and use, these preparations contain a preservative to prevent the growth of microorganisms.

The pharmaceutical dosage forms suitable for injection or infusion can include sterile aqueous solutions or dispersions or sterile powders comprising the active ingredient which are adapted for the extemporaneous preparation of sterile injectable or infusible solutions or dispersions, optionally encapsulated in liposomes. In all cases, the ultimate dosage form should be sterile, fluid and stable under the conditions of manufacture and storage. The liquid carrier or vehicle can be a solvent or liquid dispersion medium comprising, for example, water, ethanol, a polyol (for example, glycerol, propylene glycol, liquid polyethylene glycols, and the like), vegetable oils, nontoxic glyceryl esters, and suitable mixtures thereof. The proper fluidity can be maintained, for example, by the formation of liposomes, by the maintenance of the required particle size in the case of dispersions or by the use of surfactants. The prevention of the action of microorganisms can be brought about by various antibacterial and antifungal agents, for example, parabens, chlorobutanol, phenol, sorbic acid, thimerosal, and the like. In many cases, it will be preferable to include isotonic agents, for example, sugars, buffers or sodium chloride. Prolonged absorption of the injectable compositions can be brought about by the use in the compositions of agents delaying absorption, for example, aluminum monostearate, and gelatin.

Sterile injectable solutions are prepared by incorporating the active compound in the required amount in the appropriate solvent with various of the other ingredients enumerated above, as required, followed by filter sterilization. In the case of sterile powders for the preparation of sterile injectable solutions, the preferred methods of preparation are vacuum drying and the freeze-drying techniques, which yield a powder of the active ingredient plus any additional desired ingredient present in the previously sterile-filtered solutions.

For topical administration, the present compounds may be applied in pure form, i.e., when they are liquids. However, it will generally be desirable to administer them to the skin as compositions or formulations, in combination with a dermatologically acceptable carrier, which may be a solid or a liquid.

Useful solid carriers include finely divided solids such as talc, clay, microcrystalline cellulose, silica, alumina and the like. Useful liquid carriers include water, alcohols or glycols or water-alcohol/glycol blends, in which the present compounds can be dissolved or dispersed at effective levels, optionally with the aid of non-toxic surfactants. Adjuvants such as fragrances and additional antimicrobial agents can be added to optimize the properties for a given use. The resultant liquid compositions can be applied from absorbent pads, used to impregnate bandages and other dressings, or sprayed onto the affected area using pump-type or aerosol sprayers.

Thickeners such as synthetic polymers, fatty acids, fatty acid salts and esters, fatty alcohols, modified celluloses or modified mineral materials can also be employed with liquid carriers to form spreadable pastes, gels, ointments, soaps, and the like, for application directly to the skin of the user.

Examples of useful dermatological compositions which can be used to deliver the compounds of formula I to the skin are known to the art; for example, see Jacquet et al. (U.S. Pat. No. 4,608,392), Geria (U.S. Pat. No. 4,992,478), Smith et al. (U.S. Pat. No. 4,559,157) and Wortzman (U.S. Pat. No. 4,820,508).

Useful dosages of the compounds of formula I can be determined by comparing their in vitro activity, and in vivo activity in animal models. Methods for the extrapolation of effective dosages in mice, and other animals, to humans are known to the art; for example, see U.S. Pat. No. 4,938,949.

Generally, the concentration of the compound(s) of formula I in a liquid composition, such as a lotion, will be from about 0.1-25 wt-%, preferably from about 0.5-10 wt-%. The concentration in a semi-solid or solid composition such as a gel or a powder will be about 0.1-5 wt-%, preferably about 0.5-2.5 wt-%.

The amount of the compound, or an active salt or derivative thereof, required for use in treatment will vary not only with the particular salt selected but also with the route of administration, the nature of the condition being treated and the age and condition of the patient and will be ultimately at the discretion of the attendant physician or clinician.

In general, however, a suitable dose will be in the range of from about 0.5 to about 100 mg/kg, e.g., from about 10 to about 75 mg/kg of body weight per day, such as 3 to about 50 mg per kilogram body weight of the recipient per day, preferably in the range of 6 to 90 mg/kg/day, most preferably in the range of 15 to 60 mg/kg/day.

The compound is conveniently administered in unit dosage form; for example, containing 5 to 1000 mg, conveniently 10 to 750 mg, most conveniently, 50 to 500 mg of active ingredient per unit dosage form.

Ideally, when the active ingredient needs to enter circulation and be delivered via blood, the active ingredient, in one embodiment, should be administered to achieve peak plasma concentrations of the active compound of from about 0.5 to about 75 μM, preferably, about 1 to 50 μM, most preferably, about 2 to about 30 μM. This may be achieved, for example, by the intravenous injection of a 0.05 to 5% solution of the active ingredient, optionally in saline, or orally administered as a bolus containing about 1-100 mg of the active ingredient. Desirable blood levels may be maintained by continuous infusion to provide about 0.01-5.0 mg/kg/hr or by intermittent infusions containing about 0.4-15 mg/kg of the active ingredient(s).

The desired dose may conveniently be presented in a single dose or as divided doses administered at appropriate intervals, for example, as two, three, four or more sub-doses per day. The sub-dose itself may be further divided, e.g., into a number of discrete loosely spaced administrations; such as multiple inhalations from an insufflator or by application of a plurality of drops into the eye.

In another embodiment, a formulation of the invention can be impregnated into a dressing material (or otherwise contained or encompassed by the dressing material). The dressing material is a pharmaceutically acceptable fabric. It can be, for example, gauze or any other type of medical fabric or material that can be used to cover a wound and/or to keep a therapeutic agent or composition in contact with a patient.

The composition of the invention can further comprise additional therapeutic additives, alone or in combination (e.g., 2, 3, or 4 additional additives). Examples of additional additives include but are not limited to: (a) antimicrobials, (b) steroids (e.g., hydrocortisone, triamcinolone); (c) pain medications (e.g., aspirin, an NSAID, and a local anesthetic); (d) anti-inflammatory agents; and (e) combinations thereof.

Non-synthetic matrix proteins like collagen, glycosaminoglycans, and hyaluronic acid, which are enzymatically digested in the body, are useful for delivery (see U.S. Pat. Nos. 4,394,320; 4,472,840; 5,366,509; 5,606,019; 5,645,591; and 5,683,459) and are suitable for use with the present invention. Other implantable media and devices can be used for delivery of the compounds of the invention in vivo. These include, but are not limited to, sponges, such as those from Integra, fibrin gels, scaffolds formed from sintered microspheres of polylactic acid glycolic acid copolymers (PLAGA), and nanofibers formed from native collagen, as well as other proteins. The compounds of the present invention can be further combined with growth factors, nutrient factors, pharmaceuticals, calcium-containing compounds, anti-inflammatory agents, antimicrobial agents, or any other substance capable of expediting or facilitating bone or tissue growth, stability, and remodeling.

The compositions of the present invention can also be combined with inorganic fillers or particles. For example for use in implantable grafts the inorganic fillers or particles can be selected from hydroxyapatite, tri-calcium phosphate, ceramic glass, amorphous calcium phosphate, porous ceramic particles or powders, mesh titanium or titanium alloy, or particulate titanium or titanium alloy.

Examples of other antimicrobial agents that can be used in the present invention include, but are not limited to, isoniazid, ethambutol, pyrazinamide, streptomycin, clofazimine, rifabutin, fluoroquinolones, ofloxacin, sparfloxacin, rifampin, azithromycin, clarithromycin, dapsone, tetracycline, erythromycin, cikprofloxacin, doxycycline, ampicillin, amphotericine B, ketoconazole, fluconazole, pyrimethamine, sulfadiazine, clindamycin, lincomycin, pentamidine, atovaquone, paromomycin, diclarazaril, acyclovir, trifluorouridine, foscarnet, penicillin, gentamicin, ganciclovir, iatroconazole, miconazole, Zn-pyrithione, and silver salts, such as chloride, bromide, iodide, and periodate.

In one embodiment, the compounds of the invention can first be encapsulated into microcapsules, microspheres, microparticles, microfibers, reinforcing fibers and the like to facilitate mixing and achieving controlled, extended, delayed and/or sustained release and combined other agents or drugs. Encapsulating the biologically active agent can also protect the agent against degradation during formation of the composite of the invention.

In another embodiment of the invention, the compound is controllably released into a subject when the composition of the invention is implanted into a subject, due to bioresorption relying on the time scale resulting from cellular remodeling. In one aspect, the composition may be used to replace an area of discontinuity in the tissue. The area of discontinuity can be the result of trauma, a disease, disorder, or condition, surgery, injury, etc.

As used herein, an "instructional material" includes a publication, a recording, a diagram, or any other medium of expression which can be used to communicate the usefulness of the composition of the invention for its designated use. The instructional material of the kit of the invention may, for example, be affixed to a container which contains the composition or be shipped together with a container which contains the composition. Alternatively, the instructional material may be shipped separately from the container with the intention that the instructional material and the composition be used cooperatively by the recipient.

The method of the invention includes a kit comprising a compound identified in the invention and an instructional material which describes administering the compound or a composition comprising the compound to a cell or a subject to any target of interest, such as a surface. This should be construed to include other embodiments of kits that are known to those skilled in the art, such as a kit comprising a (preferably sterile) solvent suitable for dissolving or suspending the composition of the invention prior to administering the compound to a cell or a subject. Preferably the subject is a human.

In accordance with the present invention, as described above or as discussed in the Examples below, there can be employed conventional chemical, cellular, histochemical, biochemical, molecular biology, microbiology, and in vivo techniques which are known to those of skill in the art. Such techniques are explained fully in the literature.

Without further description, it is believed that one of ordinary skill in the art can, using the preceding description and the following illustrative examples, make and utilize the compounds of the present invention.

The invention is now described with reference to the following Examples and Embodiments. Without further description, it is believed that one of ordinary skill in the art can, using the preceding description and the following illustrative examples, make and utilize the present invention and practice the claimed methods. The following working examples therefore, are provided for the purpose of illustration only and specifically point out the preferred embodiments of the present invention, and are not to be construed as limiting in any way the remainder of the disclosure. Therefore, the examples should be construed to encompass any and all variations which become evident as a result of the teaching provided herein.

Other useful techniques that can be practiced with the present invention can be found in the art, such as in Rossignol et al. (WO2007081974).

EXAMPLES

The results described below demonstrate that derivatives and analogs of nitazoxanide have greatly enhanced anti-microbial activity, including against mycobacteria.

A series of nitazoxanide derivatives and analogues are disclosed herein for use in killing *mycobacterium* and treating subjects with mycobacterial infections, including TB patients. Compounds of this family and their preparation are described in International Patent Publication Number WO 2010/107736 (Hoffman et al.) published Sep. 23, 2010 (Int. App. No. PCT/US2010027397). As disclosed herein, it has now been determined that some of the compounds are useful against *mycobacterium*. Additionally, some of the compounds have at least dual activity as they appear to act via different proteins in different types of bacteria. By dual activity is meant they act on at least two different proteins or pathways, although it does not exclude the possibility that the mechanism of action is similar in both cases such as regulating a common co-factor or binding to similar sites on the target proteins.

Example 1

Anti-Mycobacterial Activity of Nitazoxanide Derivatives and Analogs

Materials and Methods (1) Strains: *Mycobacterium smegmatis* mc2155, *Mycobacterium chelonae* EOP-1, *Mycobacterium marinum* ATCC 927, *Mycobacterium avium* Va14(T), and *Mycobacterium abscessus* AAy-P-1).

(2) Medium: Middlebrook 7H9 containing 0.5% (vol/vol) glycerol and 10% (vol/vol) oleic acid-albumin.

(3) Incubation Temperature: 37° C., except *M. marinum* 30° C.

(4) Nitazoxanides: Precipitates were present in wells of nitazoxanides with high concentrations (250-31 µg/mL) except for 162080, 162088, 16b2026, and 16b2031. Fortunately, the presence of precipitate did not obscure identification of MIC values.

(5) Decolorization: Almost all the yellow nitazoxanides, namely 16b1090, 16b1092 and 16b1093, 16b1094, 16b2023, 16b2025, and 16b2026 were decolorized by *M. smegmatis* strain mc2155. None of the other mycobacterial strains decolorized the compounds. Note that the compound numbers are also referred to herein with the prefix VPC.

Representative mycobacteria include: *M. tuberculosis, M. bovis, M. bovis* BCG, *M. africanumn, M. canetti, M. caprae, M. microti, M. pinnipedii, M. aviumn, M. aviumn paratuberculosis, M. aviumn silvaticumn, M. aviumn "homninissuis", M. colombiense, M. asiaticumn, M. gordonae, M. gastri, M. kansasii, M. hiberniae, M. nonchromnogenicunm, M. terrae, M. triviale, M. ulcerans, M. pseudoshottsii, M. shottsii, M. triplex, M. genavense, M. florentinun, M. lentiflavumn, M. palustre, M. kubicae, M. parascrofulaceumn, M. heidelbergense, M. interjectumn, M. simniae, M. branderi, M. cookii, M. celatumn, M. bohemnicumn, M. haemnophilumn, M. malmoense, M. szulgai, M. leprae, M. lepraemnuriumn, M. lepromnatosis, M. botniense, M. chimaera, M. conspicuunm, M. doricumn, M. farcinogenes, M. heckeshornense, M. intracellulare, M. lacus, M. marinumn, M. monacense, M. montejiorense, M. murale, M. nebraskense, M. saskatchewanense, M. scrofulaceumn, M. shimnoidei, M. tusciae, M. xenopi, M. intermediumn, M. abscessus, M. chelonae, M. bolletii, M. fortuitun, M. fortuitun* subsp. *acetamidolyticumn, M. boenickei, M. peregrinumn, M. porcinumn, M. senegalense, M. septicumn, M. neworleansense, M. houstonense, M. mucogenicumn, M. mageritense, M. brisbanense, M. cosmeticumn, M. parafortuitumn, M. austroafricanumn, M. diernhoferi, M. hodleri, M. neoaurum, M. frederiksbergense, M. aurum, M. vaccae, M. chitae, M. fallax, M. confluentis, M. flavescens, M.* madagascariense, M. phlei, M. smegmatis, M. goodii, M. wolinskyi, M. thermoresistibile, M. gadium, M. komossense, M. obuense, M. sphagni, M. agri, M. aichiense, M. alvei, M. arupense, M. brumae, M. canariasense, M. chubuense, M. conceptionense, M. duvalii, M. elephantis, M. gilvum, M. hassiacum, M. holsaticum, M. immunogenum, M. massiliense, M. moriokaense, M. psychrotolerans, M. pyrenivorans, M. vanbaalenii, M. pulveris, M. arosiense, M. aubagnense, M. caprae, M. chlorophenolicum, M. fluoroanthenivorans, M. kumamotonense, M. novocastrense, M. parmense, M. phocaicum, M. poriferae, M. rhodesiae, M. seoulense, and M. tokaiense.

In a screen of the top 40 inhibitors of PFOR against several strains of Mycobacterium tuberculosis, we identified six compound classes displaying anti-TB activity. It is important to note that TB is one of the leading causes of morbidity and mortality worldwide and in particular in HIV positive individuals. There have been few new antimicrobials developed for the treatment of TB and resistance to first line therapeutics isoniazide (NH) and rifampicin (Rif) are common strains displaying multi-(MDR) and extended-(XDR) drug resistance have become a major problem in developing countries. While there is a worldwide effort to develop new therapeutics, few of the current ones will become first line drugs because of resistance issues. Target-based and high throughput screens of chemical libraries against empiric targets have all failed to deliver the next generation of therapeutics.

We have always believed that drugs exhibiting broad-spectrum activity against Gram-positive bacteria might also be active against TB organisms, based on common evolution and of shared general physiology. Of the six compounds displaying potency against TB strains including MDR and XDR strains, three are derivatives of dinitrothiophene and two are derived from 4-chloro-5-nitrothiazole. The structures of these derivatives are distinctly different from nitazoxanide, which has recently been demonstrated to have activity against TB organisms. However, NTZ action against TB is inhibited by proteins that would be found in serum. In our MIC screen, promising compounds must overcome the inhibitory action of serum. By setting this bar high, we eliminate unproductive leads such as nitazoxanide.

TABLE 1

Example 1- Confirmation of compound activities against *M. tuberculosis* using agar proportion method

| No. | VPC Compound Id. No. | % Inhibit growth at 5 mg/ml H37Rv | Susceptible | MDR | XDR |
|---|---|---|---|---|---|
| 1 | 161180 | 80% | 0% | 0% | 50% |
| 2 | 161183 | 80% | 60% | 70% | 50% |
| 3 | 162047 | 95% | 60% | 92% | 50% |
| 4 | 162080 | 90% | 73% | 95% | 90% |
| 5 | 162087 | 97% | 97% | 100% | 100% |
| 6 | 162088 | 70% | 0% | 90% | 70% |
| 7 | 16a1011 | 50% | 0% | 0% | 0% |
| 8 | 16a1060 | 90% | 90% | 98% | 90% |
| 9 | 16b1089 | 0% | 0% | 0% | 0% |
| 10 | 16b1090 | 100% | 100% | 100% | 100% |
| 11 | 16b1092 | 100% | 100% | 100% | 100% |
| 12 | 16b1093 | 98% | 96% | 100% | 100% |
| 13 | 16b1094 | 100% | 100% | 100% | 100% |

It was found that the most potent compounds are 10, 11, and 13, which are dinitro-thiophenes. Compounds 4, 5 and 6 are 4-chloro-5-nitrothiazolides. Compound 8 is NTZ with modifications to the benzene ring.

TABLE 2

Example 1 - MIC of three exemplary compounds using agar proportion method

| Isolates | Isoniazid | Rifampin | VPC Compounds- MIC mg/ml 16b1090 | 16b1092 | 16b1094 |
|---|---|---|---|---|---|
| H37Rv (Reference) | ≤0.125 | ≤0.125 | 4 | 2 | 4 |
| 283 (susceptible) | ≤0.125 | ≤0.125 | 4 | 2 | 4 |
| 234 (MDR-TB) | 16 | 16 | 4 | 2 | 4 |
| 565 (MDR-TB) | 8 | ≥32 | 4 | 2 | 4 |
| 694 (MDR-TB) | 16 | ≥32 | 2 | 1 | 4 |
| 750 (MDR-TB) | 8 | ≥32 | 4 | 2 | 4 |
| 971 (MDR-TB) | 4 | ≥32 | 2 | 2 | 4 |
| 823 (XDR-TB) | 8 | ≥32 | 4 | 2 | 4 |

MIC testing of eight strains of *Mycobacterium tuberculosis* including MDR and XDR strains with the three most active compounds. Note that INH and Rif resistant strains remain susceptible to all three drugs.

Activity Against Non-Tuberculosis Mycobacteria

The strains used were *Mycobacterium smegmatis* mc2155, *Mycobacterium chelonae* EOP-1, *Mycobacterium marinum* ATCC 927, *Mycobacterium avium* Va14(T), and *Mycobacterium abscessus* AAy-P-1. The medium use was Middlebrook 7H9 containing 0.5% (vol/vol) glycerol and 10% (vol/vol) oleic acid-albumin. Incubation Temperature was 37° C., except for *M. marinum* at 30° C. For nitazoxanides, precipitates were present in wells of nitazoxanides with high concentrations (250-31 μg/mL) except for 162080, 162088, 16b2026, and 16b2031. Fortunately, the presence of precipitate did not obscure identification of MIC values.

Decolorization: Almost all the yellow nitazoxanides, namely 16b1090, 16b1092 and 16b1093, 16b1094, 16b2023, 16b2025, and 16b2026 were decolorized by *M. smegmatis* strain mc2155. None of the other mycobacterial strains decolorized the compounds.

The results are provided below in Table 3, Example 3.

TABLE 3

Example 1 - Anti-Mycobacterial Activity of Nitazoxanides (μg/mL)

| Nitazoxanide | Minimal Inhibitory Concentration (μg/mL) *M. smegmatis* | *M. chelonae* | *M. marinum* | *M. avium* | *M. abscessus* |
|---|---|---|---|---|---|
| 162080 | 125 | 16 | 16 | 125 | 0.25 |
| 162087 | 31 | 16 | 16 | 125 | >250 |
| 162088 | 31 | 63 | 31 | 250 | 0.5 |
| 16b1089 | 125 | 31 | 16 | 63 | 4. |
| 16b1090 | 16 | 1 | 4 | 8 | 0.5 |
| 16b1092 | 31 | 4 | 4 | 8 | 0.25 |
| 16b1093 | 125 | 2 | 31 | 31 | 1. |
| 16b1094 | 16 | 2 | 4 | 16 | 2. |
| 16b2023 | 63 | 4 | 8 | 31 | 1. |
| 16b2025 | 63 | 8 | 16 | 31 | 0.25 |
| 16b2026 | 31 | 4 | 8 | 16 | 0.25 |
| 16b2028 | 250 | 8 | 8 | 63 | 0.25 |
| 16b2031 | 63 | 125 | 16 | 63 | 250 |
| Nitazoxanide | >250 | 63 | 31 | 250 | 63 |

Other methods and techniques useful for this invention can be found in PCT/US2010/027397, filed Mar. 16, 2010, which claims priority to U.S. Provisional Patent Application 61/161,796, filed Mar. 20, 2009.

Provided below are general methods as well as compounds and their synthesis as reproduced from Hoffman et al. (PCT/US2010/027397).

General Materials and Methods and Preparation of Compounds

Bacterial Strains and Growth Conditions.

Bacterial strains, unless otherwise specified, were grown in Trypticase soy broth or agar (TSB or TSA, respectively) at 37° C. with shaking for liquid cultures. All strains were stored at −80° C. in 15% glycerol.

Determination of MIC—

Minimal inhibitory concentration testing of NTZ was done in sterile round bottom 96 well microtiter polystyrene plates (Corning Inc., Corning, N.Y.) by microdilution. Tizoxanide TIZ (deacetylated form of NTZ), denitro-NTZ (TIZ without 5-nitro group) and amoxanide AMIX (TIZ-ethylamine) were also tested. Bacteria were grown overnight and suspended in fresh TSB to an $OD_{600}$ of 0.01 and 100 µl were dispensed into wells with the first well containing 200 µl. NTZ and other antibiotics (DMSO control) were added to well one and serially diluted from 32 g/ml. All compounds were tested in triplicate and plates were read visually or with a plate reader (Molecular Devices) at 8, 12 and at 24 h. MIC was determined as the first well in which no visible bacterial growth was noted relative to controls. Drug effects on aerobic growth were determined in 125 ml flasks containing 25 ml of TSB medium and following inoculation (detailed above), flasks were on a gyrorotary shaker (200 rpm) at 37° C. Final concentrations of NTZ were 0, 10 and 25 µg/ml and samples were removed at hourly intervals and absorbance determined at 600 nm.

General Experimental Procedures and Preparation of Compounds:

General Considerations:

All reagents were purchased from commercially available sources and used as is without further purification. All reactions were run under a nitrogen or argon atmosphere unless otherwise noted. Flash silica gel chromatography was performed with 60 Å mesh standard grade silica gel (Sortech). $^1H$ and $^{13}C$ NMR spectra were obtained using Varian 300 MHz or 500 MHz spectrometers and recorded at 23° C. Chemical shifts (s=singlet, bs=broad singlet, d=doublet, dd=doublet of doublets, dt=doublet of triplets, t=triplet, tt=triplet of triplets, m=multiplet) are given in parts per million relative to DMSO-$d_6$ (δ 2.50) for proton spectra and relative to DMSO-$d_6$ (δ 39.51) for carbon spectra. Mass spectra were obtained at the NCSU Department of Chemistry Mass Spectrometry Facility which is funded by the North Carolina Biotechnology Center and the NCSU Department of Chemistry.

Method A: Acid Chloride Amide Coupling:

Acid chloride (100 mg, 0.1 mL, 1 eq) was dissolved in THF (0.1M) and cooled to −78° C. then amino-heterocycle (1 eq) was added in one portion. DIPEA (1.1 eq) was added to the resulting slurry at −78° C. and the solution was held at this temperature for 10 mins then allowed to warm to room temperature overnight. The solution was judged complete by TLC analysis (~24 h) and was diluted with EtOAc (30 mL) and washed with sat. $NaHCO_3$ (3×20 mL), 1M HCl (3×20 mL) and brine (2×20 mL) then dried ($MgSO_4$) followed by filtration and evaporation to dryness. The resulting residue was purified by gradient flash column chromatography (10-60% EtOAc/hexanes or 1-2% MeOH/$CH_2Cl_2$) to obtain the product.

Method B: Carboxylic Acid EDC Amide Coupling:

Carboxylic acid (100 mg, 1 eq), EDC (2 eq), HOBT (2 eq) and DIPEA (3 eq) were dissolved in THF (0.1M) and stirred for 15 mins. Amino-heterocycle (1 eq) was then added in one portion and the reaction was stirred at ambient temperature. Once judged complete by TLC analysis (~24 h), the resulting suspension was diluted with EtOAc (30 mL) and washed with sat. $NaHCO_3$ (3×20 mL), 1M HCl (3×20 mL) and brine (2×20 mL) then dried ($MgSO_4$) followed by filtration and evaporation to dryness. The resulting residue was purified by gradient flash column chromatography (10-60% EtOAc/hexanes) to obtain the product.

Method C: Aromatic Alcohol Alkylation:

Aromatic alcohol (2.0 mL, 1 eq) was dissolved in DMF (0.3M) then finely ground $K_2CO_3$ (2 eq) and Boc-aminoethylbromide (1.5 eq) were added. The solution was warmed to 65° C. and stirred for 3 days then concentrated to near dryness. Water was then added and the resulting slurry was extracted with EtOAc (3×40 mL) The organic layers were combined and washed with $H_2O$ (2×20 mL), 5% LiCl (2×20 mL) and brine (2×20 mL) then dried ($MgSO_4$) followed by filtration and evaporation to dryness to obtain the product.

Method D: Alkyl Ester Saponification:

Ester (240 mg, 1 eq) was dissolved in a mixture of MeOH:THF:$H_2O$ (1M:1M:1M) then LiOH.$H_2O$ (3 eq) was added. The solution was stirred for 24 hours then was quenched with 1M HCl (20 mL) and extracted with EtOAc (4×15 mL). The combined organic layers were then washed with brine (2×20 mL) then dried ($MgSO_4$) followed by filtration and evaporation to dryness to obtain the product.

Method E: Boc-Group Deprotection and HCl Salt Exchange:

Boc-Amine (1 eq) was suspended in anhydrous $CH_2Cl_2$ (0.02M) and cooled to 0° C. TFA (0.2M) was charged into the flask and the reaction stirred overnight. After that time the reaction was evaporated to dryness and hexanes was added. Again the mixture was concentrated and the process repeated. The resulting TFA salt was dissolved in $CH_2Cl_2$ and 2M HCl in $Et_2O$ (0.15M) was added followed by cold $Et_2O$. The precipitate was collected by filtration and washed with $Et_2O$ to obtain the title compound.

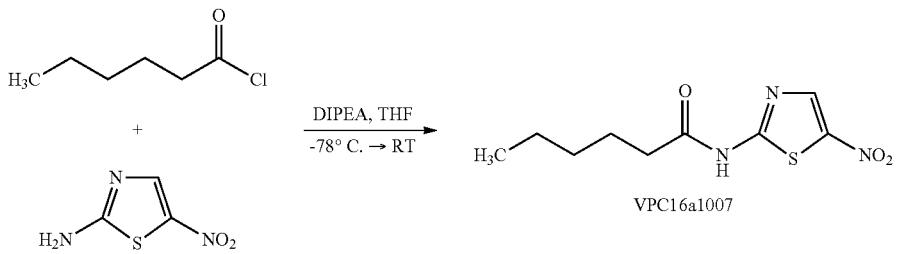

N-(5-Nitrothiazol-2-yl)hexanamide (VPC16a1007)

Method A yielded the title compound VPC16a1007 (126 mg, 71%) as a light orange solid. $^1$H NMR (500 MHz, DMSO-$d_6$) δ 13.02 (s, 1H), 8.57 (s, 1H), 2.50 (t, J=7.5 Hz, 2H), 1.67-1.44 (m, 2H), 1.44-1.07 (m, 4H), 0.85 (t, J=7.0 Hz, 3H); $^{13}$C NMR (125 MHz, DMSO-$d_6$) δ 173.1, 161.7, 142.6, 141.6, 34.9, 30.7, 24.0, 21.8, 13.8; HRMS (ESI) calcd for $[C_9H_{13}N_3O_3S+H]^+$ 244.0750. found 244.0757.

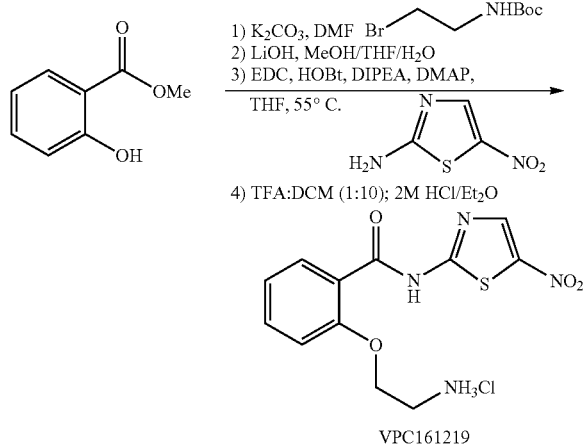

VPC161219

2-(2-Aminoethoxy)-N-(5-nitrothiazol-2-yl)benzamide hydrochloride (VPC161219)

Method C with methyl 2-hydroxybenzoate (2.0 mL, 15.4 mmol) afforded methyl 2-(2-(tert-butoxycarbonylamino)ethoxy)benzoate (4.55 g, 99%) as an amber oil. $^1$H NMR (300 MHz, DMSO-$d_6$) δ 7.64 (dd, J=7.6, 1.1 Hz, 1H), 7.57-7.45 (m, 1H), 7.14 (d, J=8.4 Hz, 1H), 7.02 (t, J=7.5 Hz, 1H), 6.83 (t, J=5.3 Hz, 1H), 4.03 (t, J=5.9 Hz, 2H), 3.79 (s, 3H), 3.31 (q, J=5.8 Hz, 2H), 1.38 (s, 9H); $^{13}$C NMR (75 MHz, DMSO-$d_6$) δ 157.4, 155.6, 133.4, 130.7, 120.6, 120.5, 114.0, 77.8, 67.4, 51.8, 39.3, 31.4, 28.2, 27.6; HRMS (ESI) calcd for $[C_{15}H_{21}NO_5+Na]^+$ 318.1312. found 318.1319. Method D with ethyl 2-(2-(tert-butoxycarbonylamino)ethoxy)benzoate (240 mg, 0.81 mmol) afforded 2-(2-(tert-butoxycarbonylamino)ethoxy)benzoic acid (221 mg, 97%) as a white solid. $^1$H NMR (300 MHz, DMSO-$d_6$) δ 12.56 (s, 1H), 7.65 (dd, J=7.6, 1.7 Hz, 1H), 7.48 (td, J=8.3, 1.7 Hz, 1H), 7.13 (d, J=8.4 Hz, 1H), 7.01 (t, J=7.5 Hz, 1H), 6.85 (t, J=5.3 Hz, 1H), 1.37 (s, 9H); $^{13}$C NMR (75 MHz, DMSO-$d_6$) δ 167.3, 157.3, 155.7, 133.1, 130.8, 121.7, 120.6, 114.1, 77.9, 67.6, 39.2, 28.2; HRMS (ESI) calcd for $[C_{14}H_{19}NO_5+Na]^+$ 304.115. found 304.1168. Method B with 2-(2-(tert-butoxycarbonylamino)ethoxy)benzoic acid (100 mg, 0.36 mmol) and cat. DMAP afforded tert-butyl 2-(2-(5-nitrothiazol-2-ylcarbamoyl)phenoxy)ethylcarbamate (56 mg, 38%) as a beige solid. $^1$H NMR (300 MHz, DMSO-$d_6$) δ 12.75 (s, 1H), 8.69 (s, 1H), 7.71 (dd, J=7.6, 1.7 Hz, 1H), 7.66-7.53 (m, 1H), 7.24 (d, J=8.4 Hz, 1H), 7.08 (dt, J=10.9, 6.4 Hz, 1H), 4.15 (t, J=5.7 Hz, 2H), 3.37 (q, J=5.6 Hz, 2H), 1.34 (s, 9H); $^{13}$C NMR (75 MHz, DMSO-$d_6$) δ 165.7, 161.6, 156.5, 155.7, 142.8, 141.9, 134.2, 130.6, 121.0, 120.9, 113.2, 77.9, 67.6, 39.2, 28.2; HRMS (ESI) calcd for $[C_{17}H_{20}N_4O_6S+H]^+$ 409.1176. found 409.1189. Method E with tert-butyl 2-(2-(5-nitrothiazol-2-ylcarbamoyl)phenoxy)ethylcarbamate (32 mg, 0.07 mmol) afforded the title compound VPC161219 (27 mg, 99%) as a tan solid. $^1$H NMR (300 MHz, DMSO-$d_6$) δ 12.94 (s, 1H), 8.71 (s, 1H), 8.24 (s, 3H), 7.69 (dd, J=7.6, 1.4 Hz, 1H), 7.66-7.57 (m, 1H), 7.25 (d, J=8.4 Hz, 1H), 7.15 (t, J=7.5 Hz, 1H), 4.35 (t, J=4.8 Hz, 3H), 3.24 (q, J=4.3 Hz, 2H); $^{13}$C NMR (75 MHz, DMSO-$d_6$) δ 165.8, 161.8, 155.7, 142.8, 141.9, 134.1, 130.8, 121.6, 121.3, 113.2, 65.2, 38.2; HRMS (ESI) calcd for $[C_{12}H_{12}N_4O_4S+H]^+$ 309.0652. found 309.0666.

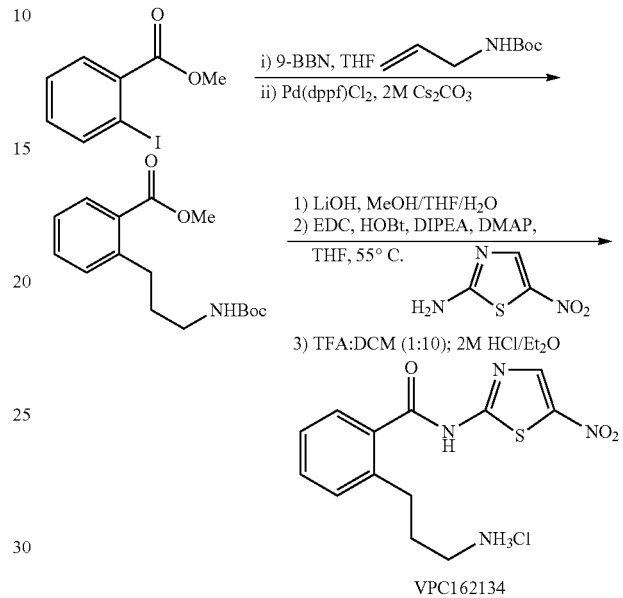

VPC162134

2-(3-Aminopropyl)-N-(5-nitrothiazol-2-yl)benzamide hydrochloride (VPC162134)

tert-Butyl allylcarbamate (113 mg, 0.72 mmol) and THF (1.5 mL) were charged into a flame-dried round bottom flask followed by the dropwise addition of 0.5M 9-BBN in THF (1.92 mL). After 2 h, 2M $Cs_2CO_3$ (0.72 mL), methyl 2-iodobenzoate (0.07 mL, 0.48 mmol) and Pd(dppf)$Cl_2$ (27.7 mg, 5 mol %) were added to the flask and held at room temperature. Once judged complete my TLC (~24 h), the crude mixture was diluted with EtOAc (30 mL) and washed with sat. $NH_4Cl$ (2×20 mL) and brine (2×20 mL) then dried ($MgSO_4$) followed by filtration and evaporation to dryness. The resulting residue was purified by gradient flash column chromatography (5-30% EtOAc/hexanes) to obtain methyl 2-(3-(tert-butoxycarbonylamino)propyl)benzoate (130 mg, 93%) as an amber oil. $^1$H NMR (500 MHz, DMSO-$d_6$) δ 7.76 (dd, J=7.8, 1.1 Hz, 1H), 7.49 (td, J=7.5, 1.4 Hz, 1H), 7.34-7.28 (m, 2H), 6.85 (t, J=5.4 Hz, 1H), 3.82 (s, 3H), 2.93 (q, J=6.7 Hz, 2H), 2.86-2.79 (m, 2H), 1.65-1.58 (m, 2H), 1.37 (s, 9H); $^{13}$C NMR (125 MHz, DMSO-$d_6$) δ 167.5, 155.57, 143.0, 132.0, 130.9, 130.1, 129.4, 126.1, 77.4, 52.0, 39.8, 31.6, 31.0, 28.3; HRMS (ESI) calcd for $[C_{16}H_{23}NO_4+Na]^+$ 316.1519. found 316.1152. Method D with methyl 2-(3-(tert-butoxycarbonylamino)propyl)benzoate (130 mg, 0.45 mmol) afforded 2-(3-(tert-butoxycarbonylamino)propyl)benzoic acid (120 mg, 96%) as a white solid. $^1$H NMR (500 MHz, DMSO-$d_6$) δ 12.82 (bs, 1H), 7.77 (dd, J=7.7, 1.1 Hz, 1H), 7.45 (td, J=7.5, 1.3 Hz, 1H), 7.33-7.24 (m, 2H), 6.81 (t, J=5.3 Hz, 1H), 3.00-2.83 (m, 4H), 1.78-1.53 (m, 2H), 1.37 (s, 9H); $^{13}$C NMR (125 MHz, DMSO-$d_6$) δ 168.8, 155.6, 142.9, 131.6, 130.8, 130.5, 130.2, 125.9, 77.4, 31.5, 30.9, 28.3; HRMS (ESI) calcd for $[C_{15}H_{21}NO_4+Na]^+$ 302.1363. found 302.1359. Method B with 2-(3-(tert-butoxycarbonylamino)propyl)benzoic acid (95 mg, 0.34 mmol) and cat. DMAP at 55° C. afforded tert-butyl 3-(2-(5-nitrothiazol-2-ylcarbamoyl)phenyl)propylcarbamate (58 mg, 42%) as a light yellow solid. ¹H NMR (500 MHz, DMSO-d₆) δ 13.54 (bs, 1H), 8.69 (s, 1H), 7.60 (d, J=7.6 Hz, 1H), 7.51 (t, J=7.6 Hz, 1H), 7.43-7.32 (m, 2H), 6.81 (t, J=5.5 Hz, 1H), 2.91 (q, J=6.5 Hz, 2H), 2.79-2.67 (m, 2H), 1.74-1.40 (m, 2H), 1.34 (s, 9H); ¹³C NMR (125 MHz, DMSO-d₆) δ 168.7, 162.0, 155.5, 142.6, 142.0, 141.2, 132.3, 131.5, 130.2, 128.5, 125.9, 77.3, 39.6, 31.5, 30.0, 28.2; HRMS (ESI) calcd for [C₁₈H₂₂N₄O₅S+Na]⁺429.1203. found 429.1201. Method E with tert-butyl 3-(2-(5-nitrothiazol-2-ylcarbamoyl)phenyl)propylcarbamate (310 mg, 0.76 mmol) afforded the title compound VPC162134 (257 mg, 98%) as a beige solid. ¹H NMR (500 MHz, DMSO-d₆) δ 13.60 (s, 1H), 8.71 (s, 1H), 8.05 (bs, 3H), 7.65 (d, J=7.7 Hz, 1H), 7.55 (t, J=7.6 Hz, 1H), 7.47-7.35 (m, 2H), 2.81 (t, J=7.5 Hz, 2H), 2.79-2.71 (m, 2H), 1.87 (quint., J=7.5 Hz, 2H); ¹³C NMR (125 MHz, DMSO-d₆) δ 168.6, 162.1, 142.7, 142.0, 140.3, 132.2, 131.7, 130.2, 128.8, 126.3, 38.4, 29.6, 28.9; HRMS (ESI) calcd for [C₁₃H₁₄N₄O₃S+H]⁺307.0859. found 307.0855.

3-(2-Aminoethoxy)-N-(5-nitrothiazol-2-yl) thiophene-2-carboxamide hydrochloride (VPC162125)

Method C with methyl 3-hydroxythiophene-2-carboxylate (1.0 g 6.32 mmol) afforded methyl 3-(2-(tert-butoxycarbonylamino)ethoxy)thiophene-2-carboxylate (1.9 g, 100%) as an amber oil. ¹H NMR (500 MHz, DMSO-d₆) δ 7.81 (d, J=5.5 Hz, 1H), 7.11 (d, J=5.5 Hz, 1H), 6.91 (t, J=5.5 Hz, 1H), 4.12 (t, J=6.0 Hz, 2H), 3.72 (s, 3H), 3.27 (q, J=5.9 Hz, 2H), 1.37 (s, 9H); ¹³C NMR (125 MHz, DMSO-d₆) δ 161.3, 160.9, 155.6, 132.0, 118.2, 108.7, 77.9, 70.0, 51.4, 39.4, 28.2; HRMS (ESI) calcd for [C₁₃H₁₉NO₅S+Na]⁺324.0876. found 324.0877. Method D with methyl 3-(2-(tert-butoxycarbonylamino)ethoxy)thiophene-2-carboxylate (70 mg, 0.23 mmol) afforded 3-(2-(tert-butoxycarbonylamino)ethoxy)thiophene-2-carboxylic acid (63 mg, 95%) as a white solid. ¹H NMR (500 MHz, DMSO-d₆) δ 12.43 (bs, 1H), 7.74 (d, J=5.5 Hz, 1H), 7.08 (d, J=5.5 Hz, 1H), 6.91 (t, J=5.5 Hz, 1H), 4.10 (t, J=6.1 Hz, 2H), 3.25 (q, J=6.0 Hz, 2H), 1.37 (s, J=12.2 Hz, 9H); ¹³C NMR (125 MHz, DMSO-d₆) δ 162.4, 160.3, 155.7, 131.3, 118.4, 110.5, 77.9, 70.0, 39.5, 28.2; HRMS (ESI) calcd for [C₁₂H₁₇NO₅S+Na]⁺310.0720. found 310.0719. Method B with 3-(2-(tert-butoxycarbonylamino)ethoxy)thiophene-2-carboxylic acid (100 mg, 0.35 mmol) and cat. DMAP at 55° C. afforded tert-butyl 2-(2-(5-nitrothiazol-2-ylcarbamoyl) thiophen-3-yloxy)ethylcarbamate (100 mg, 69%) as a beige solid. ¹H NMR (500 MHz, DMSO-d₆) δ 11.30 (bs, 1H), 8.67 (s, 1H), 8.06 (d, J=5.5 Hz, 1H), 7.29-7.22 (m, 2H), 4.34 (t, J=5.1 Hz, 2H), 3.39 (q, J=5.2 Hz, 2H), 1.33 (s, 9H); ¹³C NMR (125 MHz, DMSO-d₆) δ 160.9, 159.4, 159.1, 155.8, 142.5, 142.2, 134.9, 117.7, 78.0, 71.9, 39.4, 28.1; HRMS (ESI) calcd for [C₁₅H₁₈N₄O₆S₂+H]⁺415.0741. found 415.0745. Method E with tert-butyl 2-(2-(5-nitrothiazol-2-ylcarbamoyl) thiophen-3-yloxy)ethylcarbamate (25 mg, 0.06 mmol) afforded the title compound VPC162125 (21 mg, 100%) as a light yellow solid. ¹H NMR (500 MHz, DMSO-d₆) δ 11.62 (bs, 1H), 8.70 (bs, 1H), 8.51 (bs, 3H), 8.07 (bs, 1H), 7.27 (bs, 1H), 4.52 (bs, 2H), 3.26 (bs, 2H); ¹³C NMR (125 MHz, DMSO-d₆) δ 160.9, 159.3, 157.8, 142.4, 141.9, 134.8, 117.5, 111.8, 68.7, 38.2; HRMS (ESI) calcd for [C₁₀H₁₀N₄O₄S₂+H]⁺315.0216. found 315.0217.

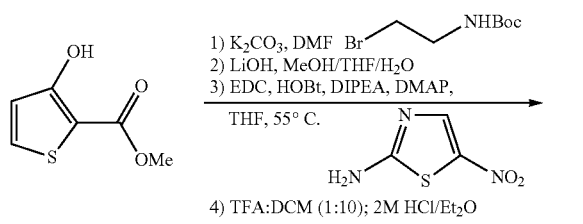

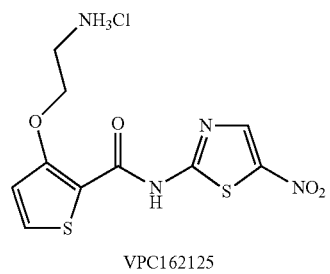

VPC162125

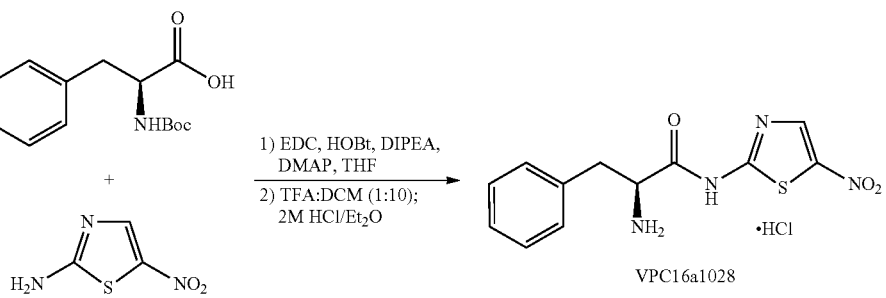

(S)-2-Amino-N-(5-nitrothiazol-2-yl)-3-phenylpropanamide hydrochloride (VPC16a1028)

Method B with Boc-L-phenylalanine (100 mg, 0.38 mmol) afforded (S)-tert-butyl-1-(5-nitrothiazol-2-ylamino)-1-oxo-3-phenylpropan-2-ylcarbamate (107 mg, 72%) as a beige solid. $^1$H NMR (300 MHz, DMSO-$d_6$) δ 13.37 (s, 1H), 8.64 (s, 1H), 7.44 (d, J=7.5 Hz, 1H), 7.35-7.18 (m, 5H), 4.47 (bs, 1H), 3.03 (dd, J=13.6, 4.3 Hz, 1H), 2.92-2.75 (m, 1H), 1.31 (s, 9H); $^{13}$C NMR (75 MHz, DMSO-$d_6$) δ 173.0, 161.5, 155.5, 142.7, 142.0, 137.2, 129.3, 128.2, 126.6, 78.5, 56.2, 36.5, 28.1; HRMS (ESI) calcd for $[C_{17}H_{20}N_4O_5S+Na]^+$415.1047. found 415.1057. Method E with (S)-tert-butyl-1-(5-nitrothiazol-2-ylamino)-1-oxo-3-phenylpropan-2-ylcarbamate (30 mg, 0.08 mmol) afforded the title compound VPC16a1028 (25 mg, 99%) as a brown solid. $^1$H NMR (500 MHz, DMSO-$d_6$) δ 13.83 (bs, 1H), 8.71 (bs, 3H), 8.67 (s, 1H), 7.35-7.30 (m, 2H), 7.27 (t, J=8.5 Hz, 3H), 4.44 (t, J=6.4 Hz, 1H), 3.24 (dd, J=13.8, 6.4 Hz, 1H), 3.17 (dd, J=13.8, 7.5 Hz, 1H); $^{13}$C NMR (125 MHz, DMSO-$d_6$) δ 169.0, 160.6, 142.5, 134.1, 129.5, 128.7, 127.4, 53.8, 36.5; HRMS (ESI) calcd for $[C_{12}H_{12}N_4O_3S+H]^+$292.0703. found 292.0711.

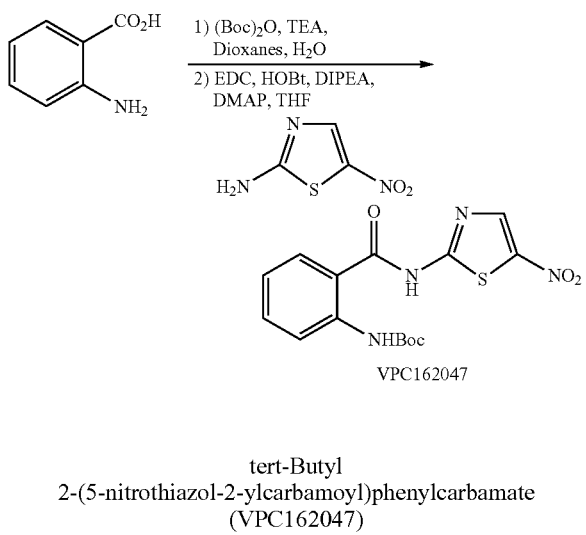

tert-Butyl 2-(5-nitrothiazol-2-ylcarbamoyl)phenylcarbamate (VPC162047)

Method B with 2-(tert-butoxycarbonylamino)benzoic acid [1], (100 mg, 0.42 mmol) and catalytic DMAP in DMF (in place of THF) afforded the title compound VPC162047 (108 mg, 71%) as a beige solid. $^1$H NMR (300 MHz, DMSO-$d_6$) δ 13.47 (bs, 1H), 9.65 (s, 1H), 8.69 (s, 1H), 7.77 (d, J=7.7 Hz, 1H), 7.70 (d, J=8.2 Hz, 1H), 7.55 (t, J=7.7 Hz, 1H), 7.19 (t, J=7.6 Hz, 1H), 1.39 (s, 9H); $^{13}$C NMR (75 MHz, DMSO-$d_6$) δ 167.9, 162.6, 152.7, 142.5, 141.7, 138.2, 132.9, 129.4, 122.7, 122.4, 121.4, 79.8, 27.9; HRMS (ESI) calcd for $[C_{15}H_{16}N_4O_5S+H]^+$387.0734. found 387.0745.

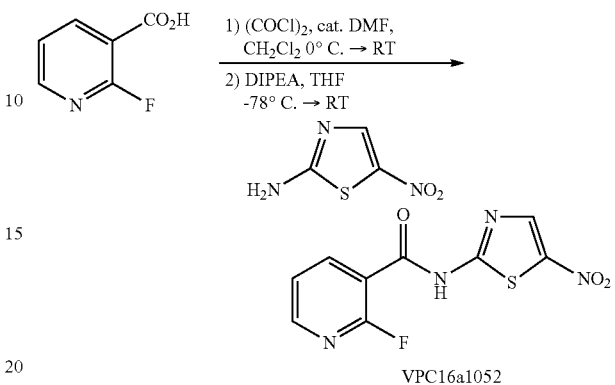

2-Fluoro-N-(5-nitrothiazol-2-yl)nicotinamide (VPC16a1052)

2-Fluoronicotinic acid (100 mg, 0.71 mmol) was dissolved in $CH_2Cl_2$ (2 mL) with a drop of DMF (catalytic) and cooled to 0° C. then $(COCl)_2$ (0.18 mL, 2.12 mmol) was added dropwise to the stirring solution. The slurry was allowed to warm to room temperature for 2 hours then concentrated to dryness using hexanes to remove the excess $(COCl)_2$. The resulting acid chloride was dissolved in THF (7 mL) and DIPEA (0.26 mL, 1.49 mmol) was added. The solution was cooled to −78° C. and 2-amino-5-nitrothiazole (108 mg, 0.78 mmol) was then added in one portion and the solution was held at −78° C. for 10 mins then warmed to room temperature and stirred for 2 days until judged complete by TLC analysis. The resulting suspension was quenched with 2M HCl in $Et_2O$ (0.78 mL, 1.56 mmol) and concentrated to dryness then purified by flash column chromatography (1% MeOH/$CH_2Cl_2$) to obtain the title compound VPC16a1052 (118 mg, 62%) as a yellow solid. $^1$H NMR (300 MHz, DMSO-$d_6$) δ 13.77 (bs, 1H), 8.70 (s, 1H), 8.54-8.44 (m, 1H), 8.41-8.35 (m, 1H), 7.63-7.50 (m, 1H); $^{13}$C NMR (75 MHz, DMSO-$d_6$) δ 163.0 (d, $J_{CF}$=5.9 Hz), 161.5, 159.4 (d, $J_{CF}$=242 Hz), 151.3 (d, $J_{CF}$=15.2 Hz), 142.4, 142.3, 122.3 (d, $J_{CF}$=4.1 Hz), 115.9 (d, $J_{CF}$=28.5 Hz); HRMS (ESI) calcd for $[C_9H_5FN_4O_3S+H]^+$ 269.0139. found 269.0143.

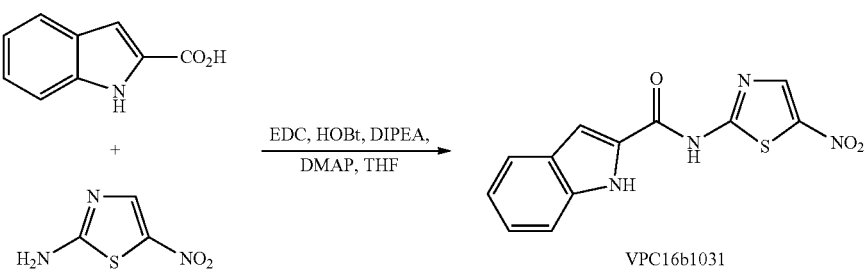

N-(5-Nitrothiazol-2-yl)-1H-indole-2-carboxamide (VPC16b1031)

Method B with 1H-indole-2-carboxylic acid (75 mg, 0.47 mmol) with cat. DMAP afforded the title compound VPC16b1031 (92 mg, 69%) as an orange solid. $^1$H NMR (500 MHz, DMSO-$d_6$) δ 13.65 (s, 1H), 12.10 (s, 1H), 8.69 (s, 1H), 7.76 (s, 1H), 7.70 (d, J=8.0 Hz, 1H), 7.48 (d, J=8.2 Hz, 1H), 7.29 (t, J=7.5 Hz, 1H), 7.10 (t, J=7.4 Hz, 1H); $^{13}$C NMR (125 MHz, DMSO-$d_6$) δ 162.4, 160.1, 142.8, 141.9, 137.9, 128.1, 126.8, 125.3, 122.5, 120.5, 112.6, 107.6; HRMS (ESI) calcd for $[C_{12}H_8N_4O_3S+H]^+$289.0390. found 289.0396.

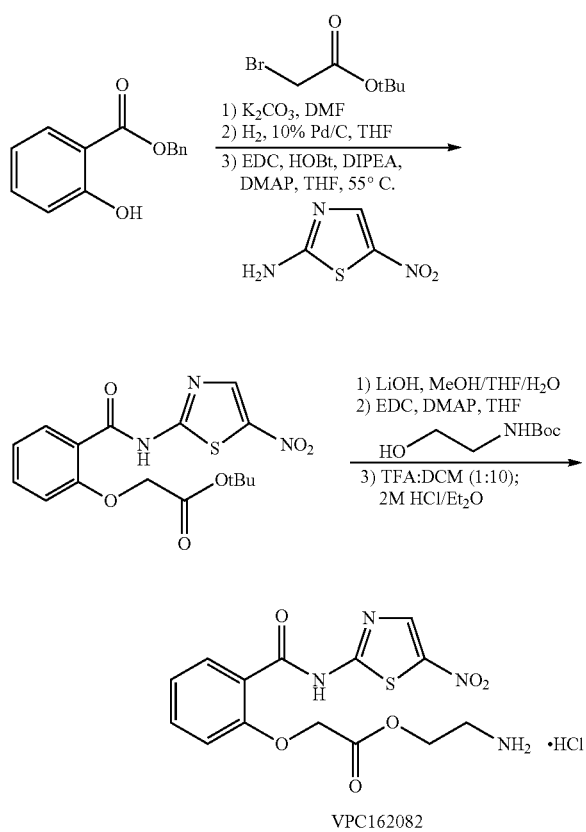

2-Aminoethyl 2-(2-(5-nitrothiazol-2-ylcarbamoyl) phenoxy)acetate hydrochloride (VPC162082)

Method C with benzyl 2-hydroxybenzoate (1.05 mL, 5.2 mmol) and tert-butyl 2-bromoacetate (in place of Boc-aminoethylbromide) afforded benzyl 2-(2-tert-butoxy-2-oxoethoxy)benzoate (1.82 g, 98%) as a amber oil. $^1$H NMR (300 MHz, DMSO-$d_6$) δ 7.69 (dd, J=7.6, 1.3 Hz, 1H), 7.65-7.42 (m, 3H), 7.42-7.19 (m, 3H), 7.13-6.97 (m, 2H), 5.31 (s, 2H), 4.76 (s, 2H), 1.40 (s, 9H); $^{13}$C NMR (75 MHz, DMSO-$d_6$) δ 167.4, 165.4, 156.7, 136.2, 133.3, 130.7, 128.4, 127.9, 127.7, 120.8, 120.5, 113.5, 81.5, 65.9, 65.5, 27.6; HRMS (ESI) calcd for $[C_{20}H_{22}O_5+Na]^+$365.1359. found 365.1367. To a solution of anhydrous THF (42 mL) and 10% Pd/C (0.15 g) was charged benzyl 2-(2-tert-butoxy-2-oxoethoxy)benzoate (1.56 g, 4.29 mmol). Air was removed from the system and the reaction was back flushed with hydrogen. This process was repeated three times before setting the reaction under a hydrogen balloon at atmospheric pressure and temperature for 22 h. After that time the reaction was filtered through a Celite® pad and the filter cake was washed with THF (20 mL). The filtrate was concentrated under reduced pressure to afford 2-(2-tert-butoxy-2-oxoethoxy)benzoic acid (1.14 g, 99%) as a tan amorphous solid. $^1$H NMR (300 MHz, DMSO-$d_6$) δ 12.61 (bs, 1H), 7.67 (dd, J=7.6, 1.5 Hz, 1H), 7.56-7.40 (m, 1H), 7.11-6.92 (m, 2H), 4.74 (s, 2H), 1.41 (s, 9H); $^{13}$C NMR (75 MHz, DMSO-$d_6$) δ 167.6, 167.1, 156.5, 132.8, 130.8, 121.6, 120.8, 113.5, 81.5, 65.6, 27.7; HRMS (ESI) calcd for $[C_{13}H_{16}O_5+Na]$275.0890. found 275.0898. Method B with 2-(2-tert-butoxy-2-oxoethoxy)benzoic acid (200 mg, 0.79 mmol) afforded tert-butyl 2-(2-(5-nitrothiazol-2-ylcarbamoyl)phenoxy)acetate (VPC162035) (178 mg, 59%) as a light yellow solid. $^1$H NMR (300 MHz, DMSO-$d_6$) δ 12.71 (s, 1H), 8.71 (s, 1H), 7.83 (dd, J=7.7, 1.5 Hz, 1H), 7.69-7.54 (m, 1H), 7.26-7.10 (m, 2H), 4.89 (s, 2H), 1.44 (s, 9H); $^{13}$C NMR (75 MHz, DMSO-$d_6$) δ 167.6, 165.0, 161.3, 155.7, 142.7, 142.1, 134.4, 130.8, 121.7, 120.4, 113.6, 82.1, 66.0, 27.7; HRMS (ESI) calcd for $[C_{16}H_{17}N_3O_6S+H]^+$380.0911. found 380.0936. Method D with tert-butyl 2-(2-(5-nitrothiazol-2-ylcarbamoyl)phenoxy)acetate (100 mg, 0.26 mmol) afforded 2-(2-(5-nitrothiazol-2-ylcarbamoyl)phenoxy)acetic acid (VPC162042) (78 mg, 92%) as a beige solid. $^1$H NMR (300 MHz, DMSO-$d_6$) δ 12.93 (bs, 2H), 8.67 (s, 1H), 7.87 (dd, J=7.7, 1.7 Hz, 1H), 7.72-7.57 (m, 1H), 7.24 (d, J=8.5 Hz, 1H), 7.18 (t, J=7.6 Hz, 1H), 4.94 (s, 2H); $^{13}$C NMR (75 MHz, DMSO-$d_6$) δ 170.5, 164.8, 161.4, 156.1, 142.8, 142.2, 134.7, 131.1, 121.9, 120.2, 114.2, 66.1; HRMS (ESI) calcd for $[C_{12}H_9N_3O_6S+H]^+$324.0285. found 324.0298. EDC (30 mg, 0.15 mmol), catalytic DMAP, Boc-ethanolamine (14 μL, 0.09 mmol) and 2-(2-(5-nitrothiazol-2-ylcarbamoyl)phenoxy) acetic acid (25 mg, 0.08 mmol) were dissolved in THF (1 mL) and stirred at ambient temperature for 21 hours. Once judged complete by TLC analysis, the resulting suspension was diluted with EtOAc (30 mL) and washed with sat. NaHCO$_3$ (3×20 mL), 0.5M HCl (3×20 mL) and brine (2×20 mL) then dried (MgSO$_4$) followed by filtration and evaporation to dryness. The resulting residue was purified by flash column chromatography (10-70% EtOAc/hexanes) to obtain 2-(tert-butoxycarbonylamino)ethyl 2-(2-(5-nitrothiazol-2-ylcarbamoyl)phenoxy)acetate (33 mg, 92%) as a beige solid. $^1$H NMR (300 MHz, DMSO-$d_6$) δ 12.69 (s, 1H), 8.71 (s, 1H), 7.87 (dd, J=7.7, 1.6 Hz, 1H), 7.69-7.57 (m, 1H), 7.25 (d, J=8.4 Hz, 1H), 7.19 (t, J=7.5 Hz, 1H), 6.97 (t, J=5.6 Hz, 1H), 4.98 (s, 2H), 4.19 (t, J=5.5 Hz, 2H), 3.21 (q, J=5.5 Hz, 2H), 1.35 (s, 9H); $^{13}$C NMR (75 MHz, DMSO-$d_6$) δ 168.4, 164.8, 161.3, 155.8, 142.79, 142.2, 134.6, 131.0, 121.8, 120.1, 113.8, 77.9, 65.9, 64.0, 38.8, 28.2; HRMS (ESI) calcd for $[C_{19}H_{22}N_4O_8S+H]$-467.1231. found 467.1241. Method E with 2-(tert-butoxycarbonylamino)ethyl 2-(2-(5-nitrothiazol-2-ylcarbamoyl)phenoxy)acetate (24 mg, 0.05 mmol) afforded the title compound VPC162082 (19 mg, 93%) as a beige solid. $^1$H NMR (300 MHz, DMSO-$d_6$) δ 12.69 (s, 1H), 8.73 (s, 1H), 8.11 (s, 3H), 7.87 (dd, J=7.7, 1.5 Hz, 1H), 7.65 (t, J=7.0 Hz, 1H), 7.28 (d, J=8.4 Hz, 1H), 7.20 (t, J=7.5 Hz, 1H), 5.04 (s, 2H), 4.41 (t, J=5.1 Hz, 2H), 3.15 (s, 2H); $^{13}$C NMR (75 MHz, DMSO-$d_6$) δ 168.3, 164.8, 161.3, 155.7, 142.8, 142.1, 134.6, 131.0, 121.9, 120.1, 113.8, 65.9, 61.4, 37.9; HRMS (ESI) calcd for $[C_{14}H_{14}N_4O_6S+Na]^+$389.0526. found 389.0535.

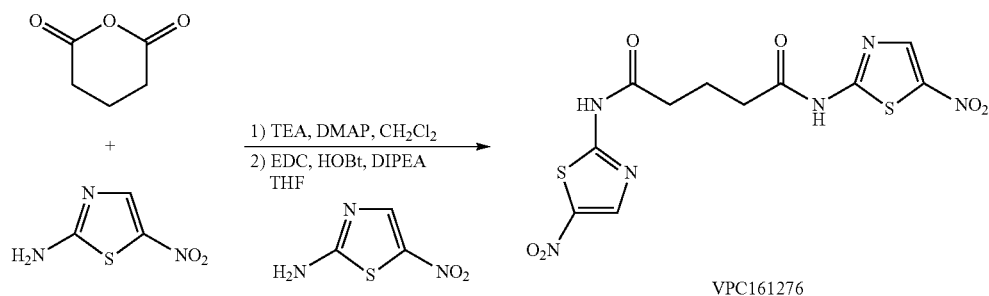 [SMILES: O=C1CCCC(=O)O1 ; Nc1ncc([N+](=O)[O-])s1 ; Nc1ncc([N+](=O)[O-])s1 ; O=C(CCCC(=O)Nc1ncc([N+](=O)[O-])s1)Nc1ncc([N+](=O)[O-])s1]

$N^1,N^5$-Bis(5-nitrothiazol-2-yl)glutaramide (VPC161276)

Glutaric anhydride (1.0 g, 8.8 mmol), TEA (1.35 ml, 9.6 mmol) and cat. DMAP were dissolved in $CH_2Cl_2$ (7 mL). 2-Amino-5-nitrothiazole (1.4 g, 9.64 mmol) was then added and the solution was held at ambient temperature. After 18 hours, the solution was diluted with EtOAc (50 mL) and extracted with 1M NaOH (3×30 mL). The combined aqueous layers were washed with EtOAc (20 mL) then acidified with 12M HCl and subsequently extracted with EtOAc (5×20 mL). The combined organics were washed with brine (2×20 mL), dried ($MgSO_4$), filtered and concentrated to dryness to yield 5-(5-nitrothiazol-2-ylamino)-5-oxopentanoic acid (1.13 g, 54%) as an orange solid. $^1$H NMR (300 MHz, DMSO-$d_6$) δ 12.59 (bs, 1H), 8.59 (s, 1H), 2.57 (t, J=7.4 Hz, 2H), 2.28 (t, J=7.3 Hz, 2H), 1.82 (quint., J=7.3 Hz, 2H); $^{13}$C NMR (75 MHz, DMSO-$d_6$) δ 174.0, 172.8, 161.8, 142.8, 141.7, 34.1, 32.7, 19.6; HRMS (ESI) calcd for $[C_8H_9N_3O_5S+H]^+$ 260.0336. found 260.0344. Method B with 5-(5-nitrothiazol-2-ylamino)-5-oxopentanoic acid (30 mg, 0.12 mmol) afforded the title compound VPC161276 (23 mg, 46%) as an orange solid. $^1$H NMR (300 MHz, DMSO-$d_6$) δ 8.61 (s, 2H), 2.61 (t, J=7.2 Hz, 4H), 1.97 (quint., J=7.0 Hz, 2H); $^{13}$C NMR (75 MHz, DMSO-$d_6$) δ 172.8, 162.0, 142.8, 141.5, 34.0, 19.3; HRMS (ESI) calcd for $[C_{11}H_{10}N_6O_6S_2+H]^+$ 387.0176. found 387.0185.

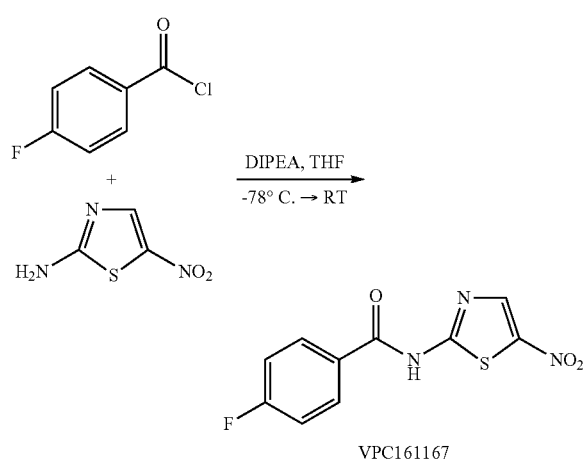

4-Fluoro-N-(5-nitrothiazol-2-yl)benzamide (VPC161167)

Method A with 4-fluorobenzoyl chloride (0.1 mL, 0.84 mmol) afforded the title compound VPC161167 (96 mg, 43%) as a tan solid. $^1$H NMR (300 MHz, DMSO-$d_6$) δ 13.62 (s, 1H), 8.72 (s, 1H), 8.22 (dd, J=8.8, 5.4 Hz, 2H), 7.43 (t, J=8.9 Hz, 2H); $^{13}$C NMR (125 MHz, DMSO-$d_6$) δ 165.3, 165.2 (d, $J_{CF}$=150 Hz), 162.6, 142.6, 142.1, 131.6 (d, $J_{CF}$=9.5 Hz), 127.4, 115.9 (d, $J_{CF}$=22.1 Hz); HRMS (ESI) calcd for $[C_{10}H_6FN_3O_3S+H]^+$ 268.0187. found 268.0196.

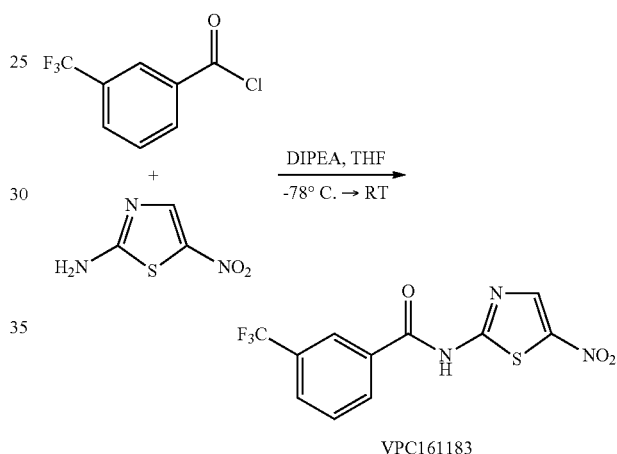

N-(5-Nitrothiazol-2-yl)-3-(trifluoromethyl)benzamide (VPC161183)

Method A with 3-(trifluoromethyl)benzoyl chloride (0.1 mL, 0.68 mmol) afforded the title compound VPC161183 (157 mg, 75%) as a light yellow solid. $^1$H NMR (300 MHz, DMSO-$d_6$) δ 13.85 (bs, 1H), 8.74 (s, 1H), 8.51 (s, 1H), 8.39 (d, J=8.2 Hz, 1H), 8.06 (d, J=7.9 Hz, 1H), 7.83 (t, J=7.9 Hz, 1H); $^{13}$C NMR (125 MHz, DMSO-$d_6$) δ 165.2, 162.4, 142.5, 142.2, 132.7, 131.9, 130.1, 129.8 (q, $J_{CF}$=3.4 Hz), 129.4 (q, $J_{CF}$=32.6 Hz), 125.2 (q, $J_{CF}$=3.9 Hz), 123.8 (q, $J_{CF}$=273 Hz); HRMS (ESI) calcd for $[C_{11}H_6F_3N_3O_3S+H]^+$ 318.0155. found 318.0164.

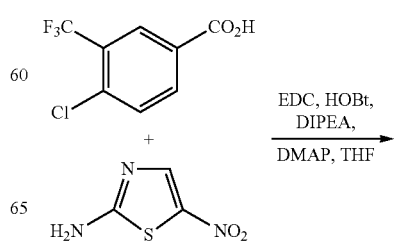

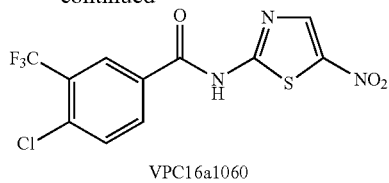

VPC16a1060

4-Chloro-N-(5-nitrothiazol-2-yl)-3-(trifluoromethyl)benzamide) (VPC16a1060)

Method B with 4-chloro-3-(trifluoromethyl)benzoic acid (100 mg, 0.45 mmol) afforded the title compound VPC16a1060 (126 mg, 80%) as an orange solid. $^1$H NMR (300 MHz, DMSO-$d_6$) δ 13.89 (bs, 1H), 8.71 (d, J=0.6 Hz, 1H), 8.58 (d, J=1.9 Hz, 1H), 8.35 (dd, J=8.4, 2.1 Hz, 1H), 7.94 (d, J=8.4 Hz, 1H); $^{13}$C NMR (75 MHz, DMSO-$d_6$) δ 164.4, 162.4, 142.3, 135.7, 134.2, 132.3, 130.4, 127.9 (d, $J_{CF}$=4.8 Hz), 126.9 (q, $J_{CF}$=31.6 Hz), 122.5 (q, $J_{CF}$=274 Hz); HRMS (ESI) calcd for $[C_{11}H_5ClF_3N_3O_3S+H]^+$ 351.9765. found 351.9775.

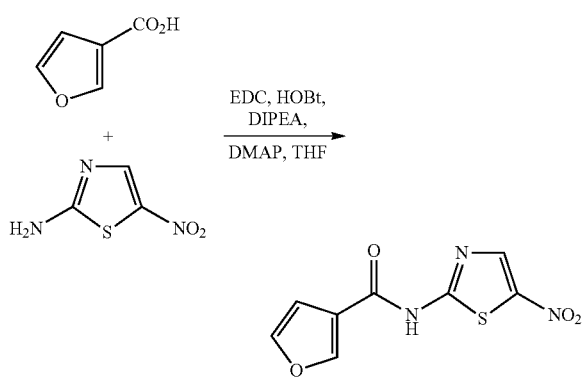

VPC16a1006

N-(5-Nitrothiazol-2-yl)furan-3-carboxamide (VPC16a1006)

Method B with 3-furoic acid (100 mg, 0.89 mmol) afforded the title compound VPC16a1006 (105 mg, 49%) as a yellow solid. $^1$H NMR (300 MHz, DMSO-$d_6$) δ 13.44 (bs, 1H), 8.70 (s, 1H), 8.68 (dd, J=1.5, 0.8 Hz, 1H), 7.93-7.85 (m, 1H), 7.17-7.09 (m, 1H); $^{13}$C NMR (75 MHz, DMSO-$d_6$) δ 162.2, 161.1, 148.4, 145.1, 144.7, 142.6, 120.0, 109.1; HRMS (ESI) calcd for $[C_8H_5N_3O_4S+H]^+$ 240.0074. found 240.0082.

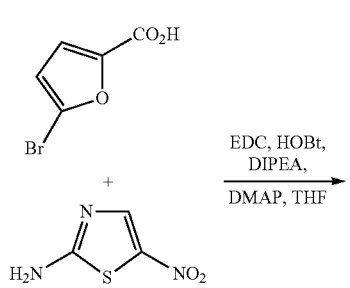

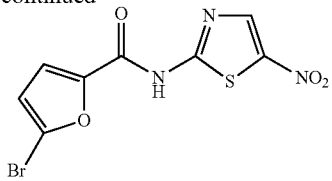

VPC161281

5-Bromo-N-(5-nitrothiazol-2-yl)furan-2-carboxamide (VPC161281)

Method B with 5-bromo-2-furoic acid (100 mg, 0.52 mmol) afforded the title compound VPC161281 (72 mg, 44%) as a red solid. $^1$H NMR (300 MHz, DMSO-$d_6$) δ 13.57 (bs, 1H), 8.63 (s, 1H), 7.73 (d, J=3.7 Hz, 1H), 6.89 (d, J=3.7 Hz, 1H); $^{13}$C NMR (75 MHz, DMSO-$d_6$) δ 161.9, 155.5, 146.6, 142.4, 142.1, 128.9, 120.5, 114.9; HRMS (ESI) calcd for $[C_8H_4BrN_3O_4S+H]^+$ 317.9179. found 317.918.

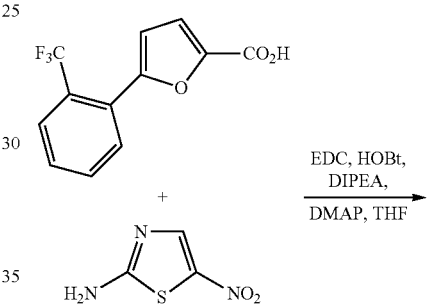

VPC161196

N-(5-Nitrothiazol-2-yl)-5-(2-(trifluoromethyl)phenyl)furan-2-carboxamide (VPC161196)

Method B with 5-(2-(trifluoromethyl)phenyl)-2-furoic acid (100 mg, 0.39 mmol) afforded the title compound VPC161196 (82 mg, 55%) as a bright yellow solid. $^1$H NMR (500 MHz, DMSO-$d_6$) δ 13.78 (bs, 1H), 8.70 (s, 1H), 8.03 (d, J=7.7 Hz, 1H), 7.92 (d, J=7.8 Hz, 1H), 7.87 (d, J=3.8 Hz, 1H), 7.84 (t, J=7.6 Hz, 1H), 7.71 (t, J=7.7 Hz, 1H), 7.05 (d, J=3.7 Hz, 1H); $^{13}$C NMR (125 MHz, DMSO-$d_6$) δ 162.1, 156.3, 154.1, 144.9, 142.6, 142.1, 132.9, 131.1, 130.2, 127.2, 126.9 (q, $J_{CF}$=5.1 Hz), 125.8 (q, $J_{CF}$=31.7 Hz), 123.7 (q, $J_{CF}$=273 Hz), 119.9, 112.7; HRMS (ESI) calcd for $[C_{15}H_8F_3N_3O_4S+H]^+$ 384.0260. found 384.0270.

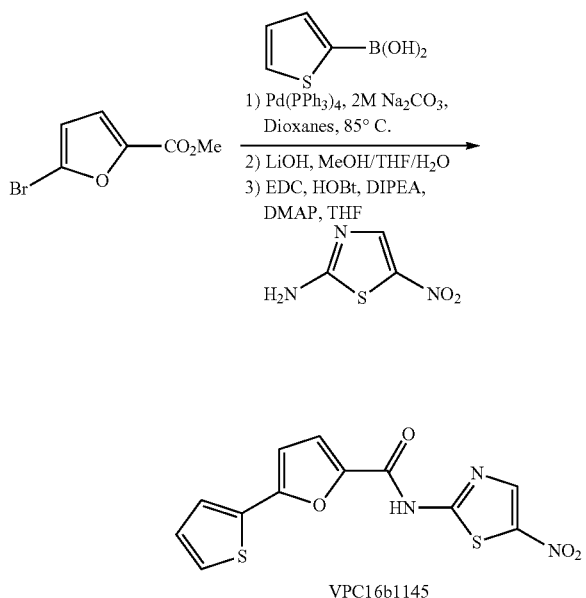

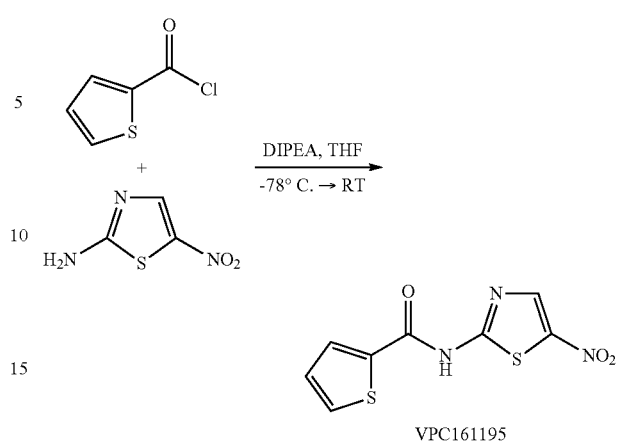

N-(5-Nitrothiazol-2-yl)thiophene-2-carboxamide (VPC161195)

Method A with thiophene-2-carbonyl chloride (0.1 mL, 0.94 mmol) afforded the title compound VPC161195 (85 mg, 36%) as a light yellow solid. $^1$H NMR (300 MHz, DMSO-d$_6$) δ 13.70 (bs, 1H), 8.72 (s, 1H), 8.32 (dd, J=3.8, 1.1 Hz, 1H), 8.09 (dd, J=5.0, 1.1 Hz, 1H), 7.30 (dd, J=5.0, 3.9 Hz, 1H); $^{13}$C NMR (125 MHz, DMSO-d$_6$) δ 162.5, 160.8, 142.6, 142.0, 135.7, 135.3, 132.4, 128.9; HRMS (ESI) calcd for [C$_8$H$_5$N$_3$O$_3$S$_2$+H]255.9845. found 255.9846.

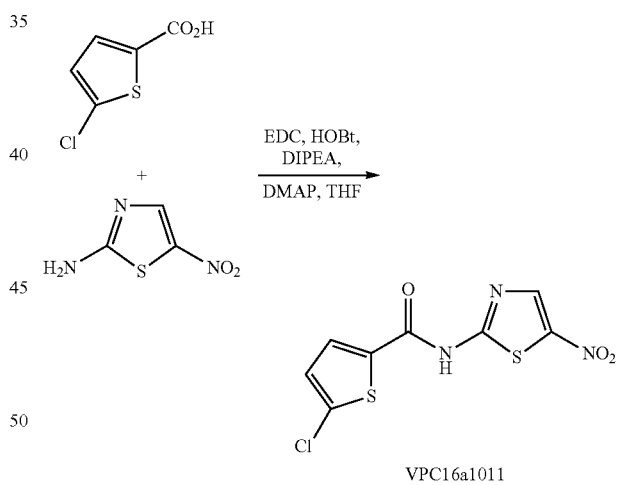

5-Chloro-N-(5-nitrothiazol-2-yl)thiophene-2-carboxamide (VPC16a1011)

Method B with 5-chlorothiophene-2-carboxylic acid (100 mg, 0.62 mmol) afforded the title compound VPC16a1011 (122 mg, 69%) as a yellow solid. $^1$H NMR (500 MHz, DMSO-d$_6$) δ 13.79 (s, 1H), 8.71 (s, 1H), 8.17 (d, J=4.2 Hz, 1H), 7.35 (d, J=4.2 Hz, 1H); $^{13}$C NMR (125 MHz, DMSO-d$_6$) δ 162.4, 160.0, 142.3, 142.0, 137.1, 134.9, 132.4, 129.1; HRMS (ESI) calcd for [C$_8$H$_4$ClN$_3$O$_3$S$_2$+H]$^+$289.9455. found 289.9465.

N-(5-Nitrothiazol-2-yl)-5-(thiophen-2-yl)furan-2-carboxamide (VPC16b1145)

Methyl 5-bromofuran-2-carboxylate (150 mg, 0.73 mmol), Pd(PPh$_3$)$_4$ (42 mg, 0.04 mmol), 2M Na$_2$CO$_3$ (0.73 ml, 1.46 mmol) and thiophen-2-ylboronic acid (121 mg, 0.95 mmol) in 1,4-dioxanes (7 ml) and was warmed to 90° C. The solution was then held at this temperature for 26 hours then cooled and washed with 1M HCl (2×20 mL), brine (2×20 mL) then dried (MgSO$_4$) followed by filtration and evaporation to dryness. The resulting residue was then purified by flash column chromatography (5% EtOAc/hexanes) to obtain methyl 5-(thiophen-2-yl)furan-2-carboxylate (138 mg, 91%) as a yellow oil. $^1$H NMR (500 MHz, DMSO-d$_6$) δ 7.69 (dt, J=5.0, 0.9 Hz, 1H), 7.59 (dt, J=3.6, 0.8 Hz, 1H), 7.40 (dd, J=3.7, 0.6 Hz, 1H), 7.23-7.15 (m, 1H), 6.99 (d, J=3.7 Hz, 1H), 3.83 (s, 3H); $^{13}$C NMR (125 MHz, DMSO-d$_6$) δ 158.1, 152.5, 142.3, 131.2, 128.5, 127.7, 125.8, 120.7, 107.5, 51.8; HRMS (ESI) calcd for [C$_{10}$H$_8$O$_3$S+H]$^+$209.0267. found 209.0272. Method D with methyl 5-(thiophen-2-yl)furan-2-carboxylate (100 mg, 0.48 mmol) afforded 5-(thiophen-2-yl)furan-2-carboxylic acid (92 mg, 99%) as a white solid. $^1$H NMR (300 MHz, DMSO-d$_6$) δ 13.16 (bs, 1H), 7.68 (dd, J=5.0, 1.1 Hz, 1H), 7.56 (dd, J=3.6, 1.1 Hz, 1H), 7.30 (d, J=3.6 Hz, 1H), 7.18 (dd, J=5.0, 3.7 Hz, 1H), 6.95 (d, J=3.6 Hz, 1H); $^{13}$C NMR (125 MHz, DMSO-d$_6$) δ 159.1, 152.0, 143.5, 131.5, 128.5, 127.4, 125.5, 120.0, 107.4; HRMS (ESI) calcd for [C$_9$H$_6$O$_3$S+H]$^+$195.0110. found 195.0112. Method B with 5-(thiophen-2-yl)furan-2-carboxylic acid (75 mg, 0.39 mmol) afforded the title compound VPC16b1145 (46 mg, 37%) as a yellow solid. $^1$H NMR (300 MHz, DMSO-d$_6$) δ 13.69 (bs, 1H), 8.72 (s, 1H), 7.81 (d, J=3.8 Hz, 1H), 7.73 (t, J=4.4 Hz, 2H), 7.22 (dd, J=4.9, 3.7 Hz, 1H), 7.07 (d, J=3.8 Hz, 1H); $^{13}$C NMR (125 MHz, DMSO-d$_6$) δ 162.2, 156.0, 153.2, 143.2, 142.5, 141.9, 131.1, 128.4, 128.1, 126.5, 120.7, 107.8; HRMS (ESI) calcd for [C$_{12}$H$_7$N$_3$O$_4$S$_2$+H]$^+$321.9951. found 321.9963.

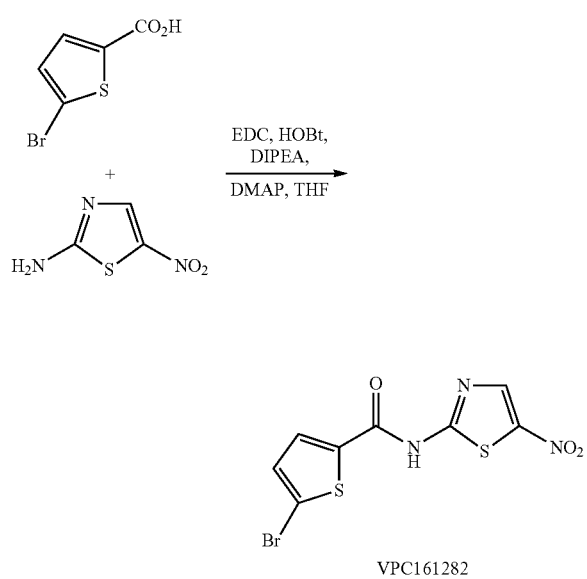

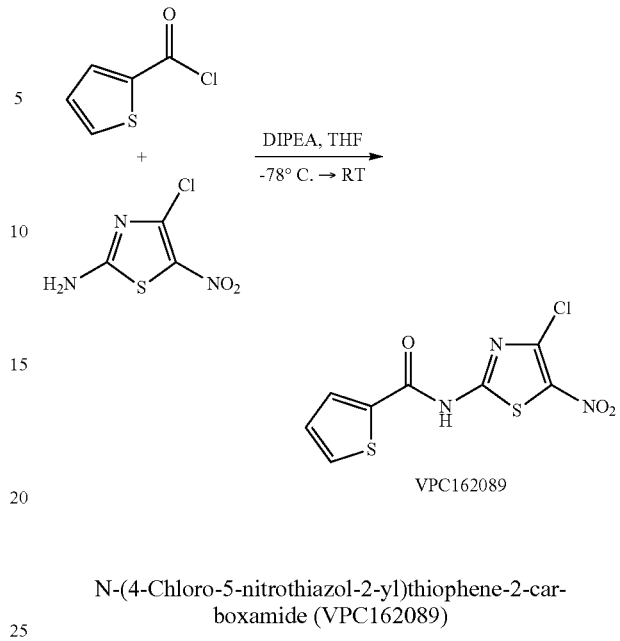

5-Bromo-N-(5-nitrothiazol-2-yl)thiophene-2-carboxamide (VPC161282)

Method B with 5-bromothiophene-2-carboxylic acid (100 mg, 0.48 mmol) afforded the title compound VPC161282 (128 mg, 75%) as a tan solid. $^1$H NMR (300 MHz, DMSO-$d_6$) δ 13.77 (bs, 1H), 8.71 (s, 1H), 8.11 (d, J=4.1 Hz, 1H), 7.44 (d, J=4.1 Hz, 1H); $^{13}$C NMR (75 MHz, DMSO-$d_6$) δ 162.3, 159.9, 142.3, 142.0, 137.5, 133.1, 132.5, 121.4; HRMS (ESI) calcd for $[C_8H_4BrN_3O_3S_2+H]^+$ 333.8950. found 333.8959.

N-(4-Chloro-5-nitrothiazol-2-yl)thiophene-2-carboxamide (VPC162089)

Method A with thiophene-2-carbonyl chloride (0.05 mL, 0.42 mmol) and 2-amino-4-chloro-5-nitrothiazole[2] afforded the title compound VPC162089 (59 mg, 49%) as a yellow solid. $^1$H NMR (300 MHz, DMSO-$d_6$) δ 13.87 (bs, 1H), 8.28 (dd, J=3.8, 0.8 Hz, 1H), 8.09 (dd, J=4.9, 0.8 Hz, 1H), 7.29 (dd, J=4.8, 4.0 Hz, 1H); $^{13}$C NMR (75 MHz, DMSO-$d_6$) δ 161.2, 159.4, 138.2, 135.9, 135.2, 132.7, 129.0; HRMS (ESI) calcd for $[C_8H_4ClN_3O_3S_2+H]^+$ 289.9455. found 289.9467.

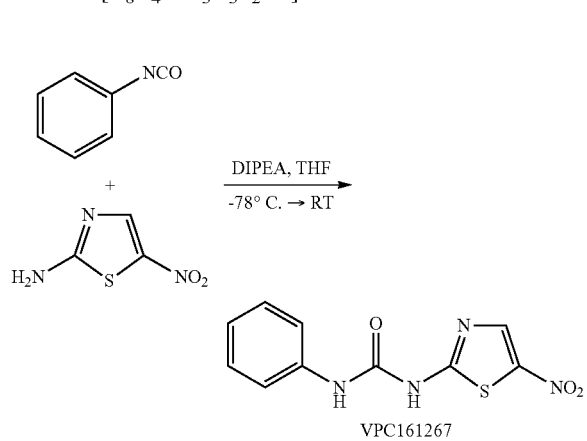

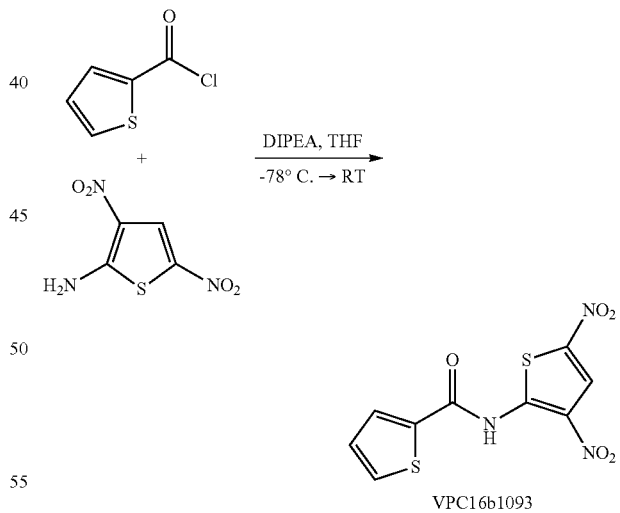

1-(5-Nitrothiazol-2-yl)-3-phenylurea (VPC161223)

Method A with 4-Fluorophenyl isocyanate (in place of acid chloride) (0.1 mL, 0.92 mmol) afforded the title compound VPC161223 (123 mg, 55%) as a tan solid. $^1$H NMR (300 MHz, DMSO-$d_6$) δ 11.58 (bs, 1H), 9.19 (s, 1H), 8.58 (s, 1H), 7.50 (d, J=8.5 Hz, 2H), 7.35 (t, J=7.7 Hz, 2H), 7.17-7.03 (m, 1H); $^{13}$C NMR (75 MHz, DMSO-$d_6$) δ 163.6, 151.4, 142.9, 141.2, 137.8, 129.1, 123.7, 119.2; HRMS (ESI) calcd for $[C_{10}H_8N_4O_3S+H]^+$ 265.0390. found 265.0398.

N-(3,5-Dinitrothiophen-2-yl)thiophene-2-carboxamide (VPC16b1093)

Method A with thiophene-2-carbonyl chloride (0.1 mL, 0.94 mmol) afforded the title compound VPC16b1093 (188 mg, 67%) as a brown solid. $^1$H NMR (500 MHz, DMSO-$d_6$) δ 8.52 (s, 1H), 8.15 (d, J=4.6 Hz, 1H), 8.05 (d, J=3.8 Hz, 1H), 7.34 (t, J=4.6 Hz, 1H); $^{13}$C NMR (125 MHz, DMSO-$d_6$) δ

160.2, 146.9, 138.9, 136.2, 134.4, 133.1, 130.2, 129.1, 123.2; HRMS (ESI) calcd for $[C_9H_5N_3O_5S_2+H]^+$ 299.9743. found 299.9755.

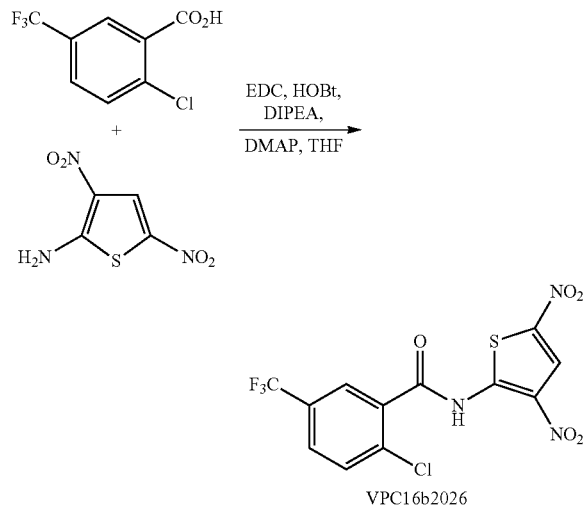

2-Chloro-N-(3,5-dinitrothiophen-2-yl)-5-(trifluoromethyl)benzamide (VPC16b2026)

Method B with 2-chloro-5-(trifluoromethyl)benzoic acid (100 mg, 0.45 mmol) afforded the title compound VPC16b2026 (99 mg, 56%) as an orange solid. $^1$H NMR (500 MHz, DMSO-$d_6$) δ 12.66 (bs, 1H), 8.54 (s, 1H), 8.20 (d, J=0.8 Hz, 1H), 8.00 (ddd, J=8.5, 1.5, 0.8 Hz, 1H), 7.89 (d, J=8.5 Hz, 1H); $^{13}$C NMR (125 MHz, DMSO-$d_6$) δ 165.4, 145.8, 139.3, 135.2, 133.7, 131.2, 130.7, 129.4, 127.9 (q, $J_{CF}$=33.0 Hz), 127.4, 123.4 (q, $J_{CF}$=271 Hz), 123.1; HRMS (ESI) calcd for $[C_{12}H_5ClF_3N_3O_5S+H]^+$ 395.9663. found 395.9658.

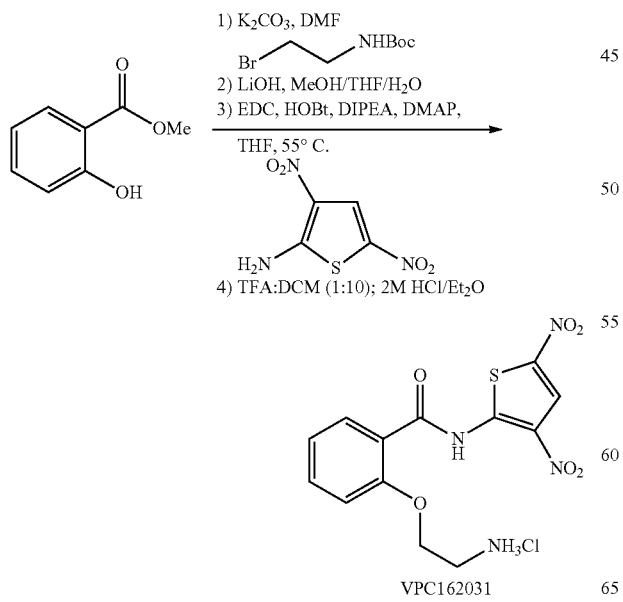

2-(2-Aminoethoxy)-N-(3,5-dinitrothiophen-2-yl) benzamide (VPC16b2031)

Method C with methyl 2-hydroxybenzoate (2.0 mL, 15.4 mmol) afforded methyl 2-(2-(tert-butoxycarbonylamino) ethoxy)benzoate (4.55 g, 99%) as an amber oil. $^1$H NMR (300 MHz, DMSO-$d_6$) δ 7.64 (dd, J=7.6, 1.1 Hz, 1H), 7.57-7.45 (m, 1H), 7.14 (d, J=8.4 Hz, 1H), 7.02 (t, J=7.5 Hz, 1H), 6.83 (t, J=5.3 Hz, 1H), 4.03 (t, J=5.9 Hz, 2H), 3.79 (s, 3H), 3.31 (q, J=5.8 Hz, 2H), 1.38 (s, 9H); $^{13}$C NMR (75 MHz, DMSO-$d_6$) δ 157.4, 155.6, 133.4, 130.7, 120.6, 120.5, 114.0, 77.8, 67.4, 51.8, 39.3, 31.4, 28.2, 27.6; HRMS (ESI) calcd for $[C_{15}H_{21}NO_5+Na]^+$ 318.1312. found 318.1319. Method D with ethyl 2-(2-(tert-butoxycarbonylamino)ethoxy)benzoate (240 mg, 0.81 mmol) afforded 2-(2-(tert-butoxycarbonylamino)ethoxy)benzoic acid (221 mg, 97%) as a white solid. $^1$H NMR (300 MHz, DMSO-$d_6$) δ 12.56 (s, 1H), 7.65 (dd, J=7.6, 1.7 Hz, 1H), 7.48 (td, J=8.3, 1.7 Hz, 1H), 7.13 (d, J=8.4 Hz, 1H), 7.01 (t, J=7.5 Hz, 1H), 6.85 (t, J=5.3 Hz, 1H), 1.37 (s, 9H); $^{13}$C NMR (75 MHz, DMSO-$d_6$) δ 167.3, 157.3, 155.7, 133.1, 130.8, 121.7, 120.6, 114.1, 77.9, 67.6, 39.2, 28.2; HRMS (ESI) calcd for $[C_{14}H_{19}NO_5+Na]^+$ 304.115. found 304.1168. Method B 2-(2-(tert-butoxycarbonylamino) ethoxy)benzoic acid (250 mg, 1.15 mmol) afforded tert-butyl 2-(2-(3,5-dinitrothiophen-2-ylcarbamoyl)phenoxy)ethylcarbamate (325 mg, 68%) as an orange solid. $^1$H NMR (500 MHz, DMSO-$d_6$) δ 13.04 (s, 1H), 8.58 (s, 1H), 8.11 (d, J=6.6 Hz, 1H), 7.71 (dd, J=11.4, 4.3 Hz, 1H), 7.40 (d, J=8.4 Hz, 1H), 7.21 (t, J=7.5 Hz, 1H), 7.06 (t, J=5.7 Hz, 1H), 4.43 (t, J=4.8 Hz, 2H), 3.44 (q, J=4.7 Hz, 2H), 1.24 (s, 9H); $^{13}$C NMR (125 MHz, DMSO-$d_6$) δ 163.5, 157.3, 155.7, 146.6, 139.0, 136.3, 132.3, 130.1, 123.0, 121.8, 117.3, 113.9, 77.8, 69.1, 38.6, 28.0; HRMS (ESI) calcd for $[C_{18}H_{20}N_4O_8S+Na]^+$ 475.0894. found 475.0892. Method E with tert-butyl 2-(2-(3,5-dinitrothiophen-2-ylcarbamoyl)phenoxy)ethylcarbamate (51 mg, 0.11 mmol) afforded the title compound VPC16b2031 (40 mg, 91%) as a yellow solid. $^1$H NMR (500 MHz, DMSO-$d_6$) δ 12.77 (s, 1H), 8.55 (s, 1H), 8.46 (bs, 3H), 8.12 (dd, J=7.8, 1.5 Hz, 1H), 7.88-7.65 (m, 1H), 7.43 (d, J=8.5 Hz, 1H), 7.25 (t, J=7.5 Hz, 1H), 4.65 (t, J=4.8 Hz, 2H), 3.42 (bs, 2H); $^{13}$C NMR (125 MHz, DMSO-$d_6$) δ 163.5, 156.6, 146.9, 139.1, 136.4, 132.5, 129.9, 122.9, 122.2, 117.3, 113.7, 66.5, 37.6.

Additional Synthetic Schemes

Figure 6:
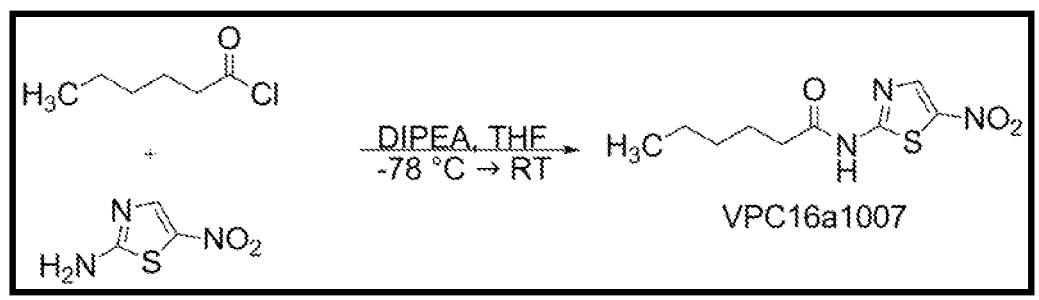
Figure 7A:
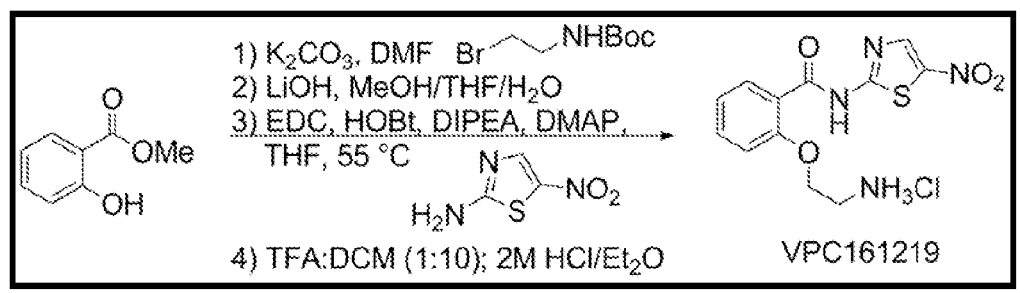
FIG. 7 (A, B, and C). Scheme for Aliphatic Amine Analogues of 2-amino-5-nitrothiazole FIG. 8. Scheme for Amino Acid Analogues of 2-amino-5-nitrothiazole FIG. 9. Scheme for Anthranilic Analogues of 2-amino-5-nitrothiazole FIG. 10. Scheme for Pyridine Analogues of 2-amino-5-nitrothiazole FIG. 11. Scheme for Indole Analogues of 2-amino-5-nitrothiazole FIG. 12. Scheme for Carboxylic Acid Analogues of 2-amino-5-nitrothiazole FIG. 13. Scheme for Dimer-like Analogues of 2-amino-5-nitrothiazole FIG. 14. Scheme for Halide Analogues of 2-amino-5-nitrothiazole FIG. 15. Scheme for Monosubstituted Analogues of 2-amino-5-nitrothiazole FIG. 16. Scheme for Disubstituted Analogues of 2-amino-5-nitrothiazole FIG. 17 (A, B, C, and D). Scheme for Furan Analogues of 2-amino-5-nitrothiazole FIG. 18 (A, B, and C). Scheme for Thiophene Analogues of 2-amino-5-nitrothiazole FIG. 19. Scheme for Amide Isosteres of 2-amino-5-nitrothiazole FIG. 20. Scheme for Analogues of 2-amino-4-chloro-5-nitrothiazole FIG. 21 (A, B, and C). Scheme for Analogues of 2-amino-3,5-dinitrothiophene Additional specific schemes are provided in the Examples.
Figure 7B:
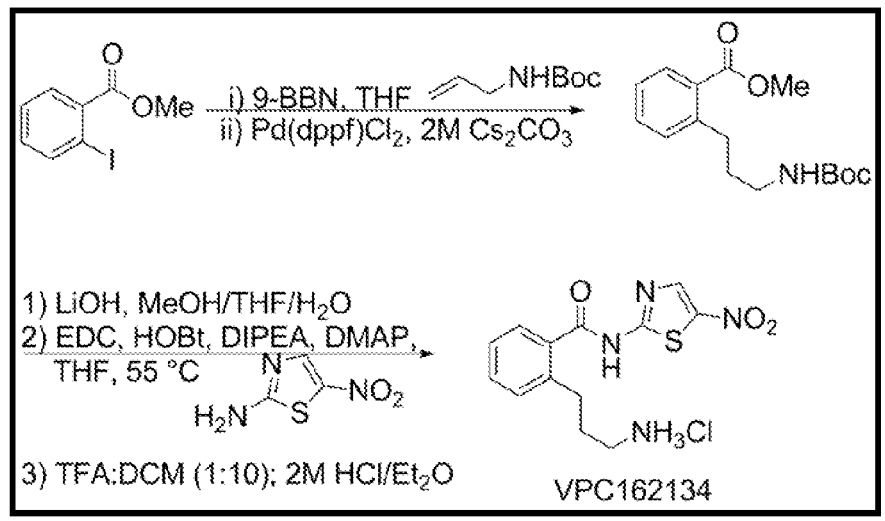
Figure 7C:
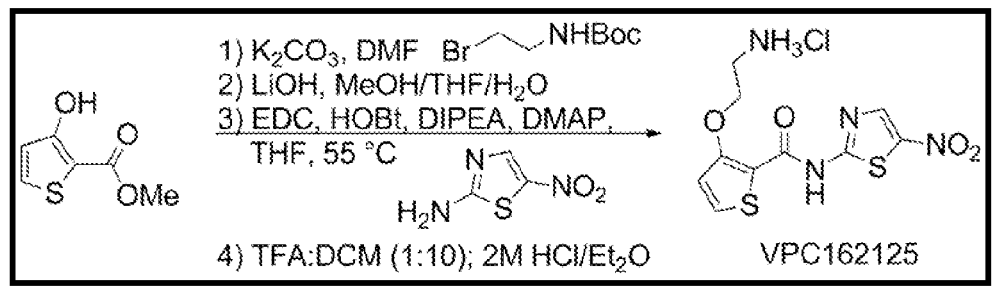
Figure 8:
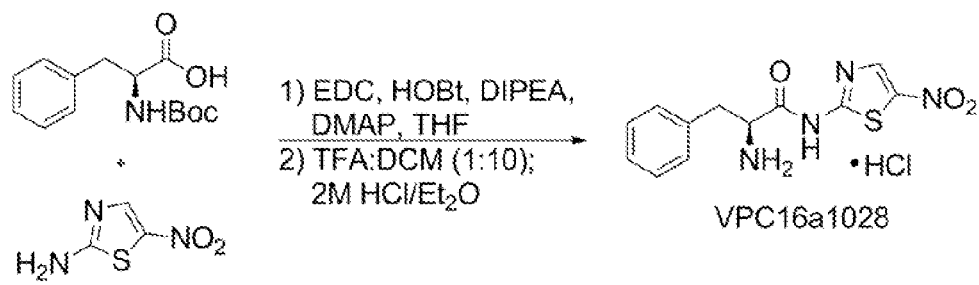
Figure 9:
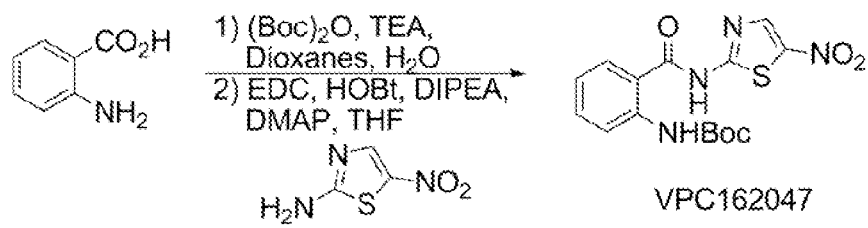
Figure 10:
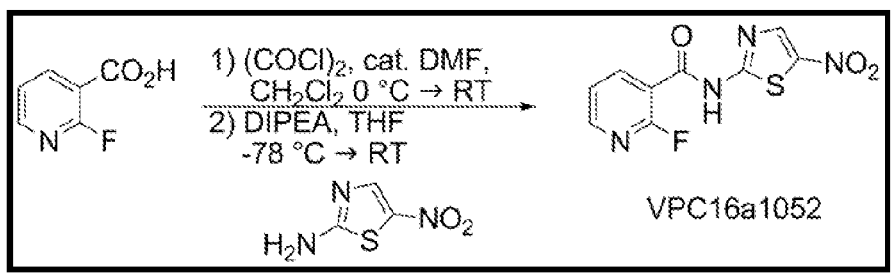
Figure 11:
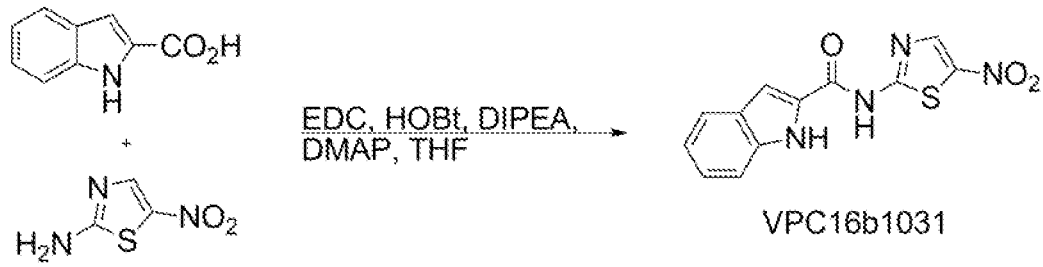
Figure 12:
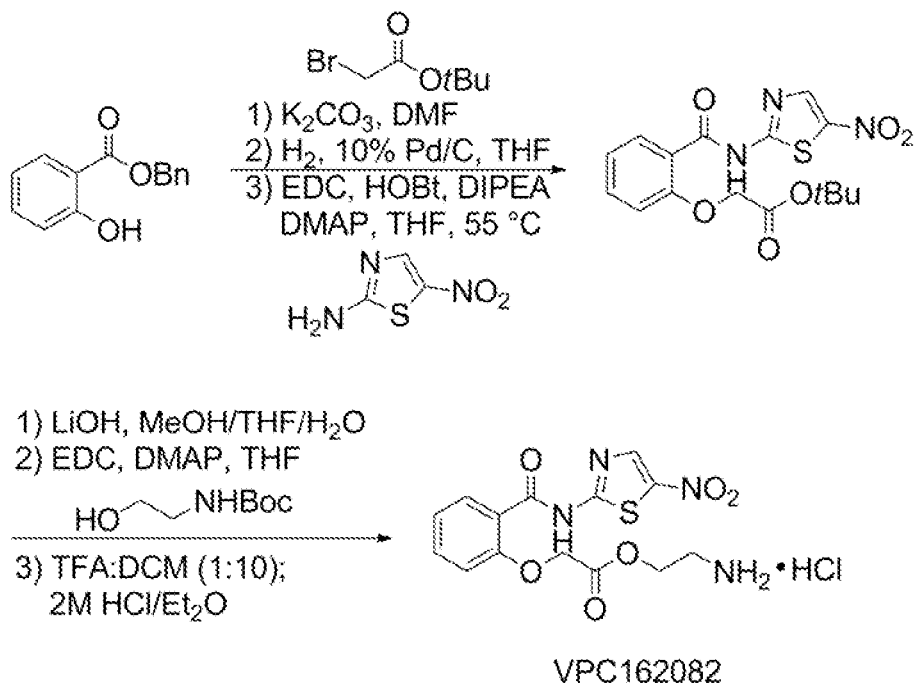
Figure 13:
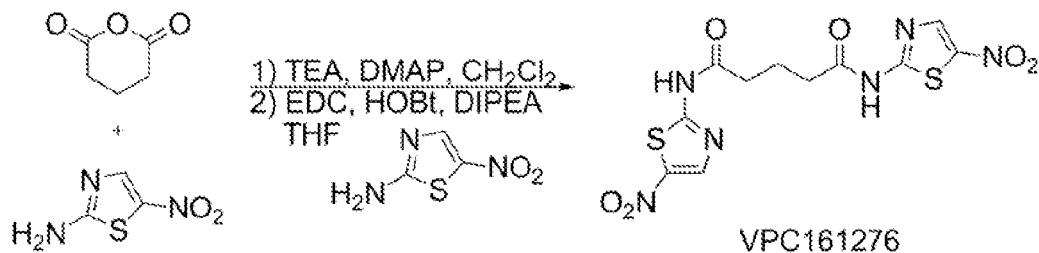
Figure 14:
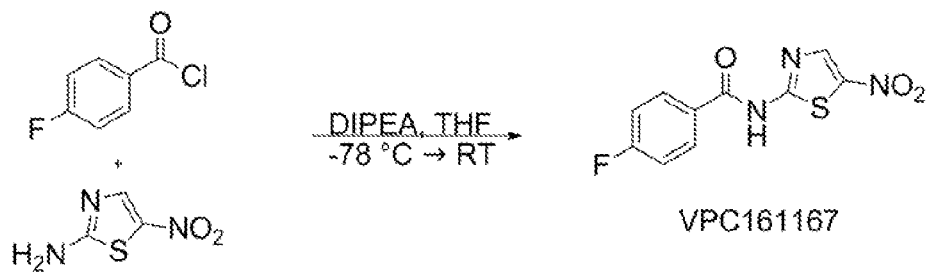
Figure 15:
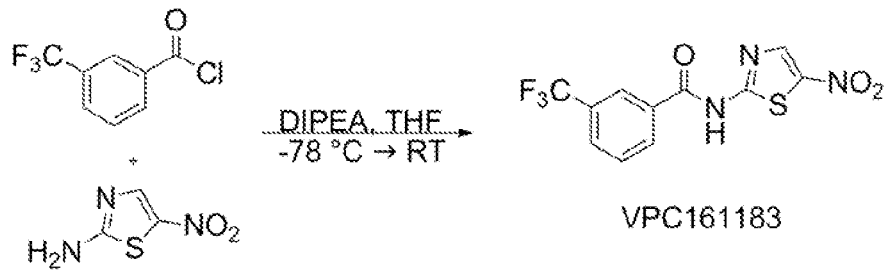
Figure 16:
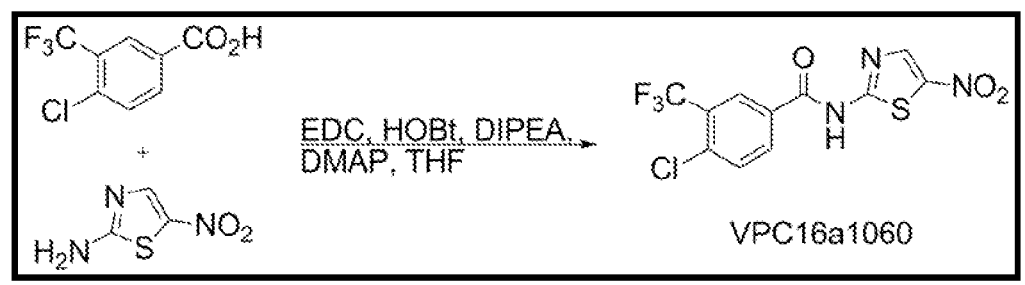
Figure 17A:
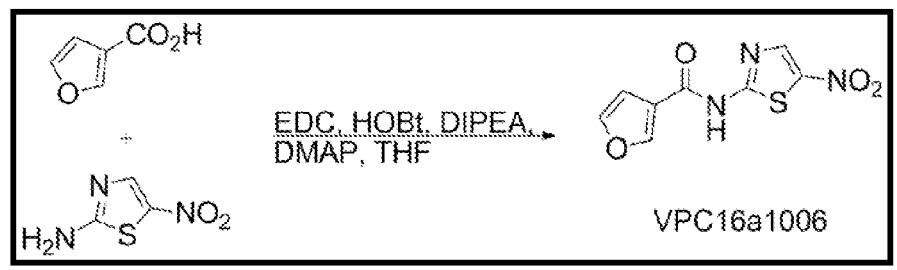
Figure 17B:
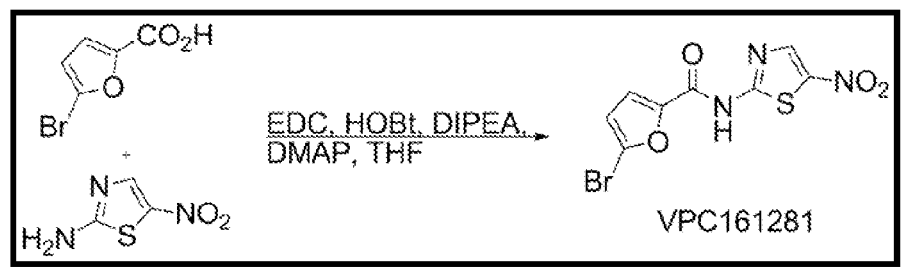
Figure 17C:
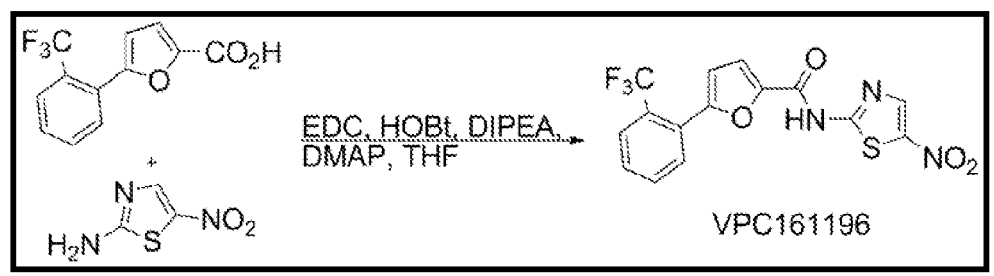
Figure 17D:
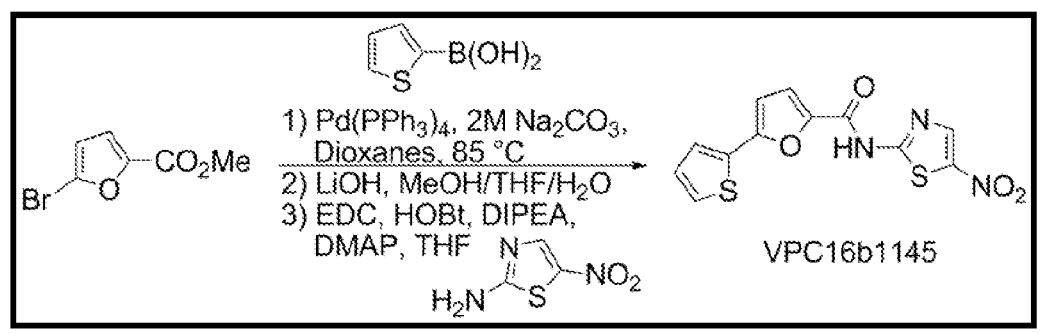
Figure 18A:
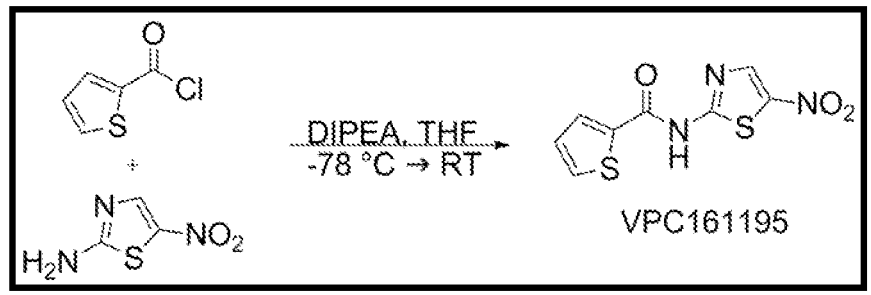
Figure 18B:
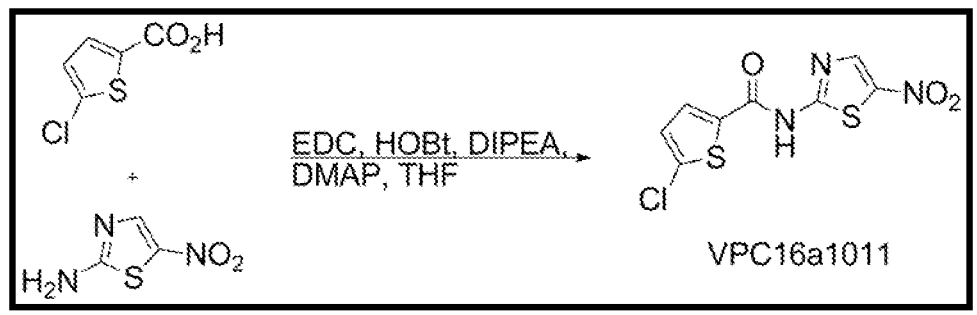
Figure 18C:
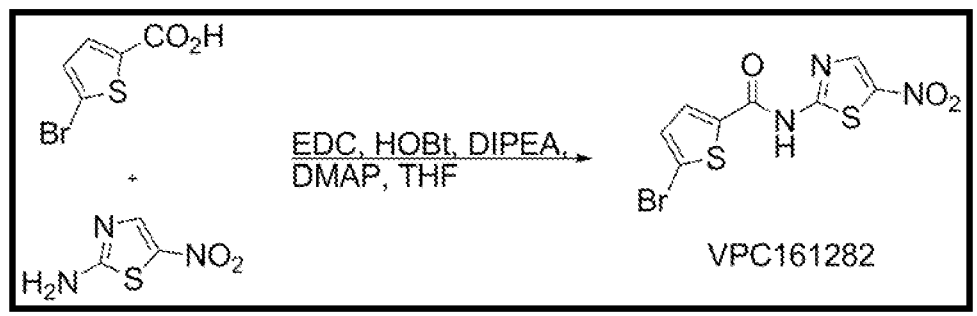
Figure 19:
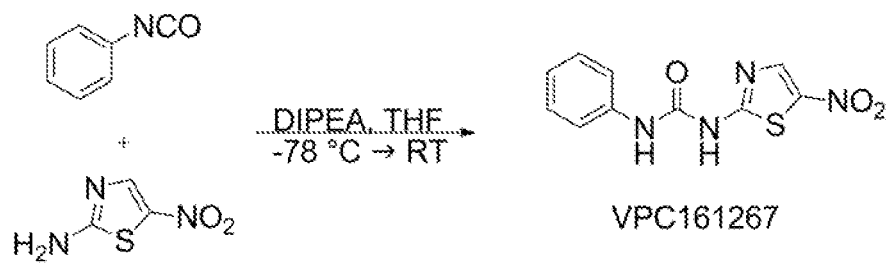
Figure 20:
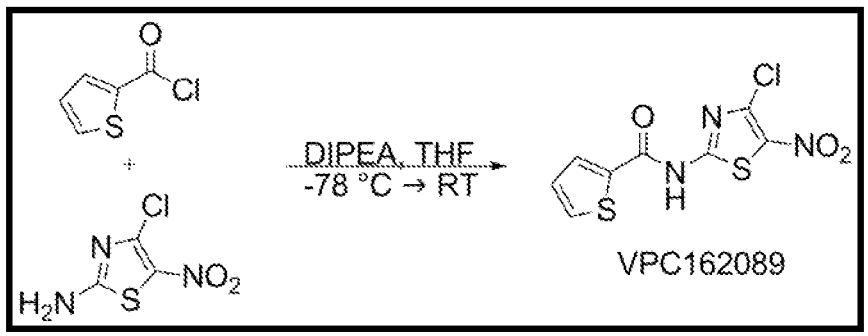
Figure 21A:
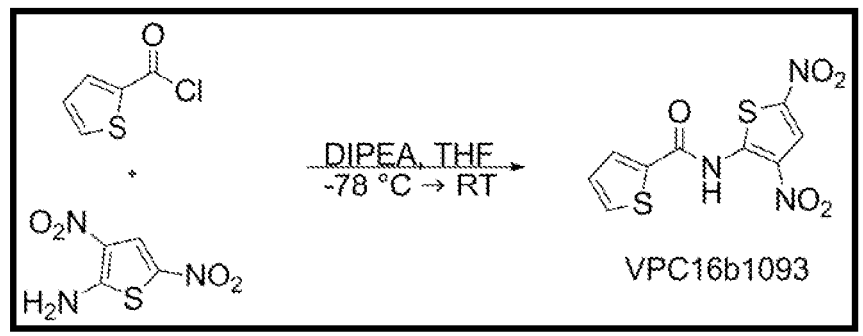
Figure 21B:
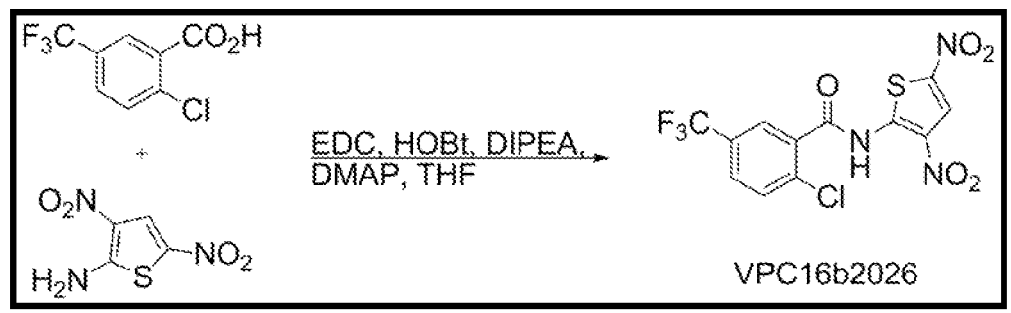
Figure 21C:
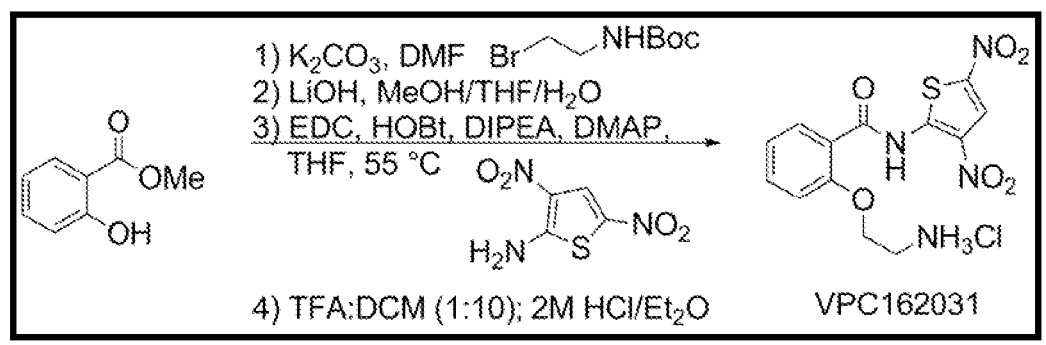

FIGS. 15-30 of Hoffman et al. (PCT/US2010/027397) provide synthetic Schemes for other useful compounds of the invention. Schemes generating "lead" compounds for a particular use in those Figures are marked with bold boxes in those figures. FIGS. 15-30 of Hoffman et al. are reproduced herein as FIGS. 6-21.

Other Compounds

The structure of the compound Amixin (VPC161219), also referred to as AMIX herein, is:

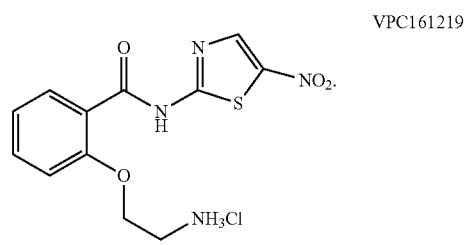

Provided below are Tables demonstrating side chains, R groups, etc., of various derivatives and analogs used herein and activities of these compounds against a variety of bacteria other than mycobacteria. The following types of compounds were made and tested in Hoffman et al., (PCT/US2010/027397):

Table 3—Aliphatic Derivatives of 2-amino-5-nitrothiazole
Table 4—Aliphatic Amine Analogues of 2-amino-5-nitrothiazole
Table 5—Amino Acid Analogues of 2-amino-5-nitrothiazole
Table 6—Anthranilic Analogues of 2-amino-5-nitrothiazole
Table 7—Pyridine Analogues of 2-amino-5-nitrothiazole
Table 8—Indole Analogues of 2-amino-5-nitrothiazole
Table 9—Carboxylic Acid Analogues of 2-amino-5-nitrothiazole
Table 10—Dimer-like Analogues of 2-amino-5-nitrothiazole
Table 11—Halide Analogues of 2-amino-5-nitrothiazole
Table 12—Monosubstituted Analogues of 2-amino-5-nitrothiazole
Table 13—Disubstituted Analogues of 2-amino-5-nitrothiazole
Table 14—Furan Analogues of 2-amino-5-nitrothiazole
Table 15—Thiophene Analogues of 2-amino-5-nitrothiazole
Table 16—Amide Isosteres of 2-amino-5-nitrothiazole
Table 17—Analogues of 2-amino-4-chloro-5-nitrothiazole
Table 18—Analogues of 2-amino-3,5-dinitrothiophene Tables 3-18 of Hoffman et al. are reproduced herein and numbered Supplemental 1-16 (see below). The effects of some of these compounds on mycobacteria are disclosed above in Example 1.

SUPPLEMENTAL TABLE 1

Aliphatic Derivatives of 2-amino-5-nitrothiazole

| R = | MIC (μM) | | | | | | | | Disk Diffusion (%) | Direct PFOR Enzyme Assay (%) |
| --- | --- | --- | --- | --- | --- | --- | --- | --- | --- | --- |
| | C. difficile | H. pylori | C. jejuni | MRSA | S. epidermidis | | E. coli | | C. difficile | |
| | | | | | Plank | Biofilm | Plank | Biofilm | | |
| 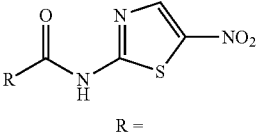 Nitazoxanide | 52.1 | 13.0 | 39.1 | 39.1 | 52.1 | 32.5 | 104.1 | 26.0 | 100 | 100 |
| 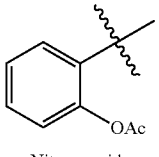 VPC161178 | — | 1.3 | 3.0 | 12.0 | 32.1 | 32.1 | 128.4 | 128.4 | 78 ± 3 | 73 |
| 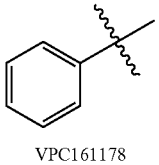 VPC16a1010 | 62.6 | 0.7 | 11.4 | 125.2 | 31.3 | — | 125.2 | 31.3 | 53 ± 3 | 93 |
| 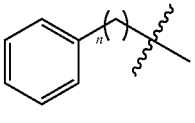 n = 1 VPC16a1013 | — | 21.6 | 1.8 | 121.5 | 22.8 | — | 121.5 | — | — | — |
| 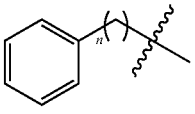 n = 2 VPC16b1030 | — | 0.3 | 1.30 | 115.4 | 14.4 | — | 115.4 | 50.5 | 54.5 ± 0.5 | — |

SUPPLEMENTAL TABLE 1-continued

| Structure | | | | | | | | | |
|---|---|---|---|---|---|---|---|---|---|
| VPC16a1020 (n = 3, phenyl-(CH2)n-) | — | 13.8 | 2.6 | 109.8 | 109.8 | — | 109.8 | 54.9 | 33 ± 3 | — |
| VPC16b1032 (phenyl-cyclopropyl) | — | 1.7 | 26.6 | 13.8 | 13.8 | — | 110.6 | — | — | — |
| VPC16a1018 (3-methylbenzofuran-2-yl-CH2-) | — | 0.7 | 10.7 | 106.2 | 106.2 | 26.5 | 106.2 | 53.1 | — | — |
| VPC16a1033 (isopropyl) | — | 3.5 | 14.0 | 171.0 | 21.4 | 21.4 | 42.7 | 42.7 | — | — |
| VPC16b1045 (n = 2) | — | 0.5 | 2.1 | 148.7 | 37.2 | 4.6 | 148.7 | 148.7 | — | — |
| VPC16a1007 (n = 4) | 65.8 | 1.4 | 5.5 | 131.5 | 32.9 | — | 131.5 | 131.5 | 56.5 ± 0.5 | 123 |
| VPC16b1046 (n = 6) | — | 0.8 | 106.9 | 59.0 | 11.1 | 7.4 | 117.9 | 88.4 | 54 ± 4 | — |
| VPC16b1043 (n = 8) | — | 1.2 | 3.9 | 106.9 | 106.9 | 1.7 | 106.9 | 106.9 | — | — |
| VPC161200 (cinnamyl) | — | 0.3 | 2.7 | 116.2 | 29.1 | 14.5 | 116.2 | 116.2 | — | 93 |
| VPC161239 (4-CF3-cinnamyl) | — | 0.6 | 93.2 | 93.2 | 2.9 | — | 93.2 | — | — | — |

SUPPLEMENTAL TABLE 2
Aliphatic Amine Analogues of 2-amino-5-nitrothiazole
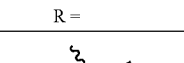
| R = | MIC (μM) | | | | | | | | Disk Diff (%) | Direct PFOR Enzyme Assay |
|---|---|---|---|---|---|---|---|---|---|---|
| | C. difficile | H. pylori | C. jejuni | MRSA | S. epidermidis | | E. coli | | C. difficile | (%) |
| | | | | | Plank | Biofilm | Plank | Biofilm | | |
| 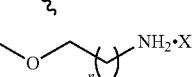 Nitazoxanide | 52.1 | 13.0 | 39.1 | 39.1 | 52.1 | 32.5 | 104.1 | 26.0 | 100 | 100 |
| 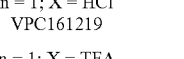 n = 1; X = HCl VPC161219 | 46.4 | 0.7 | 17.4 | 92.8 | 92.8 | 46.4 | 69.6 | 46.4 | 88 ± 4 | 114 |
| n = 1; X = TFA VPC161219TFA | — | 1.88 | 14.2 | 75.8 | 75.8 | — | 75.8 | — | 81 | — |
| n = 2; X = HCl VPC162102HCl | — | 1.0 | 8.4 | 89.2 | 44.6 | — | 89.2 | — | 74 | — |
| n = 2; X = TFA VPC162102TFA | — | 0.9 | 13.8 | 73.3 | 73.3 | — | 73.3 | — | 79 | — |
| n = 3; X = HCl VPC162096HCl | — | 2.0 | 5.4 | 85.8 | 42.9 | — | 85.8 | — | 111 | — |
| n = 3; X = TFA VPC162096TFA | — | 1.7 | 6.7 | 71.0 | 35.5 | — | 71.0 | — | 111 | — |
| 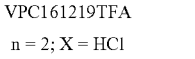 X = HCl VPC162134 | — | 2.9 | 17.5 | 93.3 | 93.3 | — | — | — | — | 144 |
| 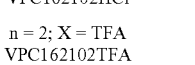 X = HCl VPC162125 | — | 0.7 | 11.4 | 91.2 | 91.2 | — | 91.2 | — | — | 137 |
| 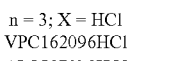 VPC16a1021 | — | 4.4 | 34.8 | 92.8 | 92.8 | — | 92.8 | — | — | — |
| 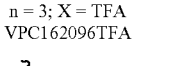 VPC16b1037 | — | 2.2 | 2.9 | 92.8 | 92.8 | 92.8 | 92.8 | 23.2 | 77 ± 4 | 78 |

SUPPLEMENTAL TABLE 2-continued
| Structure | | | | | | | | | |
|---|---|---|---|---|---|---|---|---|---|
| 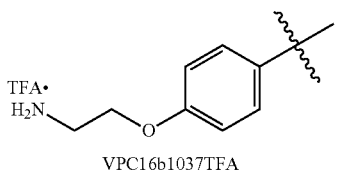 VPC16b1037TFA | — | 2.4 | 3.6 | 75.8 | 37.9 | — | 75.8 | — | 84 | — |
| 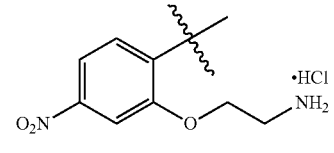 VPC161256 | — | 1.3 | 5.1 | 82.1 | 82.1 | — | 82.1 | — | — | — |
| 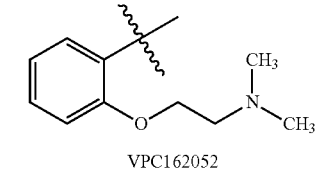 VPC162052 | — | 1.5 | 17.8 | 95.1 | 95.1 | — | 95.1 | — | — | — |
| 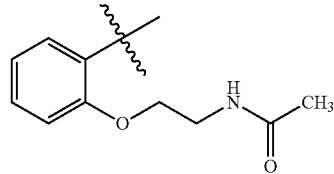 VPC162044 | — | 1.1 | 34.3 | 91.3 | 22.8 | — | 91.3 | — | 77 | — |
| 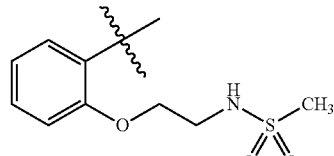 VPC162045 | — | 0.6 | 51.8 | 82.8 | 62.1 | — | 82.8 | — | 51 | — |
| 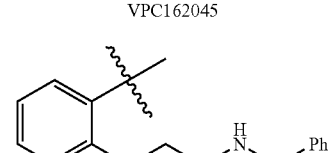 VPC162049 | — | 0.6 | 77.6 | 77.6 | 77.6 | — | 77.6 | — | 26 | — |
| 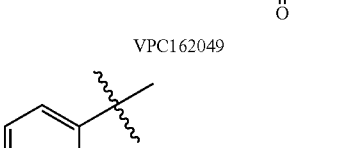 VPC162048 | — | 0.4 | 74.9 | 74.9 | 74.9 | — | 74.9 | — | 31 | — |
| 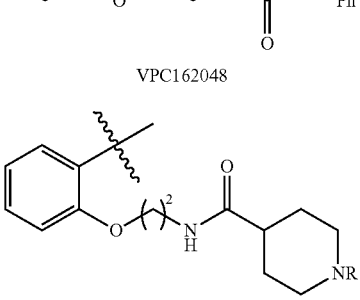 R = Boc VPC162059 | — | 0.7 | 61.6 | 61.6 | 61.6 | — | 61.6 | — | 38 | — |

SUPPLEMENTAL TABLE 2-continued
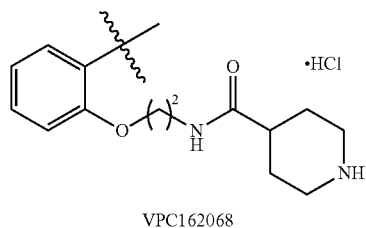
VPC162068
| — | 52.6 | 35.1 | 70.2 | 70.2 | — | 70.2 | — | — | — |
SUPPLEMENTAL TABLE 3
Amino Acid Analogues of 2-amino-5-nitrothiazole
| R = | MIC (μM) | | | | | | | | Disk Diffusion (%) C. difficile | Direct PFOR Enzyme Assay (%) |
|---|---|---|---|---|---|---|---|---|---|---|
| | C. difficile | H. pylori | C. jejuni | MRSA | S. epidermidis Plank | S. epidermidis Biofilm | E. coli Plank | E. coli Biofilm | | |
| 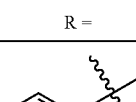 Nitazoxanide | 52.1 | 13.0 | 39.1 | 39.1 | 52.1 | 32.5 | 104.1 | 26.0 | 100 | 100 |
| 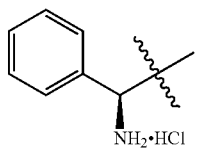 VPC16a1027 | — | 76.3 | 38.1 | 101.7 | 101.7 | 101.7 | 101.7 | 25.4 | — | — |
| 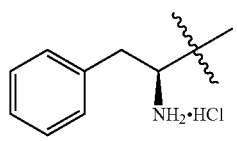 VPC16a1028 | — | 18.3 | 36.5 | 97.3 | 97.3 | 97.3 | 97.3 | 48.7 | — | — |
| 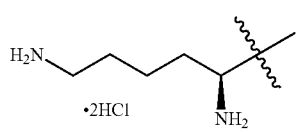 VPC16a1032 | — | 69.3 | 92.4 | 92.4 | 92.4 | 92.4 | 92.4 | 0.1 | — | — |

SUPPLEMENTAL TABLE 4

Anthranilic Analogues of 2-amino-5-nitrothiazole

| R = | MIC (μM) | | | | | | | | Disk Diffusion (%) | Direct PFOR Enzyme Assay (%) |
|---|---|---|---|---|---|---|---|---|---|---|
| | C. difficile | H. pylori | C. jejuni | MRSA | S. epidermidis | | E. coli | | C. difficile | |
| | | | | | Plank | Biofilm | Plank | Biofilm | | |
| 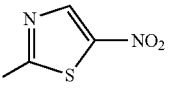 Nitazoxanide | 52.1 | 13.0 | 39.1 | 39.1 | 52.1 | 32.5 | 104.1 | 26.0 | 100 | 100 |
| 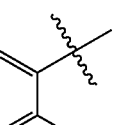 VPC162055 | — | 2.4 | 11.4 | 121.1 | 90.8 | — | 45.4 | — | 83 | — |
| 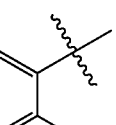 VPC162046b | — | 6.9 | 41.6 | 55.5 | 111.0 | — | 111.0 | — | — | — |
| 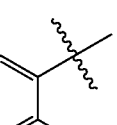 VPC162047 | — | 0.3 | 27.4 | 5.5 | 5.5 | — | 87.8 | — | 83 | — |

SUPPLEMENTAL TABLE 5

Pyridine Analogues of 2-amino-5-nitrothiazole

| R = | MIC (μM) | | | | | | | | Disk Diffusion (%) | Direct PFOR Enzyme Assay (%) |
|---|---|---|---|---|---|---|---|---|---|---|
| | C. difficile | H. pylori | C. jejuni | MRSA | S. epidermidis | | E. coli | | C. difficile | |
| | | | | | Plank | Biofilm | Plank | Biofilm | | |
| Nitazoxanide | 52.1 | 13.0 | 39.1 | 39.1 | 52.1 | 32.5 | 104.1 | 26.0 | 100 | 100 |
| 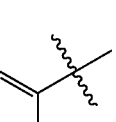 VPC161177 | — | 16.0 | 24.0 | 127.9 | 127.9 | 127.9 | 127.9 | 127.9 | — | — |

SUPPLEMENTAL TABLE 5-continued

| R = | C. difficile | H. pylori | C. jejuni | MRSA | S. epidermidis Plank | S. epidermidis Biofilm | E. coli Plank | E. coli Biofilm | Disk Diffusion (%) C. difficile | Direct PFOR Enzyme Assay (%) |
|---|---|---|---|---|---|---|---|---|---|---|
| 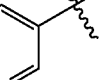 VPC161176 | — | 4.0 | 71.9 | 127.9 | 127.9 | 63.9 | 127.9 | 127.9 | — | — |
|  VPC16a1053 | — | 3.7 | 14.9 | 119.3 | 119.3 | — | 119.3 | — | — | — |
| 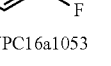 VPC16a1052 | — | 3.7 | 7.5 | 119.3 | 119.3 | — | 119.3 | — | 100 | 91 |

SUPPLEMENTAL TABLE 6

Indole Analogues of 2-amino-5-nitrothiazole

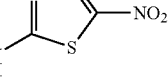

| R = | MIC (μM) | | | | | | | | Disk Diffusion (%) C. difficile | Direct PFOR Enzyme Assay (%) |
| | C. difficile | H. pylori | C. jejuni | MRSA | S. epidermidis Plank | S. epidermidis Biofilm | E. coli Plank | E. coli Biofilm | | |
|---|---|---|---|---|---|---|---|---|---|---|
| 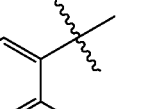 Nitazoxanide | 52.1 | 13.0 | 39.1 | 39.1 | 52.1 | 32.5 | 104.1 | 26.0 | 100 | 100 |
| 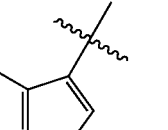 VPC16a1014 | — | 1.2 | 19.9 | 105.9 | 5.0 | — | 105.9 | — | — | — |
| 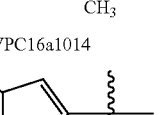 VPC16b1028 | — | 1.2 | 39.7 | 105.9 | 105.9 | — | 105.9 | — | — | — |
| 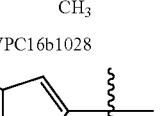 VPC16b1031 | — | 6.9 | 13.9 | 27.8 | 13.9 | — | 111.0 | — | 75 | — |

SUPPLEMENTAL TABLE 7
Carboxylic Acid Analogues of 2-amino-5-nitrothiazole
| R = | MIC (μM) | | | | | | | | Disk Diffusion (%) | Direct PFOR Enzyme Assay (%) |
|---|---|---|---|---|---|---|---|---|---|---|
| | C. difficile | H. pylori | C. jejuni | MRSA | S. epidermidis Plank | S. epidermidis Biofilm | E. coli Plank | E. coli Biofilm | C. difficile | |
| Nitazoxanide 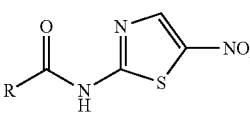 | 52.1 | 13.0 | 39.1 | 39.1 | 52.1 | 32.5 | 104.1 | 26.0 | 100 | 100 |
| VPC161273 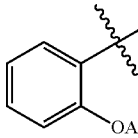 | — | 5.8 | 123.4 | 123.4 | 123.4 | 123.4 | 123.4 | 61.7 | — | — |
| VPC162035  | — | 1.0 | 84.4 | 84.3 | 84.3 | — | 84.3 | — | 0 | — |
| VPC162036 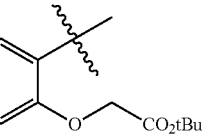 | — | 0.5 | 84.4 | 84.3 | 84.3 | — | 84.3 | — | — | — |
| VPC162042 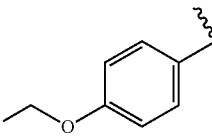 | — | 49.5 | 99.0 | 99.0 | 99.0 | — | 99.0 | — | — | — |
| VPC162043 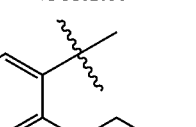 | — | 99.0 | 99.0 | 99.0 | 99.0 | — | 99.0 | — | — | — |
| VPC162056 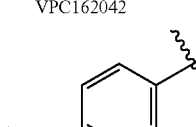 | — | 0.9 | 80.3 | 80.3 | 80.3 | — | 80.3 | — | — | — |
| VPC162064 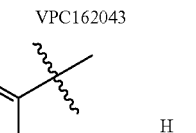 | — | 1.9 | 78.7 | 78.7 | 4.9 | — | 78.7 | — | — | — |

SUPPLEMENTAL TABLE 7-continued
| R = | | | | | | | | | | |
|---|---|---|---|---|---|---|---|---|---|---|
| 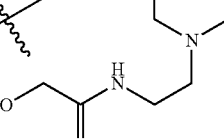 VPC162065 | — | 2.3 | 36.7 | 73.5 | 27.6 | — | 73.5 | — | — | — |
| 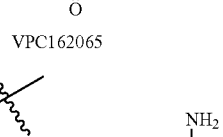 VPC162082 | — | 6.2 | 29.8 | 79.4 | 79.4 | — | 79.4 | — | — | — |
| 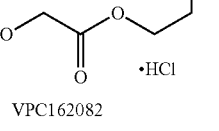 VPC162083 | — | 24.1 | 77.1 | 77.1 | 77.1 | — | 77.1 | — | — | — |
SUPPLEMENTAL TABLE 8
Dimer-like Analogues of 2-amino-5-nitrothiazole
| R = | MIC (µM) | | | | | | | | Disk Diffusion (%) | Direct PFOR Enzyme Assay (%) |
|---|---|---|---|---|---|---|---|---|---|---|
| | C. difficile | H. pylori | C. jejuni | MRSA | S. epidermidis Plank | S. epidermidis Biofilm | E. coli Plank | E. coli Biofilm | C. difficile | |
| 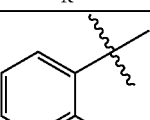 Nitazoxanide | 52.1 | 13.0 | 39.1 | 39.1 | 52.1 | 32.5 | 104.1 | 26.0 | 100 | 100 |
|  VPC16b1048 | — | 20.7 | 82.8 | 82.8 | 82.8 | 41.4 | 82.8 | 82.8 | — | — |
| 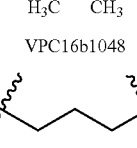 VPC161276 | — | 5.2 | 31.1 | 82.8 | 82.8 | 1.3 | 82.8 | 82.8 | — | — |
| 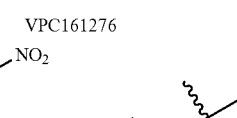 VPC161277 | — | 1.8 | 29.1 | 77.6 | 77.6 | 2.4 | 77.6 | 77.6 | — | — |

SUPPLEMENTAL TABLE 9

Halide Analogues of 2-amino-5-nitrothiazole

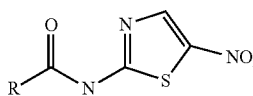

| R = | MIC (µM) | | | | | | | | Disk Diffusion (%) | Direct PFOR Enzyme Assay (%) |
|---|---|---|---|---|---|---|---|---|---|---|
| | C. difficile | H. pylori | C. jejuni | MRSA | S. epidermidis Plank | S. epidermidis Biofilm | E. coli Plank | E. coli Biofilm | C. difficile | |
| 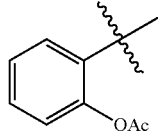 Nitazoxanide | 52.1 | 13.0 | 39.1 | 39.1 | 52.1 | 32.5 | 104.1 | 26.0 | 100 | 100 |
| 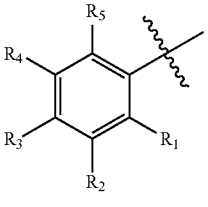 | — | 0.5 | 5.6 | 18.7 | 119.7 | 59.9 | 119.7 | 119.7 | — | — |
| $R_1$ = F; $R_{2-5}$ = H VPC161152 | | | | | | | | | | |
| $R_2$ = F; $R_{1,3-5}$ = H VPC161166 | — | 0.9 | 11.2 | 16.8 | 22.5 | 59.9 | 119.7 | 59.9 | — | — |
| $R_3$ = F; $R_{1,2,4,5}$ = H VPC161167 | — | 0.9 | 2.8 | 8.4 | 15.0 | 29.9 | 119.7 | 119.7 | 89 | 99 |
| $R_{1,3}$ = F; $R_{2,4,5}$ = H VPC16b1009 | — | 0.4 | 7.0 | 28.0 | 42.1 | — | 112.2 | — | — | — |
| $R_{3,4}$ = F; $R_{1,2,5}$ = H VPC16b1019 | — | 1.8 | 5.3 | 10.5 | 28.0 | — | 84.1 | — | — | — |
| $R_{1,5}$ = F; $R_{2-4}$ = H VPC16b1010 | — | 0.7 | 14.0 | 28.0 | 28.0 | — | 112.2 | — | — | — |
| $R_{1,3,5}$ = F; $R_{2,4}$ = H VPC16b1011 | — | 4.9 | 9.9 | 39.6 | 52.8 | — | 105.5 | — | — | — |
| $R_{2,4}$ = F; $R_{1,5}$ = H VPC16b1014 | — | 1.2 | 4.9 | 29.7 | 66.0 | — | 105.5 | — | — | — |
| $R_{1,3,4}$ = F; $R_{2,5}$ = H VPC16b1012 | — | 0.8 | 9.9 | 33.0 | 33.0 | — | 105.5 | — | — | — |
| $R_{1-4}$ = F; $R_5$ = H VPC16b1013 | — | 1.2 | 4.7 | 6.2 | 12.5 | — | 99.6 | — | — | — |
| $R_{2-5}$ = F VPC161108 | — | 7.4 | 23.6 | 8.8 | 47.2 | 6.6 | 94.3 | 47.2 | — | — |
| $R_1$ = Cl; $R_{2-5}$ = H VPC161162 | — | 0.3 | 7.8 | 3.9 | 20.9 | 20.9 | 83.4 | 83.4 | — | — |
| $R_2$ = Cl; $R_{1,3-5}$ = H VPC161157 | — | 1.0 | 6.5 | 7.8 | 31.3 | 20.9 | 83.4 | 41.7 | — | — |
| $R_3$ = Cl; $R_{1,2,4,5}$ = H VPC161160 | — | 0.7 | 6.5 | 2.0 | 26.1 | 5.2 | 62.6 | 41.7 | — | — |

SUPPLEMENTAL TABLE 10

Monosubstituted Analogues of 2-amino-5-nitrothiazole

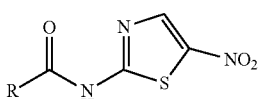

| R = | MIC (μM) C. difficile | H. pylori | C. jejuni | MRSA | S. epidermidis Plank | S. epidermidis Biofilm | E. coli Plank | E. coli Biofilm | Disk Diff (%) C. difficile | Direct PFOR Enzyme Assay (%) |
|---|---|---|---|---|---|---|---|---|---|---|
| 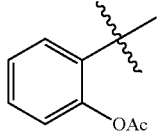 Nitazoxanide | 52.1 | 13.0 | 39.1 | 39.1 | 52.1 | 32.5 | 104.1 | 26.0 | 100 | 100 |
| 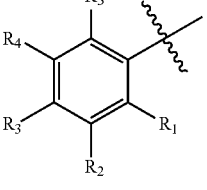 | | | | | | | | | | |
| $R_2$ = CN; $R_{1,3-5}$ = H  VPC161173 | — | 4.1 | 36.5 | 43.8 | 29.2 | 58.3 | 116.7 | 116.7 | — | — |
| $R_3$ = CN; $R_{1,2,4,5}$ = H  VPC161086 | — | 9.1 | 43.8 | 14.6 | 21.9 | 4.6 | 87.5 | 58.3 | — | 74 |
| $R_1$ = $CF_3$; $R_{2-5}$ = H  VPC161182 | — | 1.6 | 18.9 | 25.2 | 25.2 | 50.4 | 100.9 | 100.9 | — | — |
| $R_2$ = $CF_3$; $R_{1,3-5}$ = H  VPC161183 | 12.6 | 3.5 | 4.7 | 3.2 | 12.6 | 25.2 | 37.8 | 31.5 | 95 ± 2 | 87 |
| $R_3$ = $CF_3$; $R_{1,2,4,5}$ = H  VPC161184 | — | 1.6 | 4.7 | 100.9 | 12.6 | 12.6 | 63.0 | 12.6 | 90 | — |
| $R_1$ = $NO_2$; $R_{2-5}$ = H  VPC161168 | — | 1.7 | 27.2 | 108.8 | 40.8 | 68.0 | 108.8 | 108.8 | — | — |
| $R_2$ = $NO_2$; $R_{1,3-5}$ = H  VPC161169 | — | 1.3 | 27.2 | 10.2 | 10.2 | 3.4 | 81.6 | 108.8 | — | — |
| $R_3$ = $NO_2$; $R_{1,2,4,5}$ = H  VPC161170 | — | 1.3 | 13.6 | 20.4 | 10.2 | 3.4 | 81.6 | 108.8 | — | — |
| $R_1$ = OMe; $R_{2-5}$ = H  VPC161192 | — | 1.8 | 17.9 | 114.6 | 114.6 | 114.6 | 114.6 | 57.3 | — | — |
| $R_2$ = OMe; $R_{1,3-5}$ = H  VPC161193 | 28.6 | 1.3 | 7.2 | 14.3 | 28.6 | 57.3 | 114.6 | 114.6 | 73 ± 1 | 82 |
| $R_3$ = OMe; $R_{1,2,4,5}$ = H  VPC161194 | — | 1.8 | 4.5 | 28.6 | 28.6 | 28.6 | 114.6 | 114.6 | — | 84 |
| $R_3$ = $C(O)CF_3$; $R_{1,2,4,5}$ = H  VPC161175 | 23.2 | 4.3 | 69.5 | 92.7 | 92.7 | 92.7 | 92.7 | 92.7 | — | — |
| $R_2$ = $OCF_3$; $R_{1,3-5}$ = H  VPC16a1041 | — | 1.1 | 9.0 | 6.0 | 12.0 | — | 96.0 | — | 90 | — |

SUPPLEMENTAL TABLE 11

Disubstituted Analogues of 2-amino-5-nitrothiazole

| R = | MIC (µM) | | | | | | | Disk Diff (%) | Direct PFOR Enzyme Assay (%) |
|---|---|---|---|---|---|---|---|---|---|
| | C. difficile | H. pylori | C. jejuni | MRSA | S. epidermidis Plank | S. epidermidis Biofilm | E. coli Plank | E. coli Biofilm | C. difficile | |
| Nitazoxanide (2-OAc phenyl) | 52.1 | 13.0 | 39.1 | 39.1 | 52.1 | 32.5 | 104.1 | 26.0 | 100 | 100 |
| $R_1$ = OAc; $R_3$ = CN; $R_{2,4,5}$ = H  VPC161076 | — | 24.1 | 96.3 | 96.3 | 96.3 | 48.2 | 96.3 | 96.3 | — | — |
| $R_4$ = $CF_3$; $R_5$ = Cl; $R_{1-3}$ = H  VPC16a1059 | — | 0.9 | 92.1 | 92.1 | 92.1 | 92.1 | 92.1 | 92.1 | — | — |
| $R_1$ = OMe; $R_3$ = $NO_2$; $R_{2,4,5}$ = H  VPC161093 | 98.7 | 0.6 | 9.3 | 98.7 | 12.3 | 12.3 | 98.7 | 98.7 | — | 115 |
| $R_1$ = OMe; $R_4$ = o,p-DifluoroPh; $R_{2,3,5}$ = H  VPC161171 | — | 0.8 | 40.9 | 81.8 | 81.8 | 81.8 | 81.8 | 81.8 | — | — |
| $R_1$ = OH; $R_2$ = $NO_2$; $R_{3-5}$ = H  VPC161090 | — | 19.3 | 103.1 | 103.1 | 77.4 | 6.4 | 103.1 | 103.1 | — | — |
| $R_1$ = $CF_3$; $R_2$ = F; $R_{2,4,5}$ = H  VPC161127 | — | 3.4 | 23.9 | 8.9 | 23.9 | 13.4 | 95.5 | 95.5 | — | — |
| $R_1$ = $NO_2$; $R_3$ = $CF_3$; $R_{2,4,5}$ = H  VPC16b1016 | — | 8.3 | 88.3 | 88.3 | 88.3 | — | 88.3 | 88.3 | — | — |
| $R_2$ = $NO_2$; $R_3$ = F; $R_{1,5,6}$ = H  VPC16b1017 | — | 1.6 | 51.2 | 76.9 | 51.2 | — | 102.5 | 102.5 | — | — |
| $R_{2,4}$ = $CF_3$; $R_{1,3,5}$ = H  VPC16a1039 | — | 5.2 | 41.5 | 2.6 | 1.9 | — | 83.1 | — | 80 | 54* |
| $R_1$ = Cl; $R_4$ = $CF_3$; $R_{2,3,5}$ = H  VPC16a1040 | — | 1.1 | 17.1 | 22.7 | 22.7 | — | 91.0 | — | 90 | 68 |
| $R_4$ = $CF_3$; $R_5$ = Cl; $R_{1-3}$ = H  VPC16a1059 | — | 0.9 | 5.7 | 11.4 | 11.4 | — | 91.0 | — | 90 | — |
| $R_3$ = Cl; $R_4$ = $CF_3$; $R_{1,2,5}$ = H  VPC16a1060 | — | 2.8 | 2.8 | 2.8 | 2.8 | — | 91.0 | — | 89 | 63* |

*Caused some precipitate in extract

SUPPLEMENTAL TABLE 12
Furan Analogues of 2-amino-5-nitrothiazole
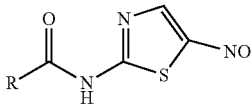
| R = | MIC (μM) | | | | | | | | Disk Diff (%) | Direct PFOR Enzyme Assay (%) |
|---|---|---|---|---|---|---|---|---|---|---|
| | *C. difficile* | *H. pylori* | *C. jejuni* | MRSA | *S. epidermidis* Plank | *S. epidermidis* Biofilm | *E. coli* Plank | *E. coli* Biofilm | *C. difficile* | |
| 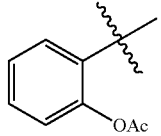<br>Nitazoxanide | 52.1 | 13.0 | 39.1 | 39.1 | 52.1 | 32.5 | 104.1 | 26.0 | 100 | 100 |
| 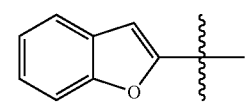<br>VPC161144 | — | 0.6 | 110.6 | 57.0 | 110.6 | 110.6 | 110.6 | 110.6 | — | 70 |
| 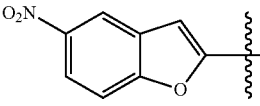<br>VPC16a1019 | — | 4.5 | 4.5 | 47.9 | 23.9 | — | 95.7 | — | 77 | — |
| 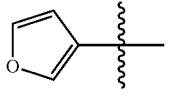<br>VPC16a1006 | 33.4 | 0.8 | 12.5 | 50.2 | 33.4 | — | 133.8 | 133.8 | 97 ± 3 | 98 |
| 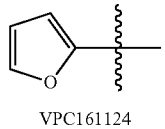<br>VPC161124 | — | 1.0 | 8.4 | 50.2 | 66.9 | 66.9 | 133.8 | 33.4 | 100 | 82 |
| 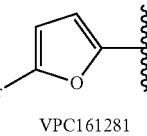<br>VPC161281 | — | 1.6 | 12.6 | 6.3 | 25.1 | 50.3 | 100.6 | 0.4 | 92 | — |
| 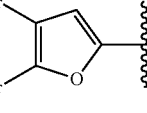<br>VPC161164 | — | 2.8 | 20.2 | 3.8 | 15.1 | 20.2 | 60.5 | 40.3 | — | 56 |
| 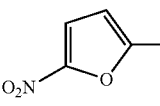<br>VPC16b1007 | 28.2 | 21.1 | 7.0 | 112.6 | 28.1 | 56.3 | 14.1 | 26.4 | 102 ± 8 | — |
| 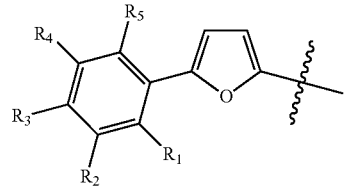<br>$R_{1-5}$ = H<br>VPC16c1020 | — | 2.4 | 101.5 | 101.5 | 101.5 | — | 101.5 | — | — | — |
| $R_3$ = $NO_2$; $R_{1,2,4,5}$ = H<br>VPC161189 | — | 6.9 | 16.7 | 88.8 | 11.1 | 11.1 | 88.8 | 88.8 | — | — |

SUPPLEMENTAL TABLE 12-continued

Furan Analogues of 2-amino-5-nitrothiazole

| | | | | | | | | | |
|---|---|---|---|---|---|---|---|---|---|
| $R_2$ = $NO_2$; $R_{1,3-5}$ = H<br>VPC161190 | — | 6.9 | 16.7 | 44.4 | 11.1 | 11.1 | 88.8 | 88.8 | — | — |
| $R_1$ = $CF_3$; $R_{2-5}$ = H<br>VPC161196 | — | 1.1 | 8.5 | 2.8 | 5.7 | 5.7 | 90.8 | 90.8 | 70.5 ± 0.5 | — |
| $R_2$ = $CF_3$; $R_{1,3-5}$ = H<br>VPC161197 | — | 1.1 | 8.5 | 11.4 | 5.7 | 5.7 | 90.8 | 90.8 | — | — |
| $R_1$ = $CH_3$; $R_{2-5}$ = H<br>VPC16a1103 | — | 3.8 | 24.3 | 12.1 | 12.1 | — | 97.2 | — | — | — |
| $R_2$ = $CH_3$; $R_{1,3-5}$ = H<br>VPC16b2014 | — | 2.3 | 97.2 | 97.2 | 97.2 | — | 97.2 | — | — | — |
| $R_3$ = $CH_3$; $R_{1,2,4,5}$ = H<br>VPC16b2019 | — | 1.5 | 97.2 | 97.2 | 97.2 | — | 97.2 | — | — | — |
| $R_2$ = F; $R_{1,3-5}$ = H<br>VPC16b1115 | — | 1.5 | 24.0 | 24.0 | 12.0 | — | 96.0 | — | — | — |
| $R_3$ = F; $R_{1,2,4,5}$ = H<br>VPC16a1104 | — | 1.0 | 96.0 | 96.0 | 96.0 | — | — | — | — | 81 |
| $R_1$ = Cl; $R_{2-5}$ = H<br>VPC16b1118 | — | 1.4 | 11.4 | 11.4 | 5.7 | — | 91.5 | — | — | — |
| $R_2$ = Cl; $R_{1,3-5}$ = H<br>VPC16b1119 | — | 1.1 | 22.9 | 91.5 | 91.5 | — | 91.5 | — | — | — |
| $R_3$ = Cl; $R_{1,2,4,5}$ = H<br>VPC16a1012 | — | 1.1 | 8.6 | 2.9 | 2.9 | — | 91.5 | — | 60.5 ± 4.5 | — |
| $R_3$ = OMe; $R_{1,2,4,5}$ = H<br>VPC16b1139 | — | 1.5 | 92.7 | 92.7 | 92.7 | — | 92.7 | — | — | — |
| $R_{3-4}$ = —$OCH_2O$—;<br>$R_{1,2,5}$ = H<br>VPC16b1132 | — | 1.4 | 89.1 | 89.1 | 89.1 | — | 89.1 | — | — | — |
| 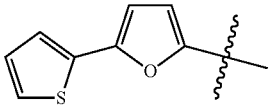<br>VPC16b1145 | — | 1.9 | 12.5 | 12.4 | 12.4 | — | 99.6 | — | — | — |
| 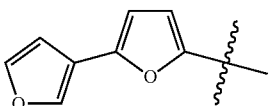<br>VPC16b1142 | — | 1.6 | 13.1 | 26.2 | 13.1 | — | 104.8 | — | — | — |
| 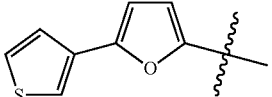<br>VPC16b2022 | — | 6.2 | 99.6 | 99.6 | 99.6 | — | 99.6 | — | — | — |

SUPPLEMENTAL TABLE 13
Thiophene Analogues of 2-amino-5-nitrothiazole
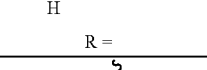
| R = | MIC (μM) | | | | | | | | Disk Diff (%) C. difficile | Direct PFOR Enzyme Assay (%) |
|---|---|---|---|---|---|---|---|---|---|---|
| | C. difficile | H. pylori | C. jejuni | MRSA | S. epidermidis | | E. coli | | | |
| | | | | | Plank | Biofilm | Plank | Biofilm | | |
| 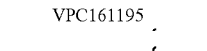<br>Nitazoxanide | 52.1 | 13.0 | 39.1 | 39.1 | 52.1 | 32.5 | 104.1 | 26.0 | 100 | 100 |
| 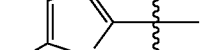<br>VPC161195 | 31.3 | 2.9 | 2.9 | 15.7 | 31.3 | 62.7 | 125.4 | 125.4 | 97 | 88 |
| 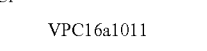<br>VPC16a1011 | 6.9 | 5.2 | 6.9 | 10.4 | 27.6 | — | 110.5 | 0.9 | 89 | 65 |
| 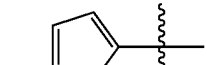<br>VPC161282 | — | 3.0 | 9.9 | 4.5 | 23.9 | 47.9 | 95.8 | 0.1 | 90 | — |
| 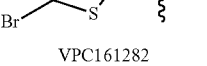<br>VPC16a1009 | — | 5.2 | 20.7 | 20.7 | 55.2 | — | 110.5 | — | — | — |
| <br>VPC16a1008 | 12.3 | 0.7 | 5.9 | 23.5 | 15.7 | — | 125.4 | — | 100 | 96 |
| 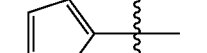<br>VPC161199 | — | 1.5 | 2.3 | 6.2 | 12.3 | 24.7 | 98.7 | 24.7 | 89 | 48 |
| 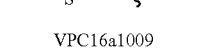<br>VPC161280 | — | 6.6 | 13.3 | 53.1 | 5.0 | 6.6 | 39.8 | 3.3 | — | — |
| 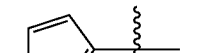<br>VPC161180 | 13.1 | 2.5 | 9.8 | 6.6 | 13.1 | 19.7 | 104.8 | 104.8 | 81 | — |

SUPPLEMENTAL TABLE 13-continued

Thiophene Analogues of 2-amino-5-nitrothiazole

| Structure / Compound | | | | | | | | | | |
|---|---|---|---|---|---|---|---|---|---|---|
| VPC161181 (3-Cl-benzothiophene) | 11.8 | 2.2 | 5.9 | 2.9 | 5.9 | 11.8 | 94.2 | 94.2 | 72 | — |
| VPC162037 (6-F-benzothiophene) | — | 3.1 | 6.2 | 61.9 | 49.5 | — | 99.0 | — | 70 | — |
| VPC161115 (3-Cl, 6-F-benzothiophene) | 11.2 | 1.0 | 5.6 | 2.1 | 5.6 | 0.1 | 89.4 | 5.6 | 44 | 96 |
| VPC161259 (5-MeO, 6-F-benzothiophene) | — | 2.1 | 11.3 | 11.3 | 11.3 | — | 90.6 | — | — | — |
| $R_2 = CH_3$; $R_{1,3-5} = H$ VPC16b2011 | — | 2.2 | 92.6 | 92.6 | 92.6 | — | 92.6 | — | — | — |
| $R_3 = CH_3$; $R_{1,2,4,5} = H$ VPC16b2020 | — | 0.9 | 92.6 | 92.6 | 92.6 | — | 92.6 | — | — | — |
| $R_2 = Cl$; $R_{1,3-5} = H$ VPC16c1033 | — | 0.7 | 5.5 | 87.5 | 87.5 | — | — | — | — | 84 |
| VPC16b2021 (bithiophene) | — | 3.0 | 94.8 | 94.8 | 94.8 | — | 94.8 | — | — | — |
| VPC16b1148 (furan-thiophene) | — | 7.8 | 12.4 | 24.9 | 12.4 | — | 99.6 | — | — | — |
| VPC16b1154 (3-thienyl-thiophene) | — | 3.0 | 94.8 | 94.8 | 94.8 | — | 94.8 | — | — | — |

SUPPLEMENTAL TABLE 13-continued
Thiophene Analogues of 2-amino-5-nitrothiazole
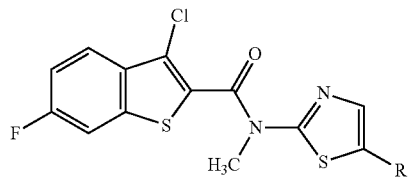
R = NO₂
VPC161269
| — | 1.0 | 53.8 | 86.1 | 86.1 | 86.1 | 86.1 | 86.1 | 21.5 | — |
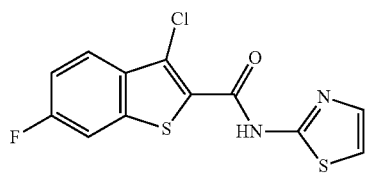
VPC161235
| — | 12.8 | 102.3 | 102.3 | 102.3 | — | 102.3 | — | — | — |
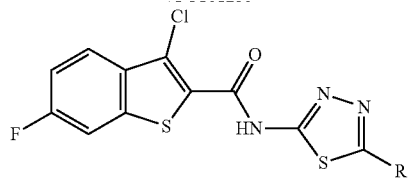
R = p-NO₂Ph
VPC161237
| — | 73.6 | 73.6 | 73.6 | 73.6 | — | 73.6 | — | — | — |
SUPPLEMENTAL TABLE 14
Amide Isosteres of 2-amino-5-nitrothiazole
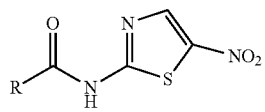
| R = | MIC (μM) | | | | | | | Disk Diffusion (%) | Direct PFOR Enzyme Assay (%) |
|---|---|---|---|---|---|---|---|---|---|
| | C. difficile | H. pylori | C. jejuni | MRSA | S. epidermidis Plank | S. epidermidis Biofilm | E. coli Plank | E. coli Biofilm | C. difficile | |
Nitazoxanide
| 52.1 | 13.0 | 39.1 | 39.1 | 52.1 | 32.5 | 104.1 | 26.0 | 100 | 100 |
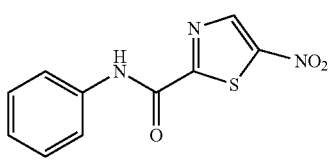
VPC161232
| — | 6.0 | 8.0 | 32.1 | 16.0 | — | 128.4 | — | 0 | — |
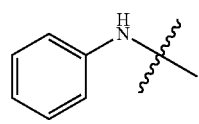
VPC161223
| — | 1.4 | 30.3 | 30.3 | 30.3 | — | 121.1 | — | — | — |

SUPPLEMENTAL TABLE 14-continued

Amide Isosteres of 2-amino-5-nitrothiazole

| R | | C. difficile | H. pylori | C. jejuni | MRSA | S. epidermidis Plank | S. epidermidis Biofilm | E. coli Plank | E. coli Biofilm | Disk Diff (%) C. difficile | Direct PFOR Enzyme Assay (%) |
|---|---|---|---|---|---|---|---|---|---|---|---|
| 4-F-C6H4-NH- (VPC161267) | | — | 0.9 | 21.3 | 56.7 | 28.3 | 28.3 | 113.4 | 56.7 | — | — |

SUPPLEMENTAL TABLE 15

Analogues of 2-amino-4-chloro-5-nitrothiazole

| R = | C. difficile | H. pylori | C. jejuni | MRSA | S. epidermidis Plank | S. epidermidis Biofilm | E. coli Plank | E. coli Biofilm | Disk Diff (%) C. difficile | Direct PFOR Enzyme Assay (%) |
|---|---|---|---|---|---|---|---|---|---|---|
| 2-OAc-C6H4- (Nitazoxanide) | 52.1 | 13.0 | 39.1 | 39.1 | 52.1 | 32.5 | 104.1 | 26.0 | 100 | 100 |
| H3C-(CH2)n- , n = 4 (VPC162080) | — | 0.9 | 3.6 | 43.2 | 14.4 | — | 115.2 | — | 72 | 116* |
| C6H5- (VPC162087) | — | 8.8 | 7.1 | 112.8 | 35.2 | — | 112.8 | — | 66 | 107 |
| 3-CF3-C6H4- (VPC162088) | — | 5.7 | 34.1 | 11.4 | 8.5 | — | 91.0 | — | 76 | 49** |
| 2-thienyl- (VPC162089) | — | 6.9 | 13.8 | 110.5 | 82.8 | — | 110.5 | — | — | 93 |

*Biphasic initial inhibition followed by uninhibited rate
**Caused some precipitant in extract

SUPPLEMENTAL TABLE 16
Analogues of 2-amino-3,5-dinitrothiophene
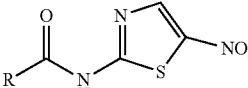
R=
| R = | MIC (µM) | | | | | | | Disk Diff (%) C. difficile | Direct PFOR Enzyme Assay (%) |
|---|---|---|---|---|---|---|---|---|---|
| | C. difficile | H. pylori | C. jejuni | MRSA | S. epidermidis Plank / Biofilm | | E. coli Plank / Biofilm | | |
| 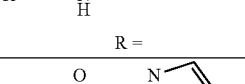  Nitazoxanide | 52.1 | 13.0 | 39.1 | 39.1 | 52.1 / 32.5 | | 104.1 / 26.0 | 100 | 100 |
| 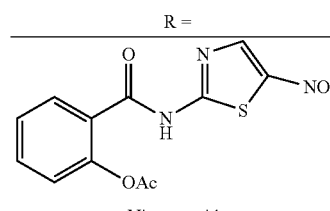  n = 4  VPC16b1089 | — | 2.6 | 0.9 | 55.7 | 20.9 / — | | 111.4 / — | 42 | 148* |
| 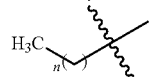  VPC16b1090 | — | 1.3 | 0.9 | 109.1 | 5.1 / — | | 109.1 / — | 0 | 100** |
| 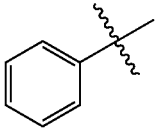  VPC16b1092 | — | 0.5 | 2.1 | 1.4 | 0.2 / — | | 88.6 / — | 59 | 87** |
| 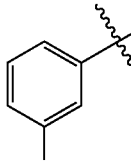  VPC16b1093 | — | 2.5 | 1.0 | 26.7 | 13.4 / — | | 106.9 / — | 43 | 143 |
| 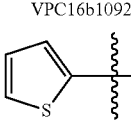  VPC16b1094 | — | 2.7 | 0.4 | 56.5 | 28.2 / — | | 113.0 / — | 53 | 126* |
| 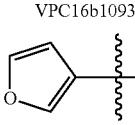  VPC16b2023 | — | 2.1 | 2.8 | 33.1 | 88.4 / — | | — / — | — | 94** |
| 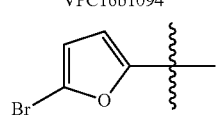  VPC16b2025 | — | 2.6 | 2.6 | 63.5 | 15.9 / — | | — / — | — | 98** |
| 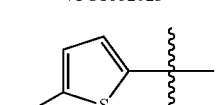  VPC16b2026 | — | 0.8 | 2.5 | 30.3 | 15.2 / — | | — / — | — | 100 |

SUPPLEMENTAL TABLE 16-continued

Analogues of 2-amino-3,5-dinitrothiophene

| Structure | | | | | | | | | | |
|---|---|---|---|---|---|---|---|---|---|---|
| 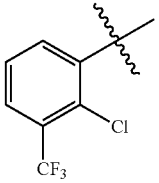 VPC16b2028 | — | 0.8 | 1.9 | 30.3 | 30.3 | — | — | — | — | 113 |
| 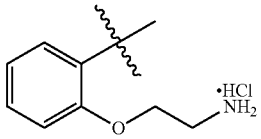 VPC16b2031 | — | 1.9 | 1.3 | 82.3 | 25.7 | — | — | — | — | 162 |

*Biphasic initial inhibition followed by uninhibited rate
**Caused some precipitant in extract The disclosures of each and every patent, patent application, and publication cited herein are hereby incorporated by reference herein in their entirety.

Headings are included herein for reference and to aid in locating certain sections. These headings are not intended to limit the scope of the concepts described therein under, and these concepts may have applicability in other sections throughout the entire specification.

While this invention has been disclosed with reference to specific embodiments, it is apparent that other embodiments and variations of this invention may be devised by others skilled in the art without departing from the true spirit and scope of the invention.

BIBLIOGRAPHY

1. Boisen, N., C. Struve, F. Scheutz, K. A. Krogfelt, and J. P. Nataro. 2008. New adhesion of enteroaggregative *Escherichia coli* related to the Afa/Dr/AAF family. Infect. Immun. 76:3281-3292.
2. Clarke, S. C. 2001. Diarrhoeagenic *Escherichia coli*—an emerging problem? Diagn. Microbiol. Infect. Dis. 41:93-98.
3. Czeczulin, J. R., Balepur, S., Hicks, S., Phillips, A., Hall, R., Kothary, M. H., et al. (1997) Aggregative adherence fimbria II, a second fimbrial antigen mediating aggregative adherence in enteroaggregative *Escherichia coli*. Infect Immun 65: 4135-4145.
4. de Onis, M., M. Blossner, E. Borghi, R. Morris, and E. A. Frongillo. 2004. Methodology for estimating regional and global trends of child malnutrition. Int. J. Epidemiol. 33:1260-70.
5. Dodd, D. C., and B. I. Eisenstein. 1982. Antigenic quantitation of Type I fimbriae on the surface of *Escherichia coli* cells by an enzyme-linked immunosorbent inhibition assay. Infect. Immun. 38:764-773.
6. DuPont, H. L., C. D. Ericsson, P. C. Johnson, and F. E. de la Cablda. 1990. Use of bismuth subsalicylate for the prevention of travellers' diarrhea. Rev. Infect. Dis. 12(suppl. 1):S64-S67.
7. Elias, W. P. Jr, J. R. Czeczulin, I. R. Henderson, L. R. Trabulsi, and J. P. Nataro. 1999. Organization of biogenesis genes for aggregative adherence fimbria II defines a virulence gene cluster in enteroaggregative *Escherichia coli*. J. Bacteriol. 181:1779-85.
8. Fox, L. M., and L. D. Saravolatz. 2005. Nitazoxanide: A New Thiazolide Antiparasitic Agent. Clin. Infect. Dis. 40:1173-80.
9. Glandt, M., J. A. Adachi, J. J. Mathewson, Z. D. Jiang, D. DiCesare, D. Ashley, C. D. Ericsson, and H. L. DuPont. 1999. Enteroaggregative *Escherichia coli* as a cause of traveler's diarrhea: clinical response to ciprofloxacin. Clin. Infect. Dis. 29:335-8.
10. Guerrant, R. L., et al. 2001. Practice guidelines for the management of infectious diarrhea. Clin. Infect. Dis. 32:331-51.
11. Guerrant, R. L., M. Kosek, A. A. M. Lima, B. Lorntz, and H. L. Guyatt. 2002. Updating the DALYs for diarrhoeal disease. Trends Parasitol. 18:191-3.
12. Harrington, S. M., E. G. Dudley, and J. P. Nataro. 2006. Pathogenesis of enteroaggregative *Escherichia coli* infection. FEMS Microbiol. Lett. 254:12-18.
13. Hemphill, A., J. Mueller, and M. Esposito. 2006. Nitazoxanide, a broad-spectrum thiazolide anti-infective agent for the treatment of gastrointestinal infections. Expert Opin Pharmacother. 7:953-964.
14. Hoffman, P. S., C. A. Butler, and F. D. Quinn. 1989. Cloning and temperature-dependent expression in *Escherichia coli* of a *Legionella pneumophila* gene coding for a genus-common 60-kilodalton antigen. Infect. Immun. 57:1731-1739.
15. Hoffman, P. S., J. H. Seyer, and C. A. Butler. 1992. Molecular characterization of the 28 and 31 kilodalton subunits of the *Legionella pneumophila* porin. J. Bacteriol. 174:908 913.
16. Hoffman, P. S., G. Sisson, M. A. Croxen, K. Welch, W. D. Harman, N. Cremades, and M. G. Morash. 2007. Antiparastic drug nitazoxanide inhibits the pyruvate oxidoreductases of *Helicobacter pylori*, selected anaerobic bacteria and parasites, and *Campylobacter jejuni*. Antimicrob. Agents Chemother. 51:868-876.
17. Huang, D. B., and H. L. DuPont. 2004. Enteroaggregative *Escherichia coli*: An emerging pathogen in children. Semin. Pediatr. Infect. Dis. 15:266-271.
18. Huang, D. V., A. Mohanty, H. L. DuPont, P. C. Okhuysen, and T. Chiang. 2006. A review of an emerging enteric pathogen: enteroaggregative *Escherichia coli*. J. Med. Microbiol. 55:1303-11.

19. Infante, R. M., C. D. Ericsson, Z. D. Jiang, S. Ke, R. Steffen, L. Riopel, D. A. Sack, and H. L. DuPont. 2004. Enteroaggregative *Escherichia coli* diarrhea in travelers: response to rifaximin therapy. Clin. Gastroenterol. Hepatol. 2:135-8.
20. Jacob-Dubuisson, F., J. Pinkner, Z. Xu, R. Striker, A. Padmanhaban, and S. J. Hultgren. 1994. PapD chaperone function in pilus biogenesis depends on oxidant and chaperone-like activities of DsbA. Proc Natl Acad Sci USA. 91:11552-11556.
21. Kosek, M., C. Bern, and R. L. Guerrant. 2003. The global burden of diarrhoeal disease, as estimated from studies published between 1992 and 2000. Bull. World Health Organ. 81:197-204.
22. Louis, P., K. P. Scott, S. H. Duncan, and H. J. Flint. 2007. Understanding the effects of diet on bacterial metabolism in the large intestine. J Appl Microbiol. 102:1197-1208.
23. Manoil, C., and J. Beckwith. 1985. TnphoA: a transposon probe for protein export signals. Proc. Natl. Acad. Sci. USA 82:8129-8133.
24. Miller, J. H. 1972. Experiments in molecular genetics. Cold Spring Harbor Laboratory, Cold spring Harbor, N.Y.
25. Mohamed, J. A., D. B. Huang, Z. Jiang, H. L. DuPont, J. P. Nataro, J. Belkind-Gerson, and P. C. Okhuysen. 2007. Association of putative enteroaggregative *Escherichia coli* virulence genes and biofilm production in isolates from travelers to developing countries. J. Clin. Microbiol. 45:121-126.
26. Moreira, C. G., S. M. Carneiro, J. P. Nataro, L. R. Trabulsi, and W. P. Elias. 2003. Role of type I fimbriae in the aggregative adhesion pattern of enteroaggregative *Escherichia coli*. FEMS Microbiol. Lett. 226:79-85.
27. Musher, D. M., N. Logan, A. M. Bressler, D. P. Johnson, J. F. Rossignol. 2009. Nitazoxanide versus vancomycin in *Clostridium difficile* infection: A randomized, double-blind study. Clin Infect Dis. 48:41-46.
28. Nataro, J. P. 2005. Enteroaggregative *Escherichia coli* pathogenesis. Curr. Opin. Gastroenterol. 21:4-8.
29. Nataro, J. P., J. B. Kaper, R. Robins-Browne, V. Prado, P. Vial, and M. M. Levine. 1987. Patterns of adherence of diarrheagenic *Escherichia coli* to HEp-2 cells. Pediatr. Infect. Dis. J. 6:829-831.
30. Nataro, J. P., D. Yikang, D. Yingkang, and K. Walker. 1994. AggR, a transcriptional activator of aggregative adherence fimbria I expression in enteroaggregative *Escherichia coli*. J. Bacteriol. 176:4691-4699.
31. Pinkner, J. S., H. Remaut, F. Buelens, E. Miller, V. Aberg, N. Pemberton, M. Hedenstrim, A. Larsson, P. Seed, G. Waksman, S. J. Hultgren, and F. Almqvist. 2006. Rationally designed small compounds inhibit pilus biogenesis in uropathogenic bacteria. Proc Natl Acad Sci USA. 103: 17897-17902.
32. Pupo, G. M., D. K. R. Karadis, R. Lan, and P. R. Reeves. 1997. Evolutionary relationships among pathogenic and non-pathogenic *Escherichia coli* strains inferred from multilocus enzyme electrophoresis and mdh sequence studies. Infect. Immun. 64:2685-2692.
33. Remaut, H., C. Tang, N. S. Henderson, J. S. Pinkner, T. Wang, S. J. Hultgren, D. G. Thanassi, G. Waksman, and H. Li. 2009. Fiber formation across the bacterial outer membrane by the chaperone/usher pathway. Cell. 133:640-652.
34. Ricci, K. A., F. Girosi, P. I. Tarr, Y. Lim, C. Mason, M. Miller, J. Hughes, L. Seidlein, J. M. Agosti, and R. L. Guerrant. 2006. Reducing stunting among children: the potential contribution of diagnostics. Nature 444:29-38.
35. Ruiz-Perez F., J. Sheikh, S. Davis, E. C. Boedeker, and J. P. Nataro. 2004. Use of a continuous-flow anaerobic culture to characterize enteric virulence gene expression. Infect. Immun. 72:3793-3802.
36. Sarantuya, J., J. Nishi, N. Wakimoto, S. Erdene, J. P. Nataro, J. Sheikh, M. Iwashita, K. Manago, K. Tokuda, M. Yoshinaga, K. Miyata, and Y. Kawano. 2004. Typical enteroaggregative *Escherichia coli* is the most prevalent pathotype among *E. coli* strains causing diarrhea in Mongolian children. J. Clin. Microbiol. 42:133-139.
37. Sheikh, J., S. Hicks, M. Dall'Agnol, A. D. Phillips, and J. P. Nataro. 2001. Roles for Fis and YafK in biofilm formation by enteroaggregative *Escherichia coli*. Mol. Microbiol. 41:983-997.
38. Sisson, G., A. Goodwin, A. Raudonikiene, N. J. Hughes, A. K. Mukhopadhyay, D. E. Berg, and P. S. Hoffman. 2002. Enzymes associated with reductive activation and action of nitazoxanide, nitrofurans, and metronidazole in *Helicobacter pylori*. Antimicrob. Agents Chemother. 46:2116-2123.
39. Steiner, T. S., A. A. Lima, J. P. Nataro, and R. L. Guerrant. 1998. Enteroaggregative *Escherichia coli* produce intestinal inflammation and growth impairment and cause interleukin-8 release from intestinal epithelial cells. J. Infect. Dis. 177:88-96.
40. Velarde J J, Varney K M, Inman K G, Farfan M, Dudley E, Fletcher J, Weber D J, Nataro J P. 2007. Solution structure of the novel dispersin protein of enteroaggregative *Escherichia coli*. Mol. Microbiol. 2007 December; 66(5): 1123-35.
41. Wakimoto, N., J. Nishi, J. Sheikh, J. P. Nataro, J. Sarantuya, M. Iwashita, K. Manago, K. Tokuda, M. Yoshinaga, and Y. Kawano. 2004. Quantitative biofilm assay using a microtiter plate to screen for enteroaggregative *Escherichia coli*. Am. J. Trop. Med. Hyg. 71:687-690.
42. Zhang, H.-Z., and M. S. Donnenberg. 1996. DsbA is required for stability of the type IV pilin of enteropathogenic *Escherichia coli*. Mol. Microbiol. 21:787-797.
43. Zulu, I, P. Kelly, L. Njobvu, S. Sianongo, K. Kaonga, V. McDonald, M. Farthing, and R. Pollok. 2005. Nitazoxanide for persistent diarrhoea in Zambian acquired immune deficiency syndrome patients: a randomized-controlled trial. Aliment Pharmacol Ther. 21:757-763.
44. R. A. Forsch, J. E. Wright, A. Rosowsky, Bioorg. Med. Chem. 2002, 10, 2067.
45. G. D. Beck, Stefan; Brandes, Wilhelm; Paulus, Wilfried, EP0402716 (A1) ed., 1990, p. 61.
46. Hoffman et al., International Patent Publication Number WO 2010/107736 published Sep. 23, 2010 (Int. App. No. PCT/US2010027397).

What is claimed is:

1. A method of treating a *mycobacterium* infection, said method comprising administering to a subject in need thereof a pharmaceutical composition comprising a pharmaceutically-acceptable carrier and an effective amount of a compound selected from the group consisting of:

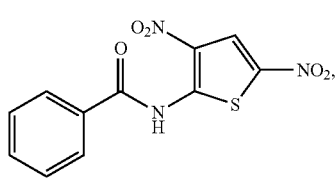

-continued

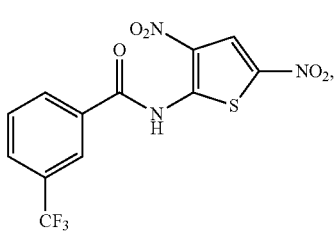
VPC16b1092

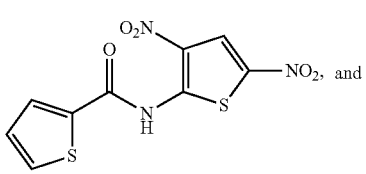
VPC16b1093

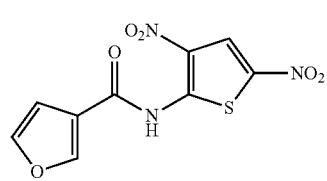
VPC16b1094 and optionally an additional therapeutic agent thereby treating a *mycobacterium* infection.

2. The method of claim 1, wherein said subject is human.

3. The method of claim 1, wherein said *mycobacterium* is selected from the group consisting of *M. tuberculosis, M. bovis, M. bovis* BCG, *M. africanum, M. canetti, M. caprae, M. microti, M. pinnipedii, M. avium, M. avium paratuberculosis, M. avium silvaticum, M. avium "hominissuis", M. colombiense, M. asiaticum, M. gordonae, M. gastri, M. kansasii, M. hiberniae, M. nonchromogenicum, M. terrae, M. triviale, M. ulcerans, M. pseudoshottsii, M. shottsii, M. triplex, M. genavense, M. florentinum, M. lentiflavum, M. palustre, M. kubicae, M. parascrofulaceum, M. heidelbergense, M. interjectum, M. simiae, M. branderi, M. cookii, M. celatum, M. bohemicum, M. haemophilum, M. malmoense, M. szulgai, M. leprae, M. lepraemurium, M. lepromatosis, M. botniense, M. chimaera, M. conspicuum, M. doricum, M. farcinogenes, M. heckeshornense, M. intracellulare, M. lacus, M. marinum, M. monacense, M. montefiorense, M. murale, M. nebraskense, M. saskatchewanense, M. scrofulaceum, M. shimoidei, M. tusciae, M. xenopi, M. intermedium, M. abscessus, M. chelonae, M. bolletii, M. fortuitum, M. fortuitum* subsp. *acetamidolyticum, M. boenickei, M. peregrinum, M. porcinum, M. senegalense, M. septicum, M. neworleansense, M. houstonense, M. mucogenicum, M. mageritense, M. brisbanense, M. cosmeticum, M. parafortuitum, M. austroafricanum, M. diernhoferi, M. hodleri, M. neoaurum, M. frederiksbergense, M. aurum, M. vaccae, M. chitae, M. fallax, M. confluentis, M. flavescens, M. madagascariense, M. phlei, M. smegmatis, M. goodii, M. wolinskyi, M. thermoresistibile, M. gadium, M. komossense, M. obuense, M. sphagni, M. agri, M. aichiense, M. alvei, M. arupense, M. brumae, M. canariasense, M. chubuense, M. conceptionense, M. duvalii, M. elephantis, M. gilvum, M. hassiacum, M. holsaticum, M. immunogenum, M. massiliense, M. moriokaense, M. psychrotolerans, M. pyrenivorans, M. vanbaalenii, M. pulveris, M. arosiense, M. aubagnense, M. caprae, M. chlorophenolicum, M. fluoroanthenivorans, M. kumamotonense, M. novocastrense, M. parmense, M. phocaicum, M. poriferae, M. rhodesiae, M. seoulense,* and *M. tokaiense.*

4. The method of claim 3, wherein said *mycobacterium* is *M. tuberculosis.*

5. The method of claim 4, wherein said *mycobacterium* is an MDR strain.

6. The method of claim 4, wherein said *mycobacterium* is an XDR strain.

7. The method of claim 1, wherein said additional therapeutic agent is selected from the group consisting of NTZ, TIZ, AMIX, EMB, PZA, STR, INH, MOX, and RIF.

8. A method of killing a *mycobacterium* or inhibiting proliferation of a *mycobacterium*, said method comprising contacting said *mycobacterium* with an effective amount of a compound selected from the group consisting of

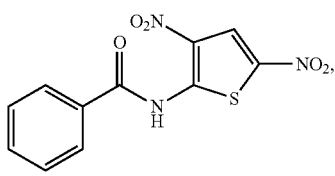
VPC16b1090

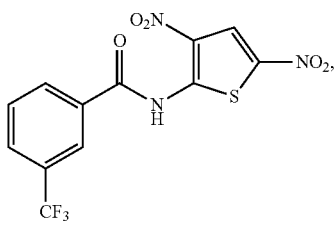
VPC16b1092

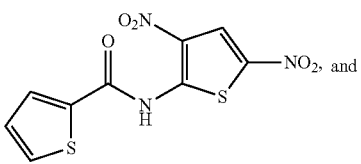
VPC16b1093

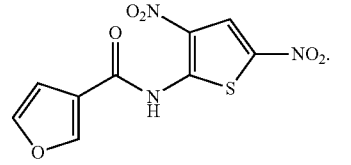
VPC16b1094

9. The method of claim 8, wherein said *mycobacterium* is selected from the group consisting of *M. tuberculosis, M. bovis, M. bovis* BCG, *M. africanum, M. canetti, M. caprae, M. microti, M. pinnipedii, M. avium, M. avium paratuberculosis, M. avium silvaticum, M. avium "hominissuis", M. colombiense, M. asiaticum, M. gordonae, M. gastri, M. kansasii, M. hiberniae, M. nonchromogenicum, M. terrae, M. triviale, M. ulcerans, M. pseudoshottsii, M. shottsii, M. triplex, M. genavense, M. florentinum, M. lentiflavum, M. palustre, M. kubicae, M. parascrofulaceum, M. heidelbergense, M. interjectum, M. simiae, M. branderi, M. cookii, M. celatum, M. bohemicum, M. haemophilum, M. malmoense, M. szulgai, M. leprae, M. lepraemurium, M. lepromatosis, M. botniense, M. chimaera, M. conspicuum, M. doricum, M. farcinogenes, M. heckeshornense, M. intracellulare, M. lacus, M. marinum, M. monacense, M. montefiorense, M. murale, M. nebraskense, M. saskatchewanense, M. scrofulaceum, M. shimoidei, M. tusciae, M. xenopi, M. intermedium, M. abscessus, M. chelonae, M. bolletii, M. fortuitum, M. fortuitum* subsp. *acetamidolyticum, M. boenickei, M. peregrinum, M. porcinum, M. senegalense, M. septicum, M. neworleansense, M.* houstonense, M. mucogenicum, M. mageritense, M. brisbanense, M. cosmeticum, M. parafortuitum, M. austroafricanum, M. diernhoferi, M. hodleri, M. neoaurum, M. frederiksbergense, M. aurum, M. vaccae, M. chitae, M. fallax, M. confluentis, M. flavescens, M. madagascariense, M. phlei, M. smegmatis, M. goodii, M. wolinskyi, M. thermoresistibile, M. gadium, M. komossense, M. obuense, M. sphagni, M. agri, M. aichiense, M. alvei, M. arupense, M. brumae, M. canariasense, M. chubuense, M. conceptionense, M. duvalii, M. elephantis, M. gilvum, M. hassiacum, M. holsaticum, M. immunogenum, M. massiliense, M. moriokaense, M. psychrotolerans, M. pyrenivorans, M. vanbaalenii, M. pulveris, M. arosiense, M. aubagnense, M. caprae, M. chlorophenolicum, M. fluoroanthenivorans, M. kumamotonense, M. novocastrense, M. parmense, M. phocaicum, M. poriferae, M. rhodesiae, M. seoulense, and M. tokaiense.

10. The method of claim 9, wherein said *mycobacterium* is *M. tuberculosis.*

11. The method of claim 10, wherein said *mycobacterium* is an MDR strain.

12. The method of claim 10, wherein said *mycobacterium* is an XDR strain.

13. The method of claim 8, wherein said compound kills said *mycobacterium.*

14. The method of claim 8, wherein said compound inhibits proliferation of said *mycobacterium.*

15. The method of claim 8, wherein said additional therapeutic agent is selected from the group consisting of NTZ, TIZ, AMIX, EMB, PZA, STR, INH, MOX, and RIF.

16. The method of claim 8, wherein said compound inhibits growth of the *mycobacterium.*

17. The method of claim 16, wherein said growth is aerobic growth.

18. The method of claim 8, wherein said compound inhibits *mycobacterium* infection.

* * * * *

UNITED STATES PATENT AND TRADEMARK OFFICE
CERTIFICATE OF CORRECTION

PATENT NO. : 9,333,193 B2
APPLICATION NO. : 13/885414
DATED : May 10, 2016
INVENTOR(S) : Paul S. Hoffman et al.

It is certified that error appears in the above-identified patent and that said Letters Patent is hereby corrected as shown below:

In the specification,

Column 1, line 10, under STATEMENT REGARDING FEDERALLY SPONSORED RESEARCH OR DEVELOPMENT, please replace "This invention was made in part with United States Government support under Grant No. U01 AI075520 awarded by the National Institutes of Health. The United States Government has certain rights in the invention."

To now read:
"This invention was made with government support under AI075520 awarded by the National Institutes of Health. The government has certain rights in the invention"

Signed and Sealed this
Nineteenth Day of July, 2016

Michelle K. Lee
*Director of the United States Patent and Trademark Office*